(12) United States Patent
Lee et al.

(10) Patent No.: US 12,297,211 B2
(45) Date of Patent: May 13, 2025

(54) COLOR CONVERSION COMPOSITION, COLOR CONVERSION FILM INCLUDING SAME, BACKLIGHT UNIT, AND DISPLAY DEVICE

(71) Applicant: LG CHEM, LTD., Seoul (KR)

(72) Inventors: Milim Lee, Daejeon (KR); Seonkyoung Son, Daejeon (KR); Duy Hieu Le, Daejeon (KR); Sang Pil Moon, Daejeon (KR); Hoyong Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 999 days.

(21) Appl. No.: 17/293,076

(22) PCT Filed: Feb. 17, 2020

(86) PCT No.: PCT/KR2020/002231
§ 371 (c)(1),
(2) Date: May 12, 2021

(87) PCT Pub. No.: WO2020/175841
PCT Pub. Date: Sep. 3, 2020

(65) Prior Publication Data
US 2021/0403488 A1 Dec. 30, 2021

(30) Foreign Application Priority Data
Feb. 28, 2019 (KR) .................. 10-2019-0023886

(51) Int. Cl.
| | | |
|---|---|---|
| C07D 519/00 | (2006.01) | |
| C07F 5/02 | (2006.01) | |
| C07F 7/08 | (2006.01) | |
| G02F 1/13357 | (2006.01) | |
| H10H 20/851 | (2025.01) | |
| H10K 85/40 | (2023.01) | |
| H10K 85/60 | (2023.01) | |

(52) U.S. Cl.
CPC ............ *C07D 519/00* (2013.01); *C07F 5/022* (2013.01); *C07F 7/0812* (2013.01); *G02F 1/133603* (2013.01); *H10H 20/8512* (2025.01); *H10K 85/40* (2023.02); *H10K 85/622* (2023.02); *H10K 85/624* (2023.02); *H10K 85/626* (2023.02); *H10K 85/636* (2023.02); *H10K 85/655* (2023.02); *H10K 85/6572* (2023.02); *H10K 85/6574* (2023.02); *H10K 85/6576* (2023.02)

(58) Field of Classification Search
CPC .. C07D 519/00; H10K 85/624; H10K 85/636; H10K 85/655; H10K 85/6574; H10K 85/622; H10K 85/6576; H10K 85/626; H10K 85/6572; H10K 85/40; C07F 5/022; C07F 7/0812; G02F 1/133603; H01L 33/502

See application file for complete search history.

(56) References Cited

U.S. PATENT DOCUMENTS

| | | |
|---|---|---|
| 10,961,260 B2 | 3/2021 | Son et al. |
| 2016/0133845 A1 | 5/2016 | Jung et al. |
| 2016/0223162 A1 | 8/2016 | Shin et al. |
| 2016/0223728 A1* | 8/2016 | Shin ................. G02B 6/0073 |
| 2018/0179439 A1 | 6/2018 | Umehara et al. |
| 2019/0263836 A1 | 8/2019 | Oh et al. |
| 2020/0032138 A1 | 1/2020 | Lee et al. |
| 2020/0317999 A1 | 10/2020 | Wang et al. |
| 2020/0331932 A1 | 10/2020 | Son et al. |

FOREIGN PATENT DOCUMENTS

| | | |
|---|---|---|
| CN | 103865290 A | 6/2014 |
| CN | 109154732 A | 1/2019 |
| KR | 10-2016-0079375 A | 7/2016 |
| KR | 10-2016-0094890 A | 8/2016 |
| KR | 10-2018-0013798 A | 2/2018 |
| KR | 10-2018-0022705 A | 3/2018 |
| KR | 10-2018-0047381 A | 5/2018 |
| KR | 10-2018-0055712 A | 5/2018 |
| KR | 10-2018-0111095 A | 10/2018 |
| TW | 2016-17327 A | 5/2016 |
| WO | 2018-093119 A1 | 5/2018 |
| WO | 2018-093121 A1 | 5/2018 |

OTHER PUBLICATIONS

Cheng et al., Organic Letters, 2015, 17, 278-281. Published Dec. 31, 2014 (Year: 2014).*
Gawale et al., Journal of Photochemistry & Photobiology, B: Biology, 178, 2018, 472-480. Published online Dec. 7, 2017 (Year: 2017).*
Jin et al., New Journal of Chemistry, 2015, 39, 8188-8194. Published Aug. 17, 2015. (Year: 2015).*
Office Action issued for Japanese Patent Application No. 2021-520604 on May 17, 2022, with English translation, 6 pages.
International Search Report and Written Opinion issued for International Application No. PCT/KR2020/002231 on May 25, 2020, 10 pages.

\* cited by examiner

*Primary Examiner* — Jane L Stanley
(74) *Attorney, Agent, or Firm* — ROTHWELL, FIGG, ERNST & MANBECK, P.C.

(57) ABSTRACT

The present specification relates to a color conversion composition including a compound represented by Chemical Formula 1 and a compound represented by Chemical Formula 2 in a molar ratio of 1:1 to 5:1, and a color conversion film, a backlight unit and a display apparatus including the same.

12 Claims, No Drawings

COLOR CONVERSION COMPOSITION, COLOR CONVERSION FILM INCLUDING SAME, BACKLIGHT UNIT, AND DISPLAY DEVICE

This application is a 35 U.S.C. 371 National Phase Entry application from PCT/KR2020/002231, filed on Feb. 17, 2020 and designating the United States, which claims priority to and the benefits of Korean Patent Application No. 10-2019-0023886, filed with the Korean Intellectual Property Office on Feb. 28, 2019, the entire contents of which are incorporated herein by reference.

TECHNICAL FIELD

The present specification relates to a color conversion composition, and a color conversion film, a backlight unit and a display apparatus including the same.

BACKGROUND OF THE INVENTION

Existing light emitting diodes (LED) are obtained by mixing a green phosphorescent substance and a red phosphorescent substance to a blue light emitting diode, or mixing a yellow phosphorescent substance and a blue-green phosphorescent substance to a UV light emitting diode. However, with such a method, it is difficult to control colors, and therefore, color rendering is not favorable. Accordingly, color gamut declines.

In order to overcome such color gamut decline and to reduce production costs, methods of obtaining green and red in a manner of filming quantum dots and binding the dots to a blue LED have been recently tried. However, cadmium series quantum dots have safety problems, and other quantum dots have significantly decreased efficiency compared to cadmium series quantum dots. In addition, quantum dots have reduced stability for oxygen and water, and have a disadvantage in that the performance is significantly degraded when aggregated. Furthermore, unit costs of production are high since, when producing quantum dots, maintaining the sizes to be constant is difficult.

Existing compounds having a BODIPY structure has a narrow light emission full width at half maximum, and is suited for obtaining high color reproduction and high efficiency when used as a color conversion film, but has insufficient absorption for light of a light source due to a narrow light absorption region. Accordingly, in order to absorb blue light and efficiently converting the blue light to green and red, an auxiliary fluorescent substance helping with energy transfer by assisting light absorption of the BODIOY structure has been required.

BRIEF SUMMARY OF THE INVENTION

The present disclosure is directed to providing a color conversion composition, and a color conversion film, a backlight unit and a display apparatus including the same.

One embodiment of the present disclosure provides a color conversion composition including a compound represented by the following Chemical Formula 1 and a compound represented by the following Chemical Formula 2, wherein the compound represented by Chemical Formula 1 and the compound represented by Chemical Formula 2 have a molar ratio of 1:1 to 5:1.

[Chemical Formula 1]

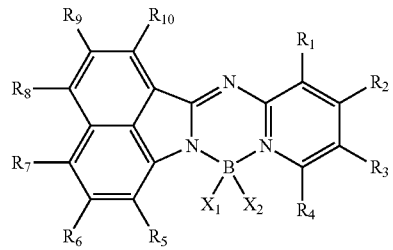

[Chemical Formula 2]

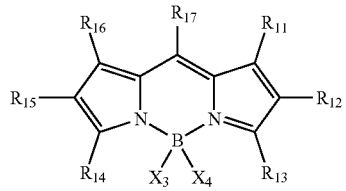

In Chemical Formulae 1 and 2, $X_1$ to $X_4$ are the same as or different from each other, and each independently a halogen group; a cyano group; a hydroxyl group; —$OR_A$; —$C(=O)OR_B$; —$OC(=O)R_C$; a substituted or unsubstituted alkyl group; a substituted or unsubstituted alkynyl group; a substituted or unsubstituted aryl group; or a substituted or unsubstituted aralkyl group, $R_1$ to $R_{17}$ are the same as or different from each other, and each independently hydrogen; deuterium; a halogen group; a cyano group; —$OR_D$; —$C(=O)OR_E$; —$OC(=O)R_F$; —$R_GOR_H$; —$SR_I$; —$S(=O)_2OR_J$; a substituted or unsubstituted amine group; a substituted or unsubstituted silyl group; a substituted or unsubstituted alkyl group; a substituted or unsubstituted alkenyl group; a substituted or unsubstituted alkynyl group; a substituted or unsubstituted cycloalkyl group; a substituted or unsubstituted aryl group; a substituted or unsubstituted heteroaryl group; or a substituted or unsubstituted coumarin group, or adjacent groups bond to each other to form a ring, and $R_A$ to $R_J$ are the same as or different from each other, and each independently a substituted or unsubstituted alkyl group; a substituted or unsubstituted aryl group; a substituted or unsubstituted heteroaryl group; a substituted or unsubstituted coumarin group; or a substituted or unsubstituted naphthalimide group.

Another embodiment of the present disclosure provides a color conversion composition including a compound having a maximum absorption wavelength in a wavelength region of 400 nm to 500 nm and a compound having a maximum emission wavelength in a wavelength region of 500 nm to 650 nm.

Another embodiment of the present disclosure provides a color conversion film including a resin matrix; and the color conversion composition dispersed into the resin matrix.

Another embodiment of the present disclosure provides a backlight unit including the color conversion film.

Another embodiment of the present disclosure provides a display apparatus including the backlight unit.

Advantageous Effects

By including a compound of Chemical Formula 1 as an auxiliary fluorescent substance together with a compound of Chemical Formula 2, a color conversion composition according to one embodiment of the present disclosure is capable of enhancing green and red luminance as well as enhancing a blue light absorption rate compared to when using only an existing compound having a bodipy structure. Accordingly, by using the color conversion composition described in the present disclosure as a fluorescent material of a color conversion film under blue backlight, a color conversion film having excellent luminance and color gamut, and excellent durability can be provided.

Particularly, the compound of Chemical Formula 2 has favorable light emission efficiency when including the compound of Chemical Formula 1 and the compound of Chemical Formula 2 in a molar ratio of 1:1 to 5:1.

DESCRIPTION OF DRAWINGS

FIG. 1 is a mimetic diagram illustrating a structure of a backlight unit according to one embodiment of the present disclosure.

FIG. 2 is a mimetic diagram illustrating a structure of a display apparatus according to one embodiment of the present disclosure.

DETAILED DESCRIPTION OF THE INVENTION

Hereinafter, the present application will be described in more detail.

One embodiment of the present specification provides a color conversion composition including a compound represented by Chemical Formula 1 and a compound represented by Chemical Formula 2.

In the present specification, a certain part "including" certain constituents means capable of further including other constituents, and does not exclude other constituents unless particularly stated on the contrary.

In the present specification, one member being placed "on" another member includes not only a case of the one member being in contact with the another member but a case of still another member being present between the two members.

In the present specification, ⚹ means a position where a substituent bonds.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, adjacent groups bonding to each other to form a ring means, as described above, adjacent groups bonding to each other to form a substituted or unsubstituted hydrocarbon ring or a substituted or unsubstituted heteroring, and adjacent groups bonding to each other to form a monocyclic or polycyclic ring, an aliphatic, aromatic or fused form thereof, and the form is not limited thereto.

In the present specification, bonding to adjacent groups to form a ring means bonding to adjacent groups to form a substituted or unsubstituted aliphatic hydrocarbon ring; a substituted or unsubstituted aromatic hydrocarbon ring; a substituted or unsubstituted aliphatic heteroring; a substituted or unsubstituted aromatic heteroring; or a combined form thereof.

In the present specification, the aliphatic hydrocarbon ring means, as a ring that is not aromatic, a ring formed only with carbon and hydrogen atoms.

In the present specification, examples of the aromatic hydrocarbon ring may include a phenyl group, a naphthyl group, an anthracenyl group and the like, but are not limited thereto.

In the present specification, the aliphatic heteroring means an aliphatic ring including one or more of heteroatoms.

In the present specification, the aromatic heteroring means an aromatic ring including one or more of heteroatoms.

Examples of substituents in the present specification are described below, however, the substituents are not limited thereto.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a cyano group; a nitro group; —C(=O)R; —C(=O)OR'; —OC(=O)R"; an imide group; an amide group; a hydroxyl group; a substituted or unsubstituted amine group; a substituted or unsubstituted silyl group; a substituted or unsubstituted alkyl group; a substituted or unsubstituted cycloalkyl group; a substituted or unsubstituted haloalkyl group; a substituted or unsubstituted alkoxy group; a substituted or unsubstituted alkenyl group; a substituted or unsubstituted alkynyl group; a substituted or unsubstituted aryl group; a substituted or unsubstituted aryloxy group; a substituted or unsubstituted arylthioxy group; a substituted or unsubstituted heteroaryl group; a substituted or unsubstituted coumarin group; or

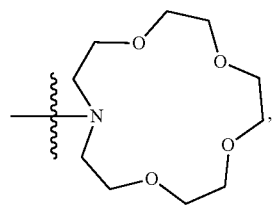 [SMILES: *N1CCOCCOCCOCCOCC1]

or being substituted with a substituent linking two or more substituents among the substituents illustrated above, or having no substituents, and R, R' and R" are a substituted or unsubstituted alkyl group; a substituted or unsubstituted alkenyl group; a substituted or unsubstituted aryl group; a substituted or unsubstituted heteroaryl group; or a substituted or unsubstituted coumarin group.

In the present specification, examples of the halogen group may include fluorine, chlorine, bromine or iodine.

In the present specification, the number of carbon atoms of the imide group is not particularly limited, but is preferably from 1 to 30.

In the present specification, in the amide group, nitrogen of the amide group may be substituted with hydrogen, a linear, branched or cyclic alkyl group having 1 to 30 carbon atoms, or an aryl group having 6 to 30 carbon atoms.

In the present specification, the amine group may be selected from the group consisting of —NH$_2$; a monoalkylamine group; a dialkylamine group; an N-alkylamine group; a monoarylamine group; a diarylamine group; an N-arylheteroarylamine group; an N-alkylheteroarylamine group, a monoheteroarylamine group and a diheteroarylamine group, and, although not particularly limited thereto, the number of carbon atoms is preferably from 1 to 30.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, the alkyl group in the alkylamine group, the N-alkylarylamine group, the alkylthioxy group, the alkylsulfoxy group and the N-alkylheteroarylamine group is the same as the examples of the alkyl group described above.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the alkyl group may be linear or branched, and although not particularly limited thereto, the number of carbon atoms is preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methyl pentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl and the like, but are not limited thereto.

In the present specification, the cycloalkyl group is not particularly limited, but preferably has 3 to 30 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the haloalkyl group represents an alkyl group in which a hydrogen atom of the alkyl group is replaced by the same or a different halogen group. The haloalkyl group may be linear or branched, and although not particularly limited thereto, the number of carbon atoms is preferably from 1 to 10. Specific examples thereof may include —CH$_2$Cl, —CF$_3$, —CH$_2$CF$_3$, —CF$_2$CF$_3$ and the like, but are not limited thereto.

In the present specification, the alkoxy group may be linear, branched or cyclic. The number of carbon atoms of the alkoxy group is not particularly limited, but is preferably from 1 to 30. In the present specification, the alkenyl group may be linear or branched, and although not particularly limited thereto, the number of carbon atoms is preferably from 2 to 30.

In the present specification, the alkynyl group may be linear or branched, and although not particularly limited thereto, the number of carbon atoms is preferably from 2 to 30. Specific examples thereof may include alkynyl groups such as ethynyl, propynyl, 2-methyl-2-propynyl, 2-butynyl, 2-pentynyl and the like, but are not limited thereto.

In the present specification, the aryl group is not particularly limited, but preferably has 6 to 30 carbon atoms, and the aryl group may be monocyclic or polycyclic.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group may include a naphthyl group, an anthracenyl group, a phenanthryl group, a triphenyl group, a pyrenyl group, a perylenyl group, a chrysenyl group, a fluorenyl group and the like, but are not limited thereto.

In the present specification, the aryl group may be substituted, and adjacent groups may bond to each other to form a ring.

In the present specification, the fluorenyl group may be substituted, and adjacent groups may bond to each other to form a ring.

When the fluorenyl group is substituted,

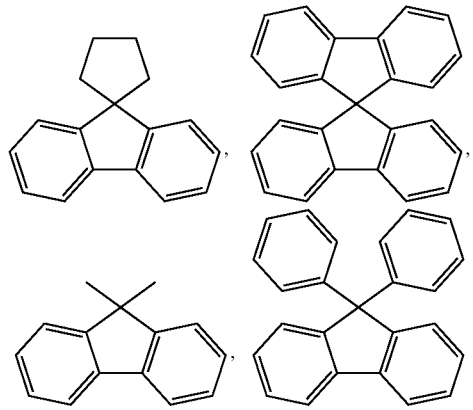

and the like may be included. However, the structure is not limited thereto.

In the present specification, the aryl group in the aryloxy group and the arylthioxy group is the same as the examples of the aryl group described above. Specific examples of the aryloxy group may include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like, specific examples of the arylthioxy group may include a phenylthioxy group, a 2-methylphenylthioxy group, a 4-tert-butylphenylthioxy group and the like, however, the aryloxy group and the arylthioxy group are not limited thereto.

In the present specification, the heteroaryl group is a group including one or more atoms that are not carbon, that is, heteroatoms, and specifically, the heteroatom may include one or more atoms selected from the group consisting of O, N, Se, S and the like. The number of carbon atoms is not particularly limited, but is preferably from 2 to 30, and the heteroaryl group may be monocyclic or polycyclic. Examples of the heteroaryl group may include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, a thiazolyl group, an isoxazolyl group, an oxadiazolyl group, a thiadiazolyl group, a phenothiazinyl group, a dibenzofuranyl group and the like, but are not limited thereto.

In the present specification, in the coumarin group, carbon of the coumarin group may be substituted with a halogen group, a nitrile group, a linear, branched or cyclic alkyl group having 1 to 25 carbon atoms; an amine group; a linear or branched alkoxy group having 1 to 25 carbon atoms; or an aryl group having 6 to 30 carbon atoms.

In one embodiment of the present specification, the compound represented by Chemical Formula 1 is an azabodipy-based compound, and the compound represented by Chemical Formula 2 is a bodipy-based compound. When preparing a color conversion film using a color conversion composition including both an azabodipy-based compound and a bodipy-based compound, a color conversion film having excellent luminance and color gamut, and excellent durability may be provided.

In one embodiment of the present specification, the compound represented by Chemical Formula 1 and the compound represented by Chemical Formula 2 have a molar ratio of 1:1 to 5:1. When including the compound of Chemical Formula 1 and the compound of Chemical Formula 2 in the above-described molar ratio range, the compound of Chemical Formula 2 has excellent light emission efficiency. Specifically, the more the compound of Chemical Formula 2 is included based on the molar ratio of 1:1, the amount of blue light absorption rapidly decreases. In addition, when the amount of the compound of Chemical Formula 1 included is within 5 times of the number of moles of the compound of Chemical Formula 2, a rate of blue light absorption and a rate of luminance increase are high, and accordingly, efficiency is superior considering the amount of a dye used.

In one embodiment of the present specification, the compound represented by Chemical Formula 1 has a maximum absorption wavelength in a wavelength region of 400 nm to 500 nm. Energy transfer to the bodipy may occur by effectively absorbing a blue light OLED.

In one embodiment of the present specification, the compound represented by Chemical Formula 2 has a maximum emission wavelength in a wavelength region of 500 nm to 650 nm. Luminance and color gamut may be enhanced by using a compound having maximum emission in a target wavelength region.

When using the compound represented by Chemical Formula 2 alone, color conversion in green and red regions is low due to insignificant absorption of a blue light source, however, when using the compound of Chemical Formula 1 having high absorption in a blue light region therewith, energy transfer occurs in the order of blue light, the compound of Chemical Formula 1 and the compound of Chemical Formula 2, and fluorescence properties of the compound of Chemical Formula 2 are finally obtained.

A color conversion composition according to another embodiment of the present specification includes a compound having a maximum absorption wavelength in a wavelength region of 400 nm to 500 nm and a compound having a maximum emission wavelength in a wavelength region of 500 nm to 650 nm.

The compound having a maximum absorption wavelength in a wavelength region of 400 nm to 500 nm may be represented by Chemical Formula 1, and the compound having a maximum emission wavelength in a wavelength region of 500 nm to 650 nm may be represented by Chemical Formula 2.

In one embodiment of the present specification, $X_1$ to $X_4$ are the same as or different from each other, and each independently a halogen group; a cyano group; a hydroxyl group; —$OR_A$; —$C(=O)OR_B$; —$OC(=O)R_C$; a substituted or unsubstituted alkyl group; a substituted or unsubstituted alkynyl group; a substituted or unsubstituted aryl group; or a substituted or unsubstituted aralkyl group.

In one embodiment of the present specification, $X_1$ and $X_2$ are the same as or different from each other, and each independently a halogen group; a cyano group; —$OR_A$; —$C(=O)OR_B$; —$OC(=O)R_C$; a substituted or unsubstituted C1 to C20 alkyl group; a substituted or unsubstituted C1 to C20 alkynyl group; a substituted or unsubstituted C6 to C30 aryl group; or a substituted or unsubstituted C6 to C30 heteroaryl group.

In one embodiment of the present specification, $X_1$ and $X_2$ are the same as or different from each other, and each independently a halogen group; a cyano group; —$OR_A$; —$C(=O)OR_B$; a substituted or unsubstituted methyl group; a substituted or unsubstituted ethynyl group; a substituted or unsubstituted phenyl group; a substituted or unsubstituted fluorenyl group; or a substituted or unsubstituted thiophene group.

In one embodiment of the present specification, $X_1$ and $X_2$ are the same as or different from each other, and each independently a halogen group; a cyano group; —$OR_A$; —$C(=O)OR_B$; a methyl group; a substituted or unsubstituted ethynyl group; a phenyl group unsubstituted or substituted with a halogen group; a substituted or unsubstituted fluorenyl group; or a thiophene group.

In one embodiment of the present specification, $X_1$ and $X_2$ are each independently —$OR_A$, and $R_A$ is a substituted or unsubstituted aryl group.

In one embodiment of the present specification, $X_1$ and $X_2$ are each independently —$OR_A$, and $R_A$ is a substituted or unsubstituted phenyl group.

In one embodiment of the present specification, $X_1$ and $X_2$ are each independently —$OR_A$, and $R_A$ is a phenyl group unsubstituted or substituted with a nitro group.

In one embodiment of the present specification, $X_1$ and $X_2$ are each independently —$C(=O)OR_B$, and $R_B$ is a substituted or unsubstituted alkyl group.

In one embodiment of the present specification, $X_1$ and $X_2$ are each independently —$C(=O)OR_B$, and $R_B$ is an alkyl group unsubstituted or substituted with a haloalkyl group.

In one embodiment of the present specification, $X_3$ and $X_4$ are the same as or different from each other, and each independently a halogen group; a cyano group; a hydroxyl group; —OR$_A$; —C(=O)OR$_B$; —OC(=O)R$_C$; a substituted or unsubstituted C1 to C20 alkyl group; a substituted or unsubstituted C1 to C20 alkynyl group; a substituted or unsubstituted C6 to C30 aryl group; or a substituted or unsubstituted C6 to C30 heteroaryl group.

In one embodiment of the present specification, X$_3$ and X$_4$ are the same as or different from each other, and each independently a halogen group; a cyano group; a hydroxyl group; —OR$_A$; —OC(=O)R$_C$; a substituted or unsubstituted ethynyl group; a substituted or unsubstituted naphthyl group; or a substituted or unsubstituted perylenyl group.

In one embodiment of the present specification, X$_3$ and X$_4$ are the same as or different from each other, and each independently a halogen group; a cyano group; a hydroxyl group; —OR$_A$; —OC(=O)R$_C$; a substituted or unsubstituted ethynyl group; a naphthyl group; or a perylenyl group.

In one embodiment of the present specification, X$_3$ and X$_4$ are each independently —OR$_A$, and R$_A$ is a substituted or unsubstituted alkyl group; or a substituted or unsubstituted aryl group.

In one embodiment of the present specification, X$_3$ and X$_4$ are each independently —OR$_A$, and R$_A$ is a substituted or unsubstituted methyl group; or a substituted or unsubstituted phenyl group.

In one embodiment of the present specification, X$_3$ and X$_4$ are each independently —OR$_A$, and R$_A$ is a methyl group unsubstituted or substituted with a haloalkyl group; or a phenyl group unsubstituted or substituted with a nitro group.

In one embodiment of the present specification, X$_3$ and X$_4$ are each independently —OC(=O)R$_C$, and R$_C$ is a substituted or unsubstituted alkyl group.

In one embodiment of the present specification, X$_3$ and X$_4$ are each independently —OC(=O)R$_C$, and R$_C$ is a substituted or unsubstituted methyl group.

In one embodiment of the present specification, X$_3$ and X$_4$ are each independently —OC(=O)R$_C$, and R$_C$ is a methyl group unsubstituted or substituted with a halogen group.

In one embodiment of the present specification, R$_1$ to R$_{17}$ are the same as or different from each other, and each independently hydrogen; deuterium; a halogen group; a cyano group; —OR$_D$; —C(=O)OR$_E$; —OC(=O)R$_F$; —R$_G$OR$_H$; —SR$_I$; —S(=O)$_2$OR$_J$; a substituted or unsubstituted amine group; a substituted or unsubstituted silyl group; a substituted or unsubstituted alkyl group; a substituted or unsubstituted alkenyl group; a substituted or unsubstituted alkynyl group; a substituted or unsubstituted cycloalkyl group; a substituted or unsubstituted aryl group; a substituted or unsubstituted heteroaryl group; or a substituted or unsubstituted coumarin group, or adjacent groups may bond to each other to form a ring.

In one embodiment of the present specification, R$_1$ to R$_{10}$ are the same as or different from each other, and each independently hydrogen; deuterium; a halogen group; a cyano group; —OR$_D$; —C(=O)OR$_E$; —SR$_I$; a substituted or unsubstituted amine group; a substituted or unsubstituted silyl group; a substituted or unsubstituted alkyl group; a substituted or unsubstituted alkenyl group; a substituted or unsubstituted alkynyl group; a substituted or unsubstituted aryl group; or a substituted or unsubstituted heteroaryl group, or adjacent groups may bond to each other to form a ring.

In one embodiment of the present specification, R$_1$ to R$_{10}$ are the same as or different from each other, and each independently hydrogen; deuterium; a halogen group; a cyano group; —OR$_D$; —C(=O)OR$_E$; —SR$_I$; a substituted or unsubstituted amine group; a substituted or unsubstituted silyl group; a substituted or unsubstituted C1 to C20 alkyl group; a substituted or unsubstituted C1 to C20 alkenyl group; a substituted or unsubstituted C1 to C20 alkynyl group; a substituted or unsubstituted C6 to C30 aryl group; or a substituted or unsubstituted C2 to C30 heteroaryl group, or adjacent groups may bond to each other to form a ring.

In one embodiment of the present specification, R$_1$ to R$_{10}$ are the same as or different from each other, and each independently hydrogen; deuterium; a halogen group; a cyano group; a pyridine group; a pyrrole group; a thiophene group; an oxazole group; a thiazole group; —OR$_D$; —C(=O)OR$_E$; —SR$_I$; an amine group unsubstituted or substituted with one or more substituents selected from the group consisting of an alkyl group and an aryl group; a silyl group unsubstituted or substituted with an aryl group; an alkyl group unsubstituted or substituted with a halogen group; an alkenyl group unsubstituted or substituted with one or more substituents selected from the group consisting of a cyano group and an aryl group; a substituted or unsubstituted ethynyl group; a substituted or unsubstituted phenyl group; a substituted or unsubstituted naphthyl group; a substituted or unsubstituted indene group; a substituted or unsubstituted dihydroindene group; a substituted or unsubstituted fluorenyl group; a substituted or unsubstituted benzoxazole group; a substituted or unsubstituted benzofuran group; a substituted or unsubstituted indole group; a substituted or unsubstituted quinoxaline group; a substituted or unsubstituted dibenzofuran group; a substituted or unsubstituted dibenzothiophene group; or a substituted or unsubstituted carbazole group, or adjacent groups may bond to each other to form a ring.

In one embodiment of the present specification, when R$_1$ to R$_{10}$ are each independently —C(=O)OR$_E$, R$_E$ is a substituted or unsubstituted alkyl group; a substituted or unsubstituted aryl group; a substituted or unsubstituted coumarin group; or a substituted or unsubstituted naphthalimide group.

In one embodiment of the present specification, when R$_1$ to R$_{10}$ are each independently —SR$_I$, R$_I$ is a substituted or unsubstituted alkyl group.

In one embodiment of the present specification, R$_{11}$ to R$_{16}$ are the same as or different from each other, and each independently hydrogen; deuterium; a halogen group; a cyano group; —OR$_D$; —C(=O)OR$_E$; —R$_G$OR$_H$; —SR$_I$; —S(=O)$_2$OR$_J$; a substituted or unsubstituted amine group; a substituted or unsubstituted silyl group; a substituted or unsubstituted alkyl group; a substituted or unsubstituted cycloalkyl group; a substituted or unsubstituted alkenyl group; a substituted or unsubstituted alkynyl group; a substituted or unsubstituted aryl group; a substituted or unsubstituted heteroaryl group; or a substituted or unsubstituted coumarin group, or adjacent groups may bond to each other to form a ring.

In one embodiment of the present specification, R$_{11}$ to R$_{16}$ are the same as or different from each other, and each independently hydrogen; deuterium; a halogen group; a cyano group; —OR$_D$; —C(=O)OR$_E$; —R$_G$OR$_H$; —SR$_I$; —S(=O)$_2$OR$_J$; a substituted or unsubstituted amine group; a substituted or unsubstituted silyl group; a substituted or unsubstituted C1 to C20 alkyl group; a substituted or unsubstituted C3 to C20 cycloalkyl group; a substituted or unsubstituted C1 to C20 alkenyl group; a substituted or unsubstituted C1 to C20 alkynyl group; a substituted or unsubstituted C6 to C30 aryl group; a substituted or unsubstituted C2 to C30 heteroaryl group; or a substituted or unsubstituted coumarin group, or adjacent groups may bond to each other to form a ring.

In one embodiment of the present specification, $R_{11}$ to $R_{16}$ are the same as or different from each other, and each independently hydrogen; deuterium; a halogen group; a cyano group; a pyrrole group; —$OR_D$; —$C(=O)OR_E$; —$R_GOR_H$; —$SR_I$; —$S(=O)_2OR_J$; a substituted or unsubstituted amine group; a substituted or unsubstituted silyl group; a substituted or unsubstituted alkyl group; a substituted or unsubstituted cyclohexyl group; an alkenyl group unsubstituted or substituted with an aryl group; a substituted or unsubstituted ethynyl group; a substituted or unsubstituted phenyl group; a substituted or unsubstituted biphenyl group; a substituted or unsubstituted naphthyl group; a substituted or unsubstituted fluorenyl group; a substituted or unsubstituted thiophene group; a substituted or unsubstituted dibenzofuran group; a substituted or unsubstituted carbazole group; or a substituted or unsubstituted coumarin group, or adjacent groups may bond to each other to form a ring.

In one embodiment of the present specification, when $R_{11}$ to $R_{16}$ are each independently —$OR_D$, $R_D$ is a substituted or unsubstituted alkyl group; or a substituted or unsubstituted aryl group.

In one embodiment of the present specification, when $R_{11}$ to $R_{16}$ are each independently —$C(=O)OR_E$, $R_E$ is a substituted or unsubstituted alkyl group; a substituted or unsubstituted aryl group; a substituted or unsubstituted coumarin group; or a substituted or unsubstituted naphthalimide group.

In one embodiment of the present specification, when $R_{11}$ to $R_{16}$ are each independently —$OC(=O)R_F$, $R_F$ is a substituted or unsubstituted alkyl group.

In one embodiment of the present specification, when $R_{11}$ to $R_{16}$ are each independently —$R_GOR_H$, $R_G$ and $R_H$ are each independently a substituted or unsubstituted alkyl group; or a substituted or unsubstituted aryl group.

In one embodiment of the present specification, when $R_{11}$ to $R_{16}$ are each independently —$SR_I$, $R_I$ is a substituted or unsubstituted aryl group.

In one embodiment of the present specification, when $R_{11}$ to $R_{16}$ are each independently —$S(=O)_2OR_J$, $R_J$ is a substituted or unsubstituted alkyl group.

In one embodiment of the present specification, $R_{17}$ is hydrogen; deuterium; a halogen group; a cyano group; —$OR_D$; —$C(=O)OR_E$; —$SR_I$; a substituted or unsubstituted amine group; a substituted or unsubstituted alkyl group; a substituted or unsubstituted cycloalkyl group; a substituted or unsubstituted aryl group; a substituted or unsubstituted heteroaryl group; or a substituted or unsubstituted coumarin group.

In one embodiment of the present specification, $R_{17}$ is hydrogen; deuterium; a halogen group; a cyano group; —$OR_D$; —$C(=O)OR_E$; —$SR_I$; a substituted or unsubstituted amine group; a substituted or unsubstituted C1 to C20 alkyl group; a substituted or unsubstituted C3 to C30 cycloalkyl group; a substituted or unsubstituted C6 to C30 aryl group; a substituted or unsubstituted C2 to C30 heteroaryl group; or a substituted or unsubstituted coumarin group.

In one embodiment of the present specification, $R_{17}$ is hydrogen; deuterium; a halogen group; a cyano group; a pyrenyl group; a pyridine group; a furan group; a thiophene group; —$OR_D$; —$C(=O)OR_E$; —$SR_I$; a substituted or unsubstituted amine group; a substituted or unsubstituted methyl group; a substituted or unsubstituted cyclohexyl group; a substituted or unsubstituted phenyl group; a substituted or unsubstituted naphthyl group; a substituted or unsubstituted fluorenyl group; a substituted or unsubstituted dibenzofuran group; a substituted or unsubstituted dibenzothiophene group; a substituted or unsubstituted carbazole group; or a substituted or unsubstituted coumarin group.

In one embodiment of the present specification, when $R_{17}$ is —$OR_D$, $R_D$ is a substituted or unsubstituted alkyl group; a substituted or unsubstituted aryl group; a substituted or unsubstituted heteroaryl group; or a substituted or unsubstituted coumarin group.

In one embodiment of the present specification, when $R_{17}$ is —$OR_D$, $R_D$ is a substituted or unsubstituted methyl group; a substituted or unsubstituted phenyl group; a substituted or unsubstituted dibenzofuran group; or a substituted or unsubstituted coumarin group.

In one embodiment of the present specification, when $R_{17}$ is —$C(=O)OR_E$, $R_E$ is a substituted or unsubstituted alkyl group.

In one embodiment of the present specification, when $R_{17}$ is —$SR_I$, $R_I$ is a substituted or unsubstituted alkyl group; or a substituted or unsubstituted coumarin group.

In one embodiment of the present specification, the compound represented by Chemical Formula 1 is represented by any one of the following compounds.

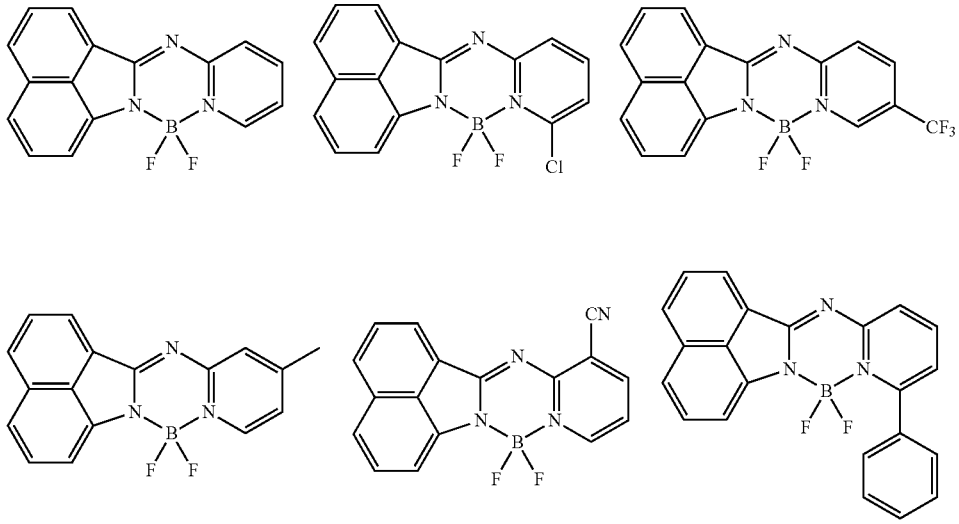

-continued
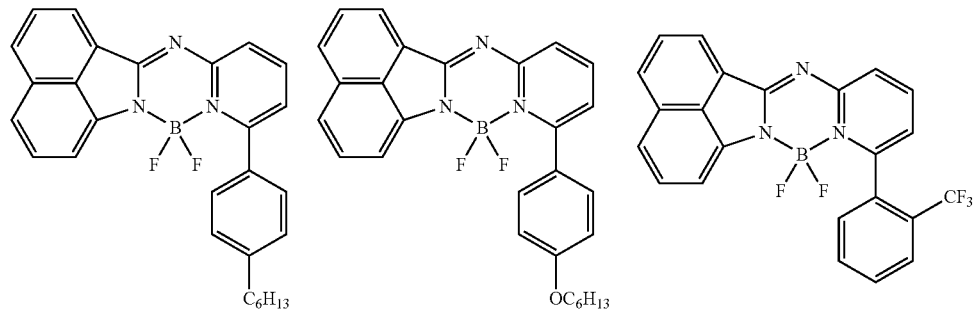
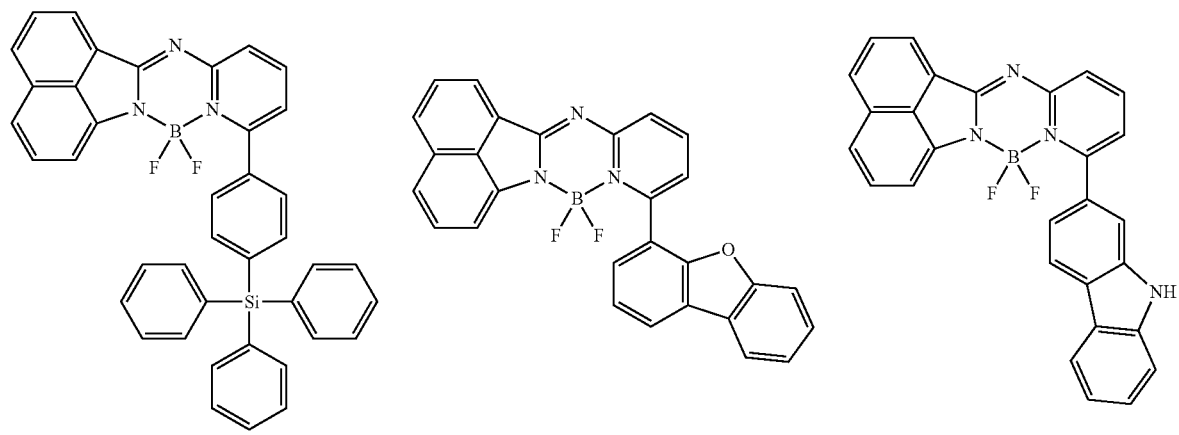
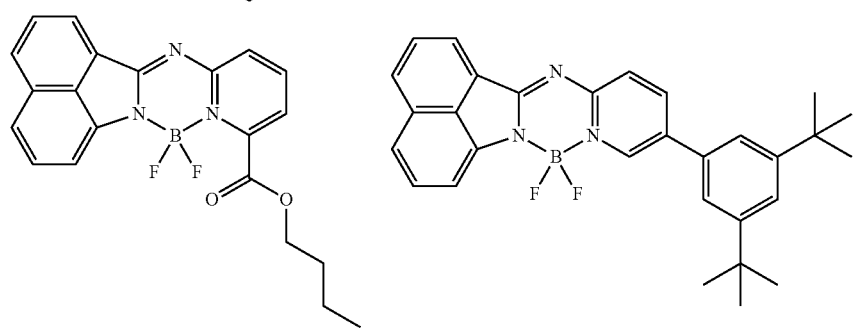
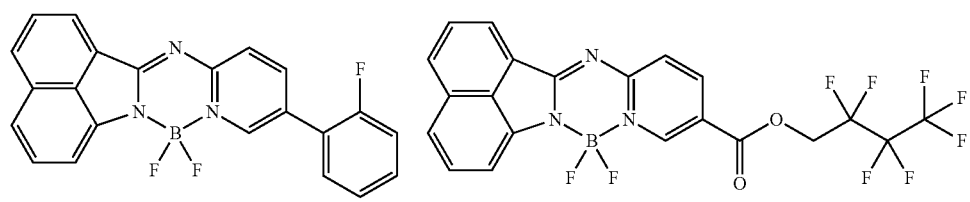
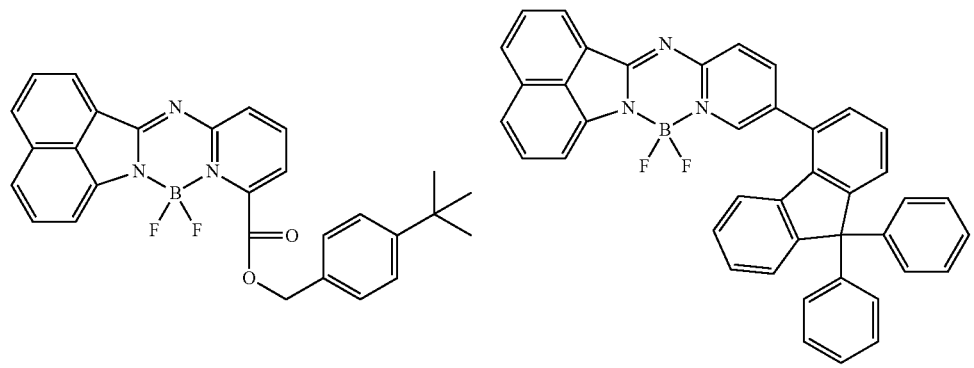

-continued
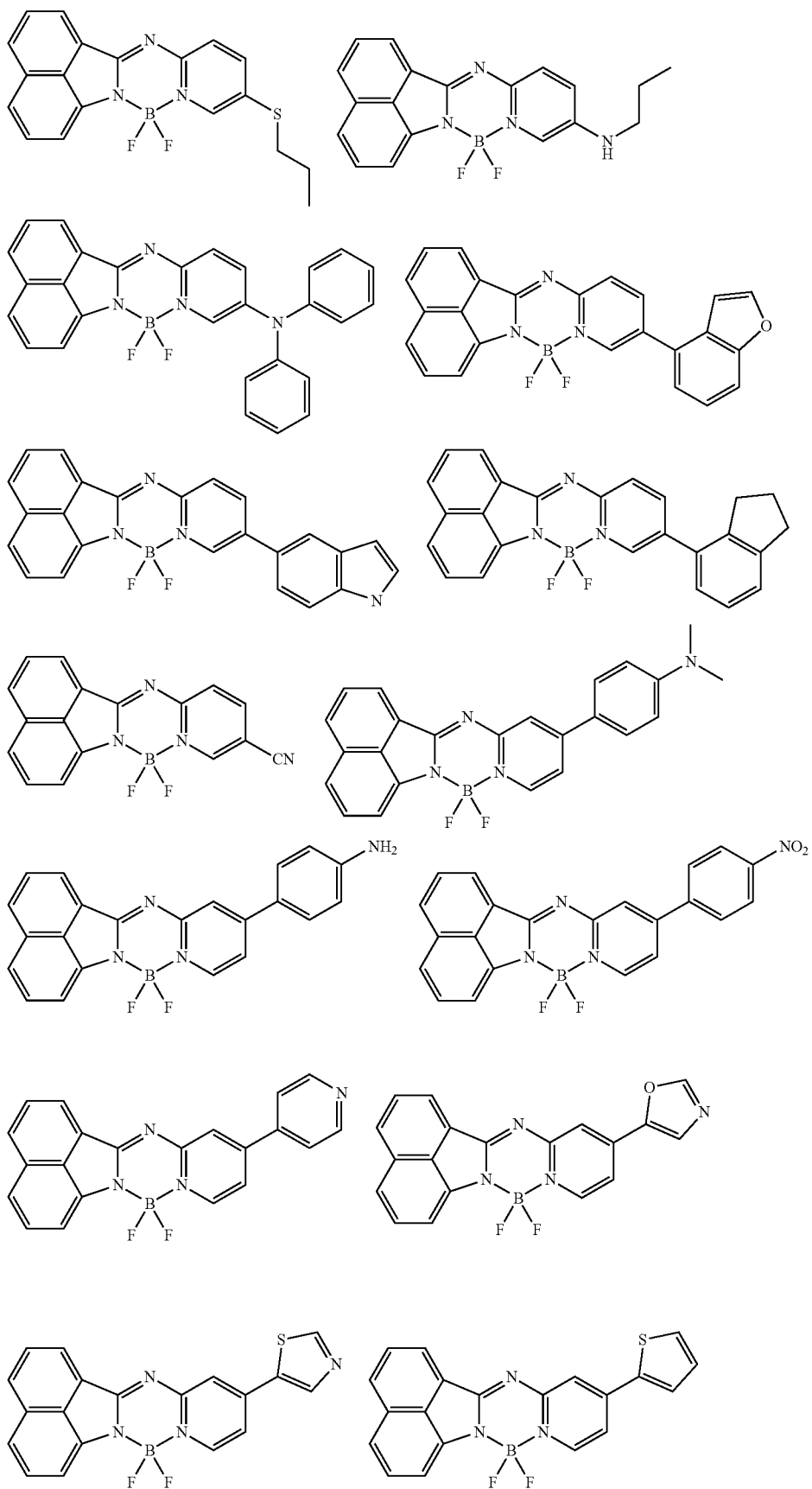

-continued
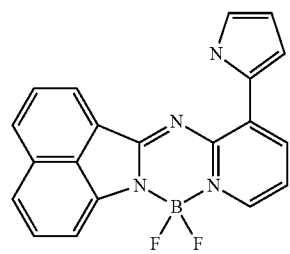
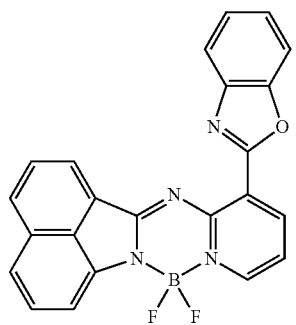
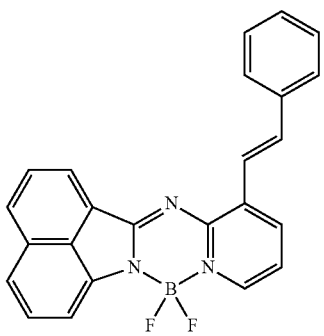
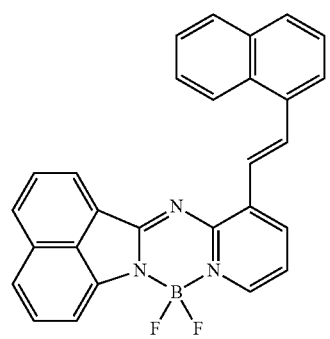
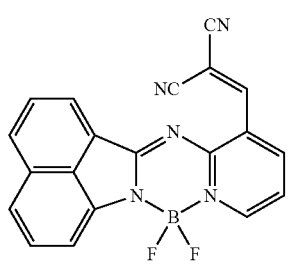
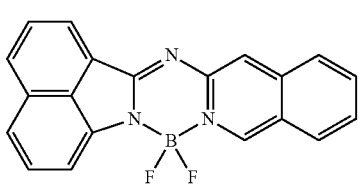
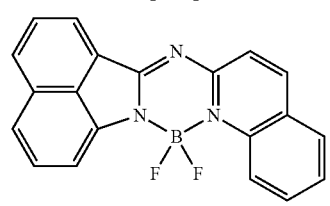
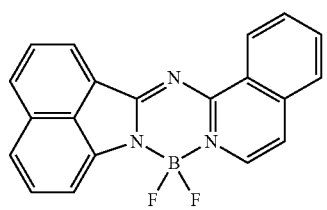
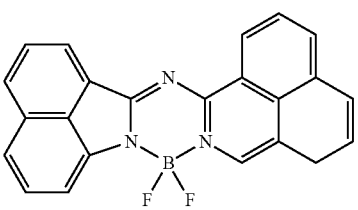
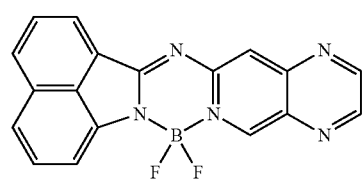
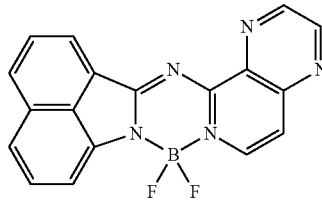
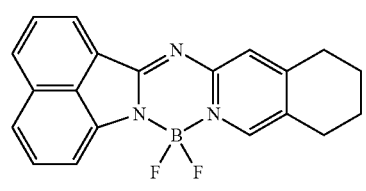
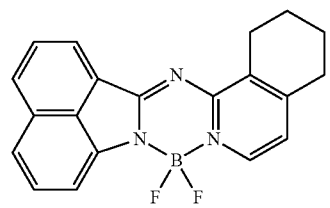
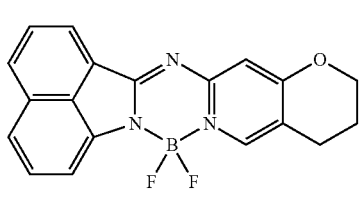
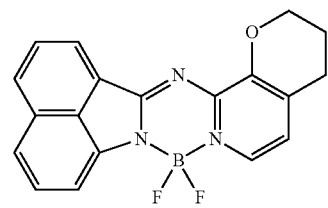
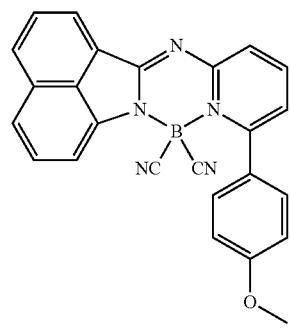
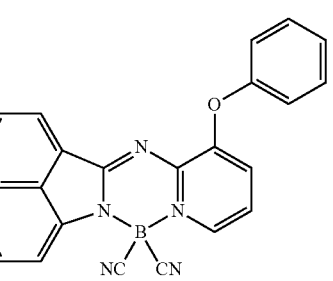
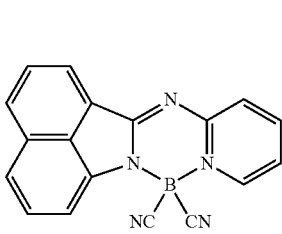

-continued
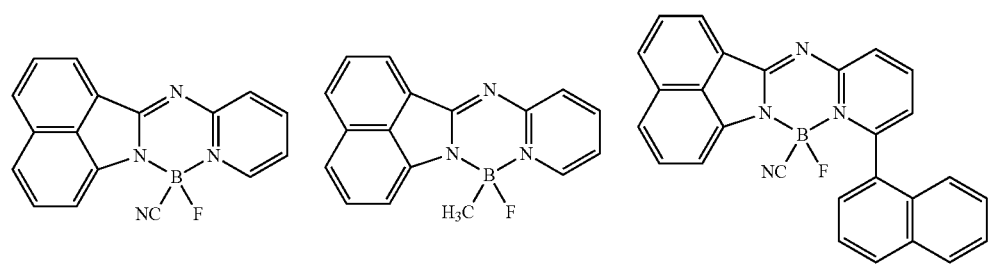
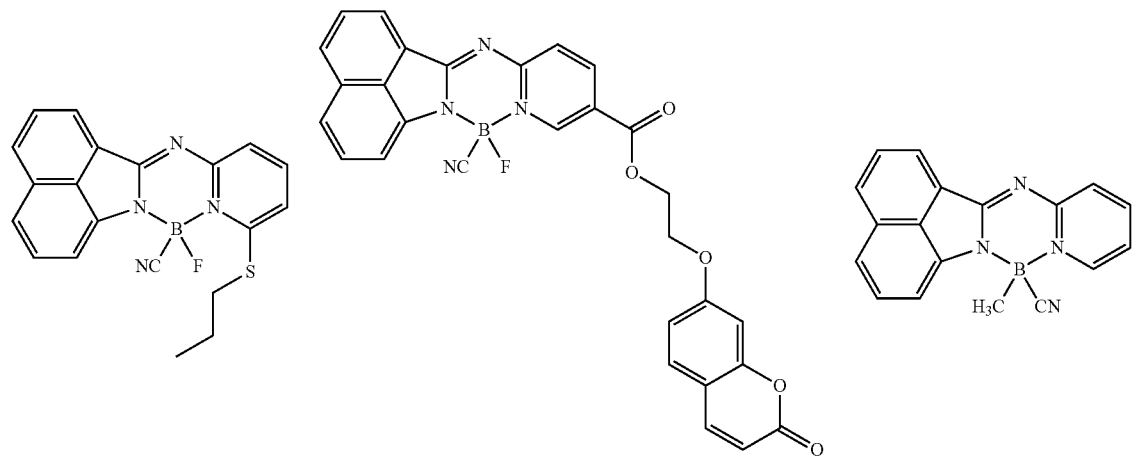
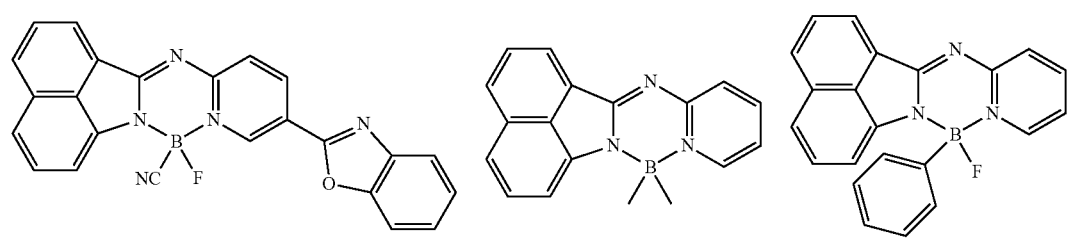
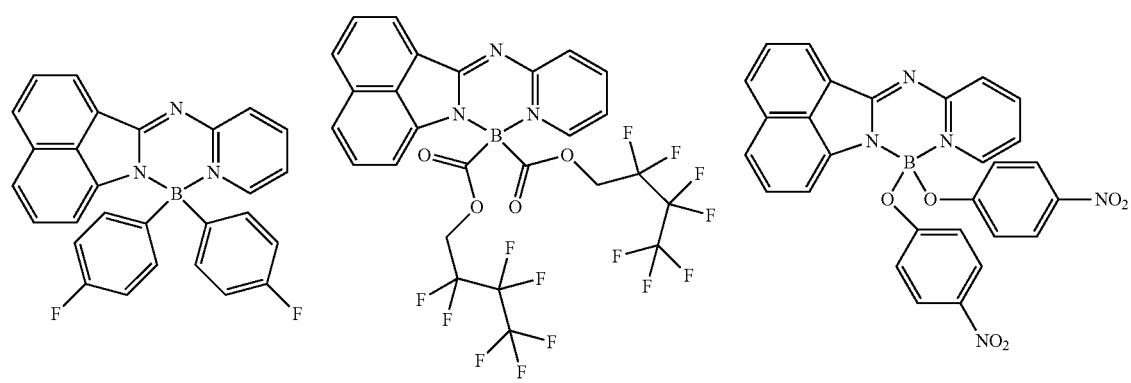
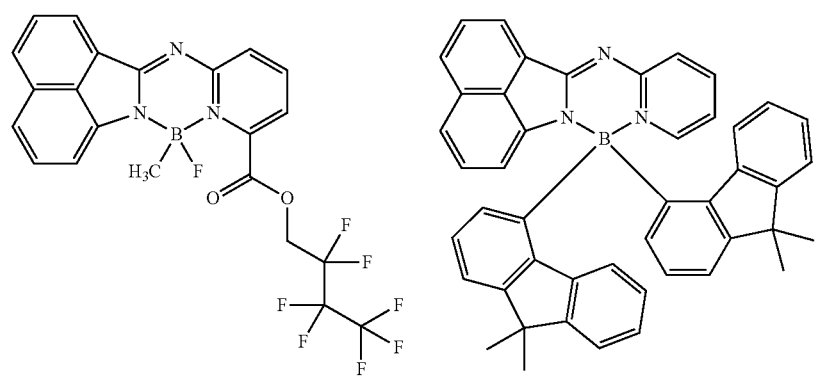

21
-continued
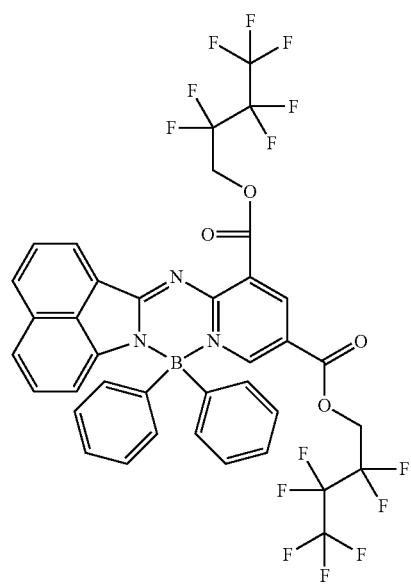 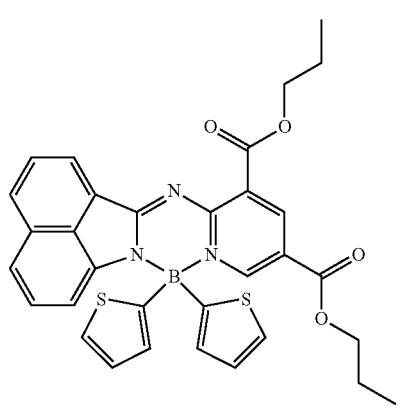 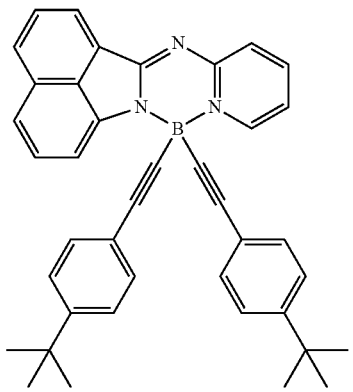
22
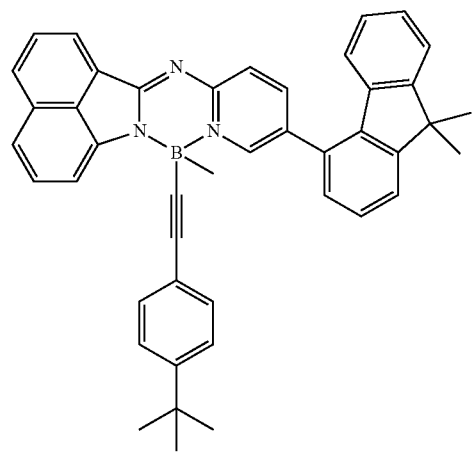 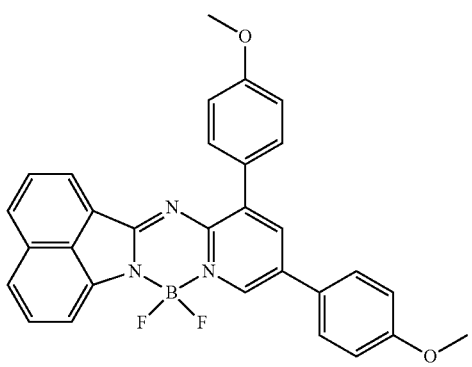
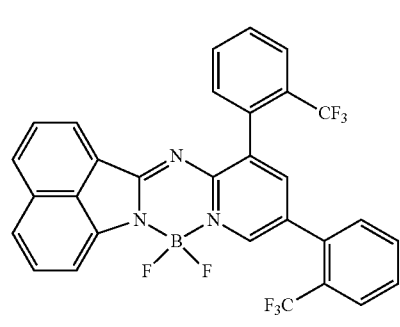 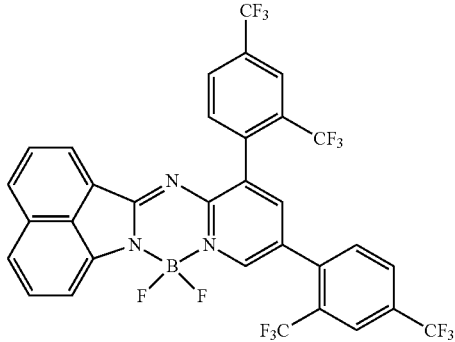

-continued
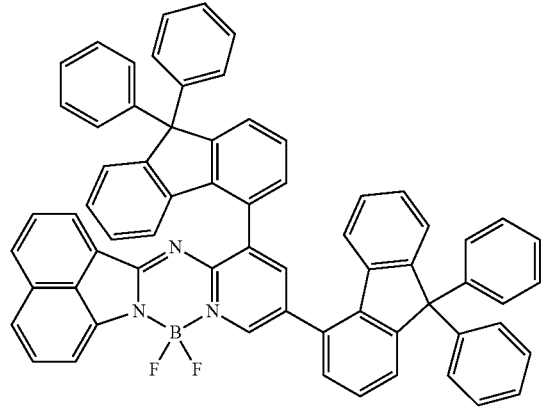
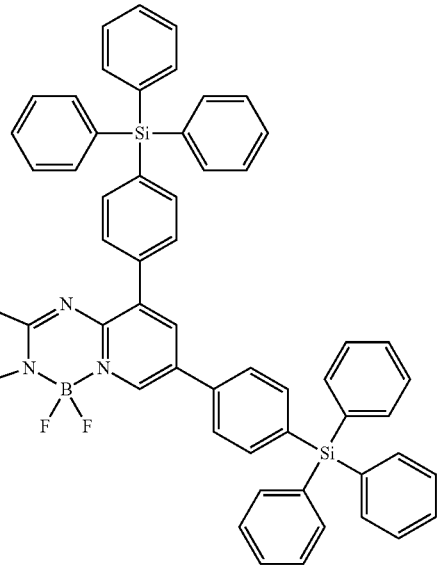
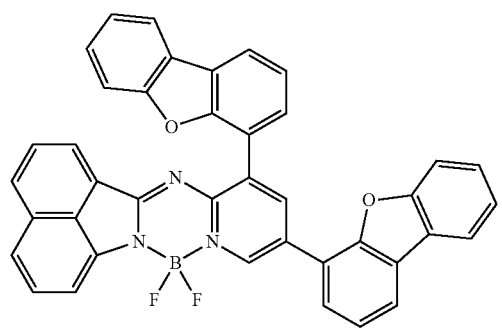
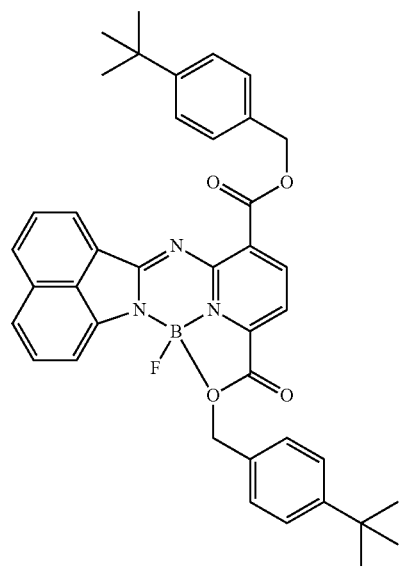
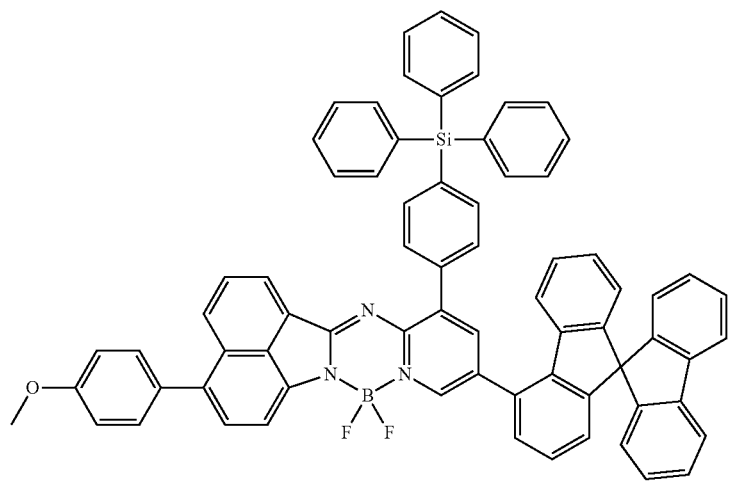

25
26
-continued
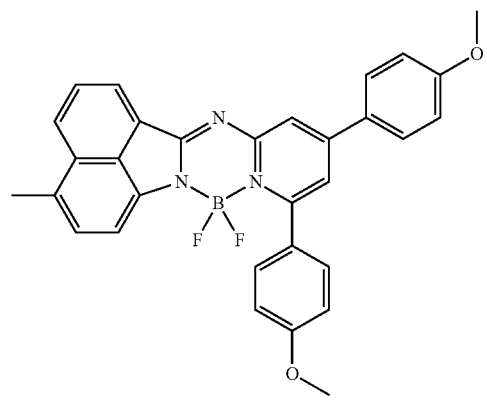
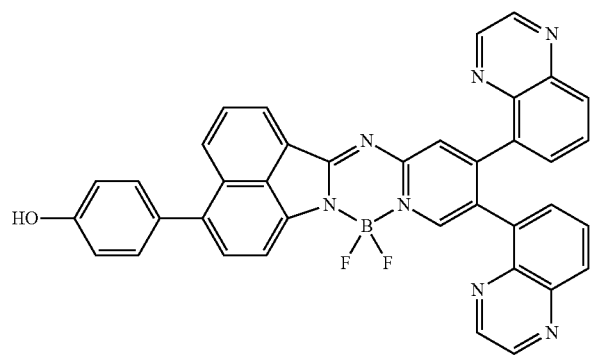
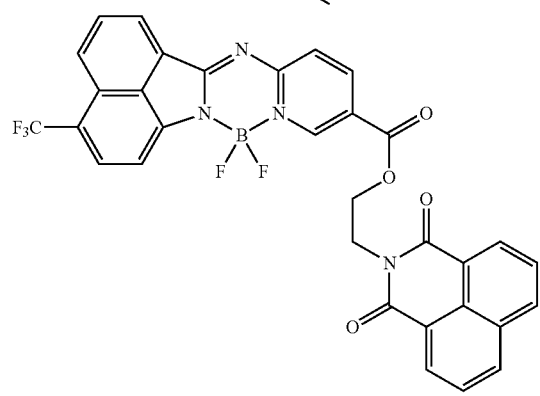
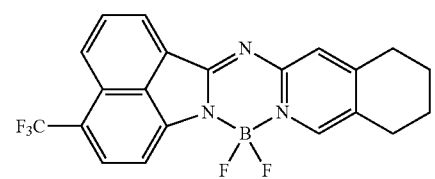
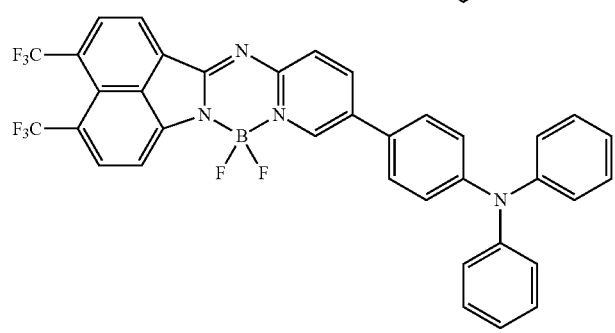
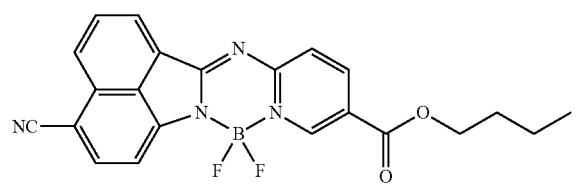
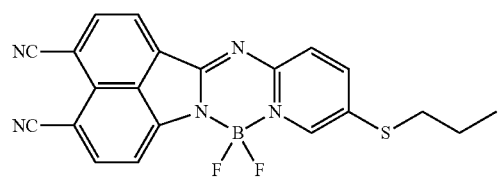
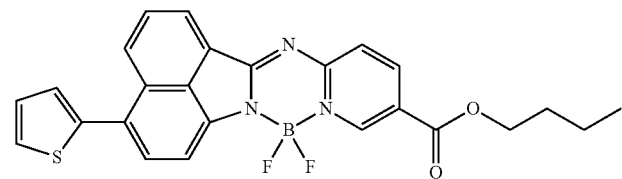
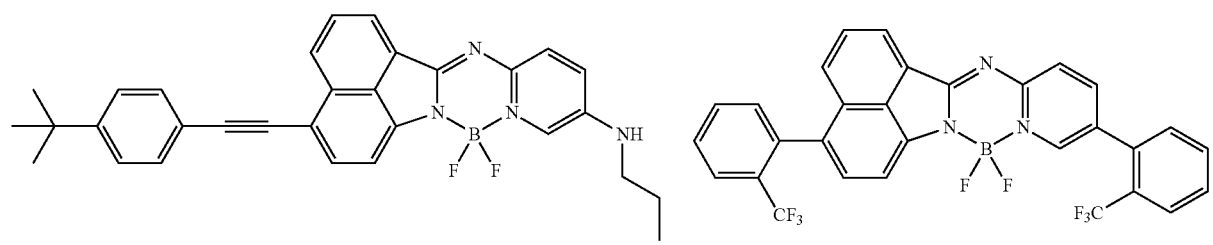
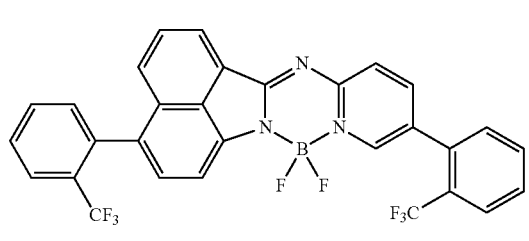

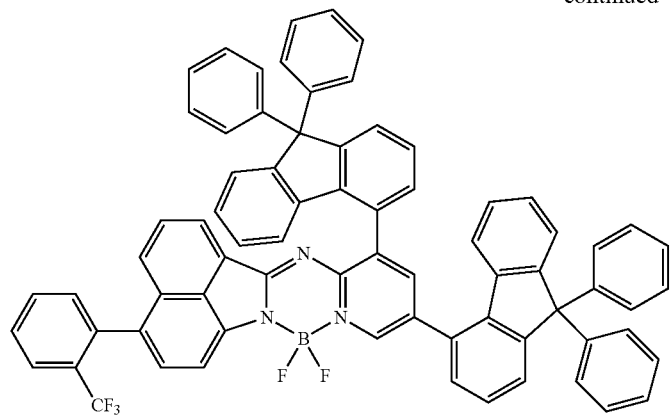
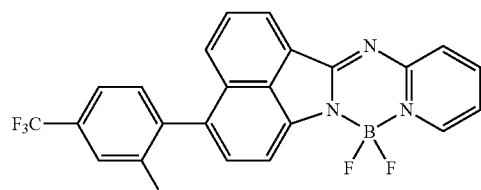
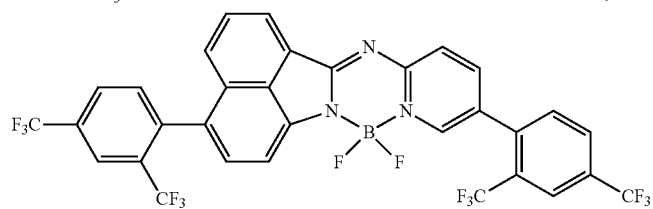
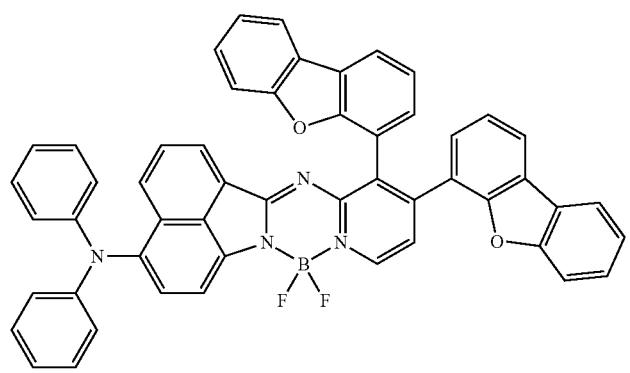
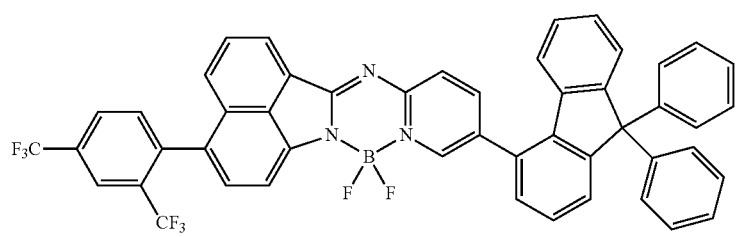
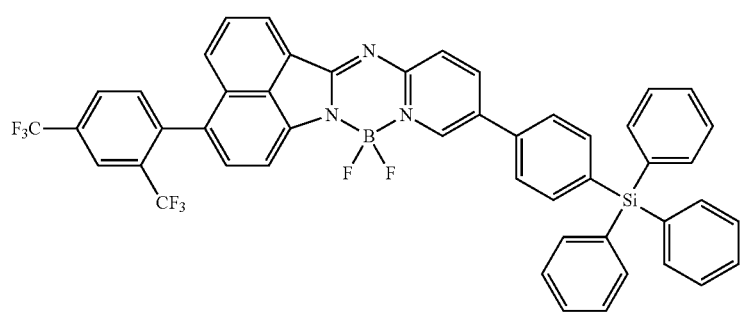

-continued
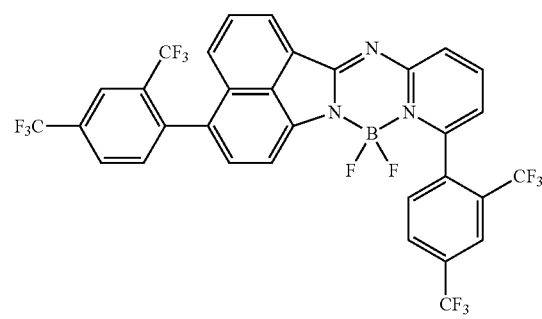
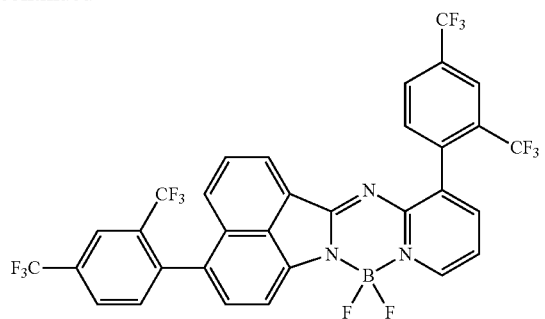
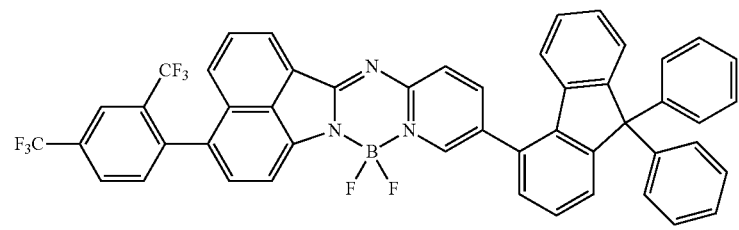
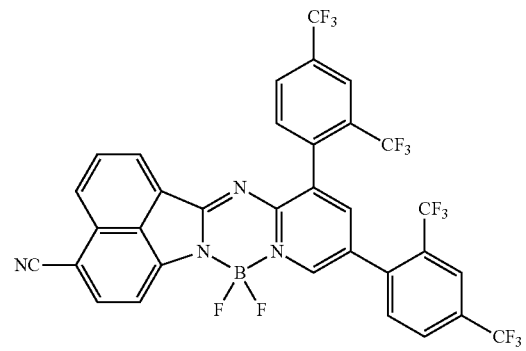
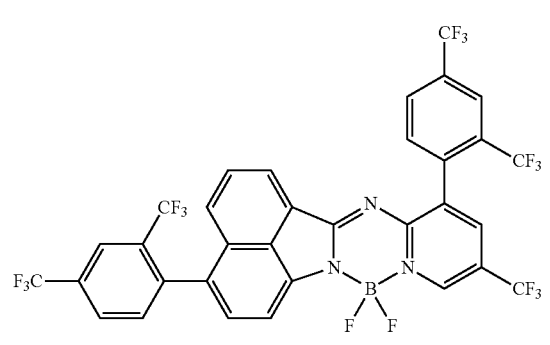
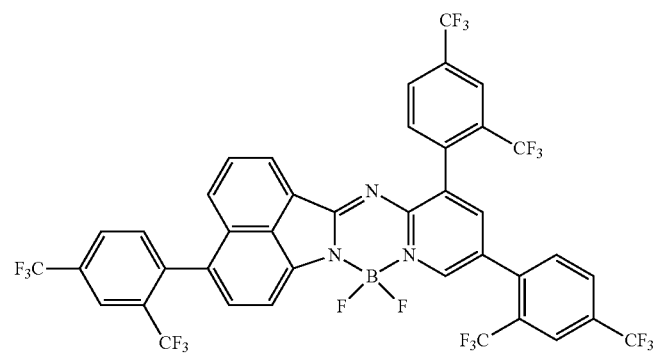
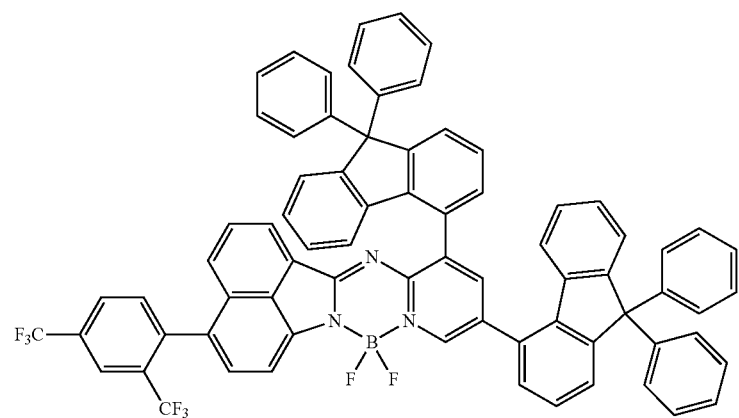

-continued
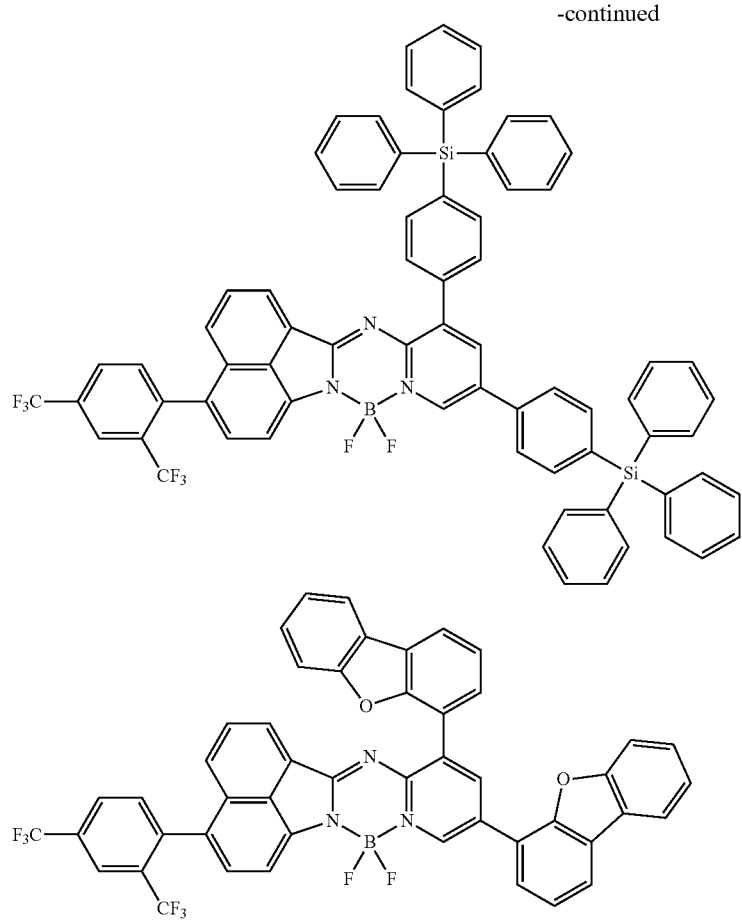
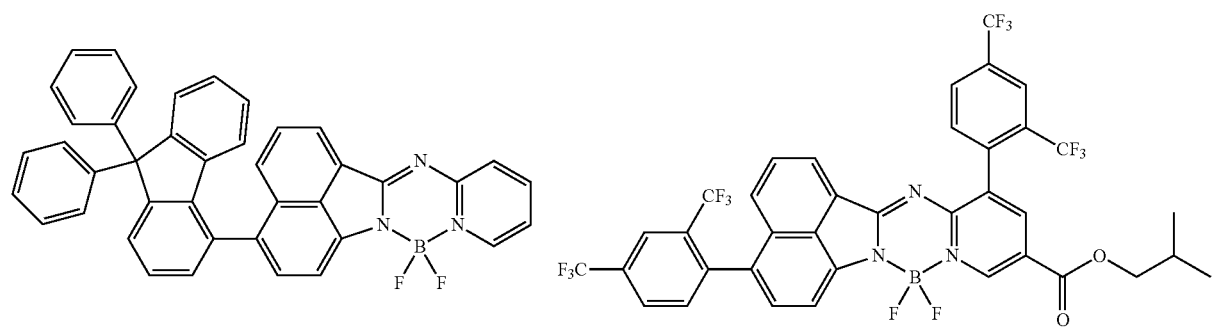
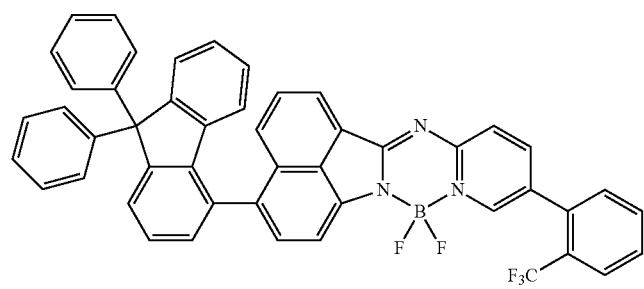

-continued
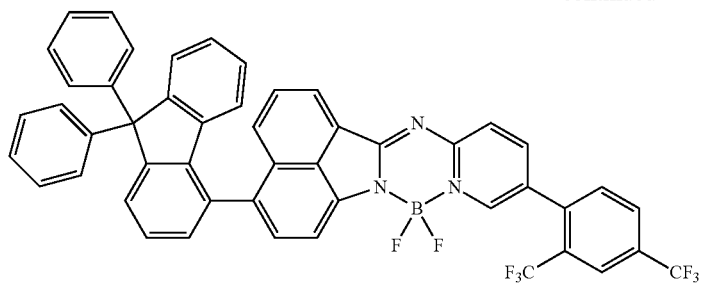
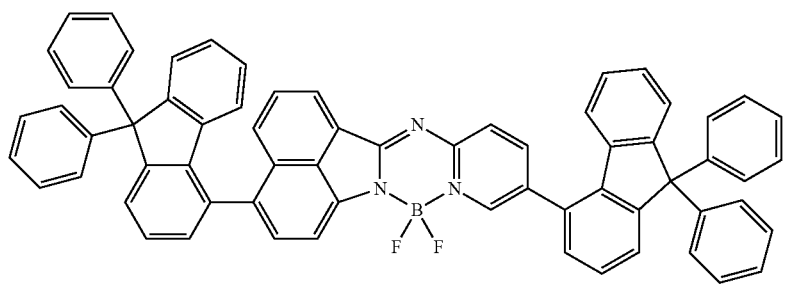
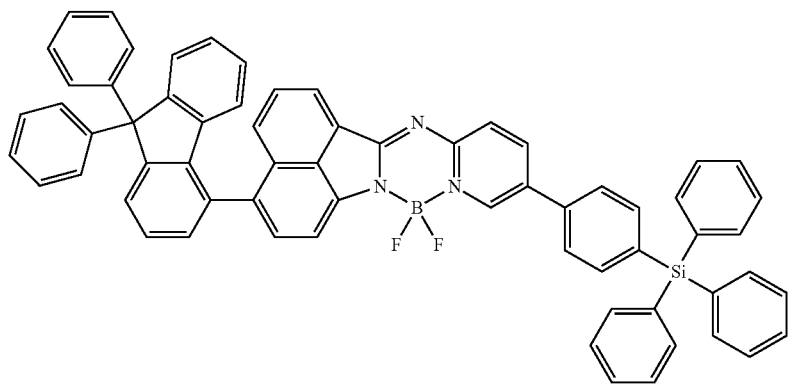
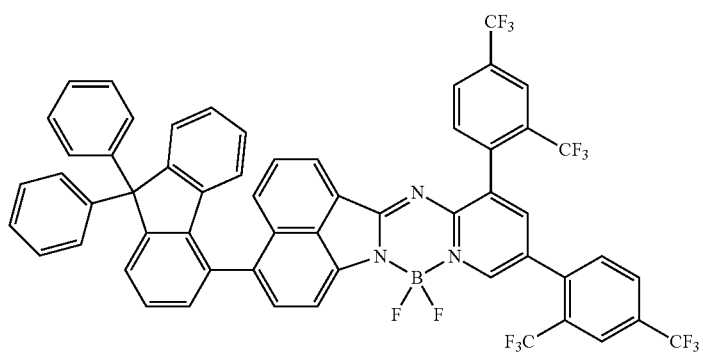

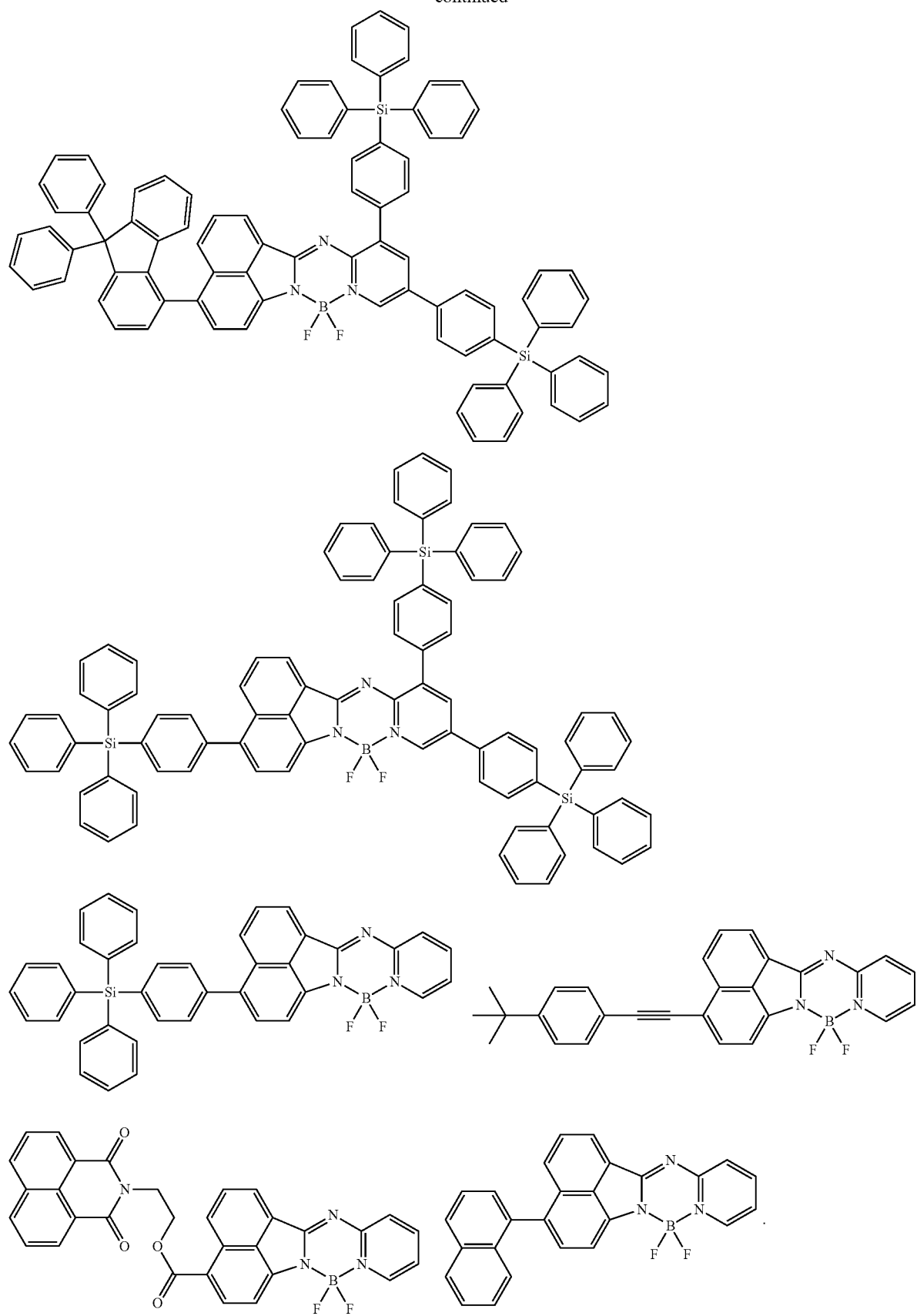

In one embodiment of the present specification, the compound represented by Chemical Formula 2 is represented by any one of the following compounds.
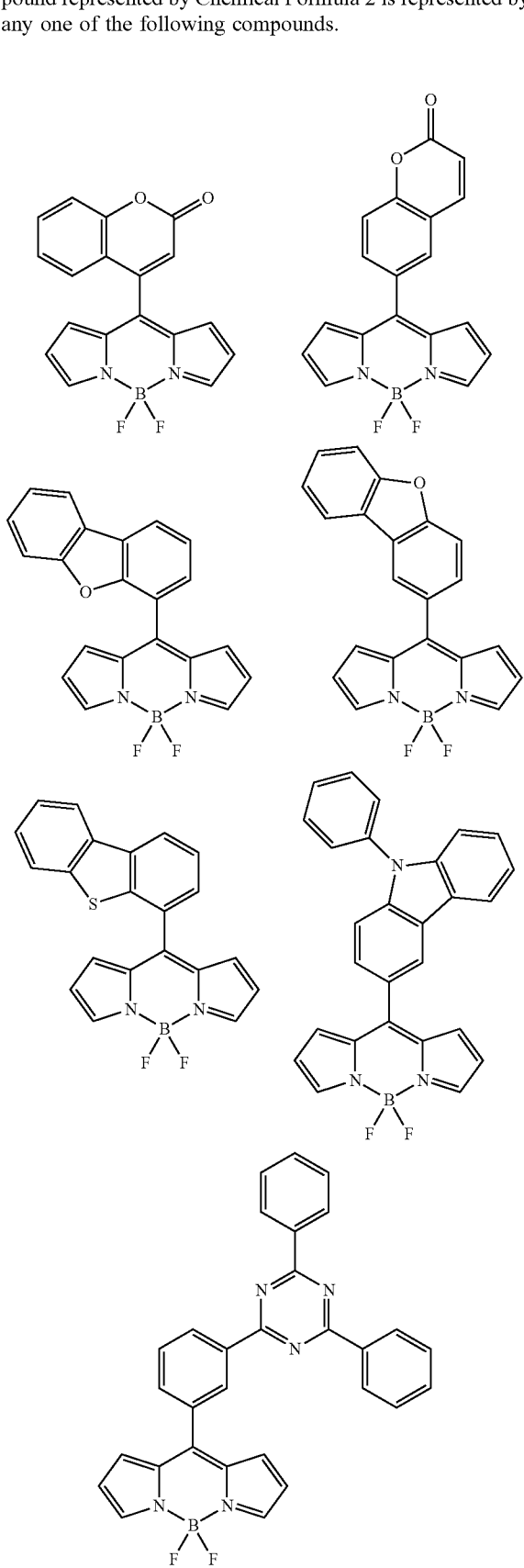
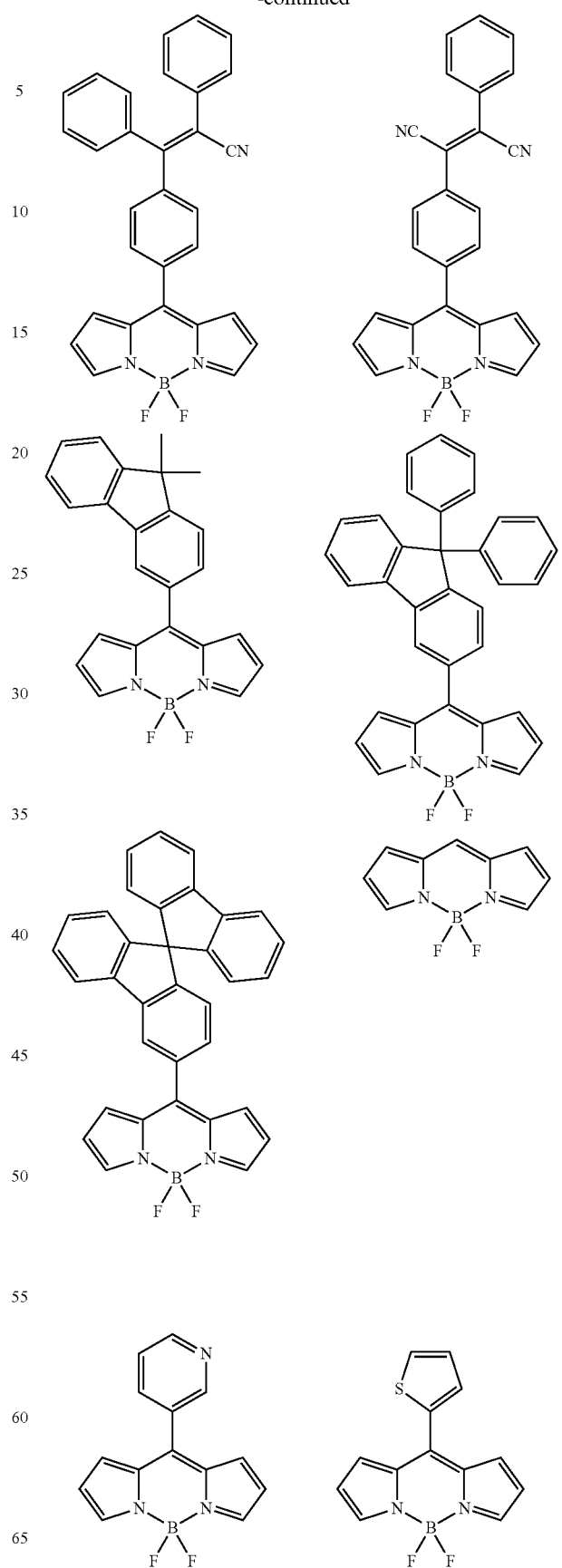

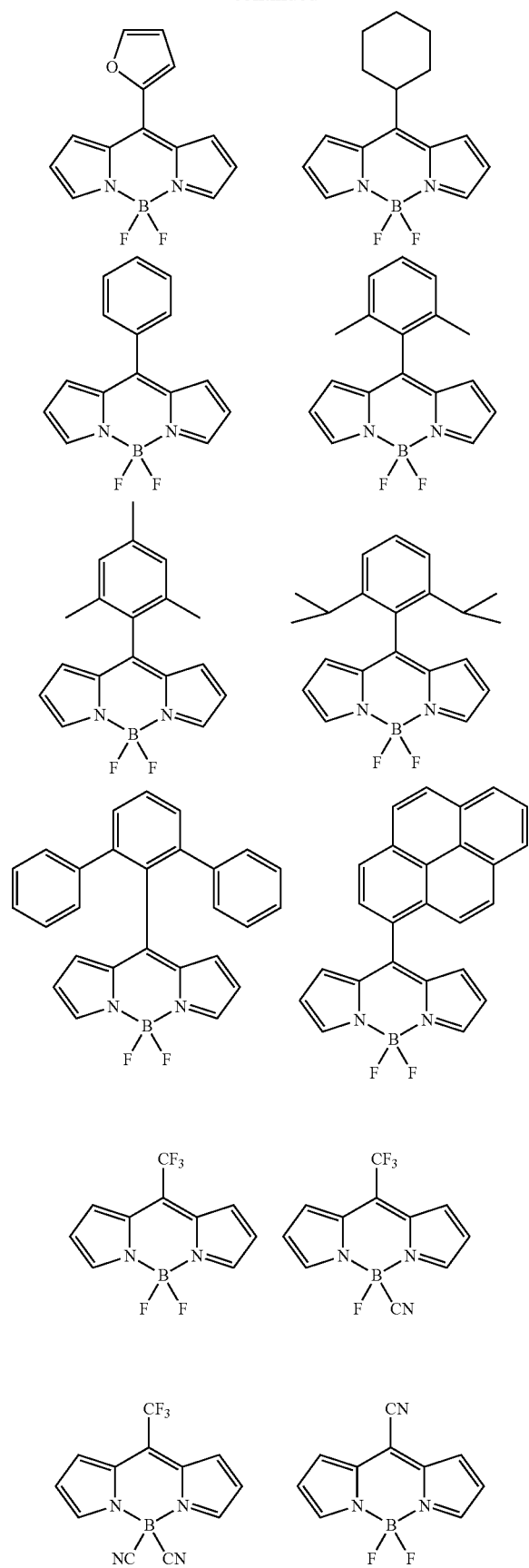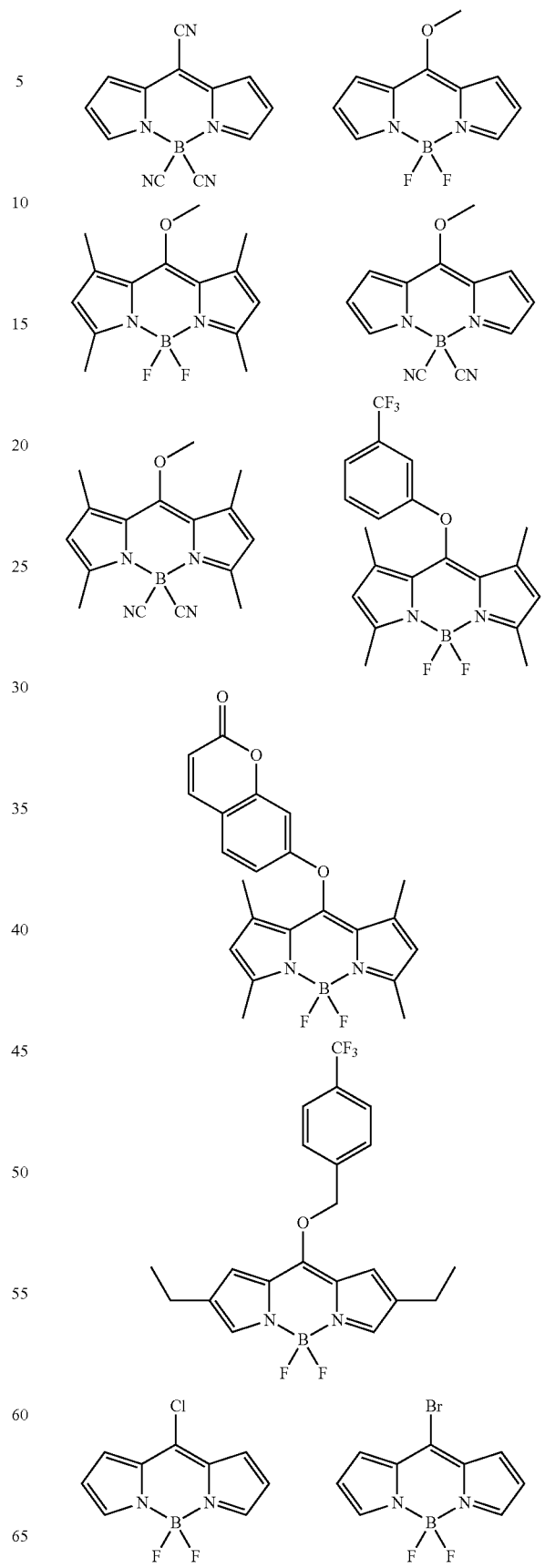

-continued
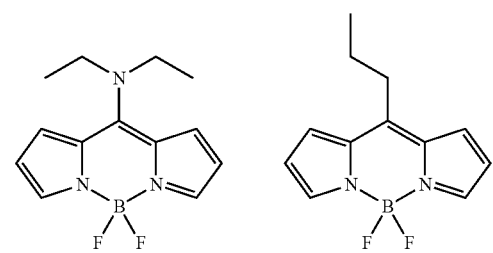
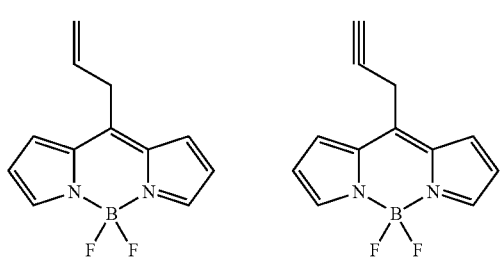
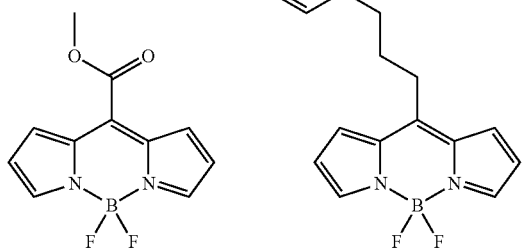
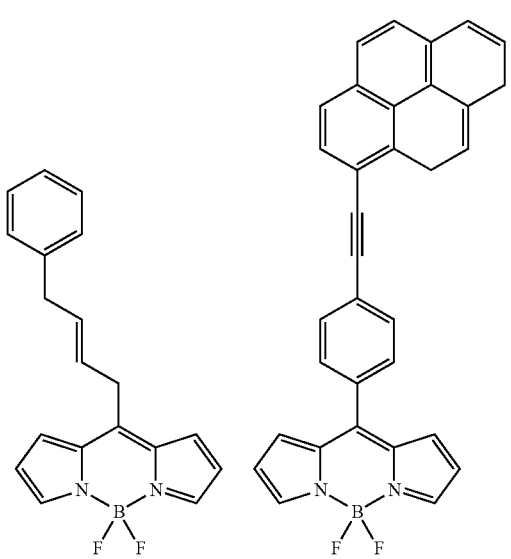
-continued
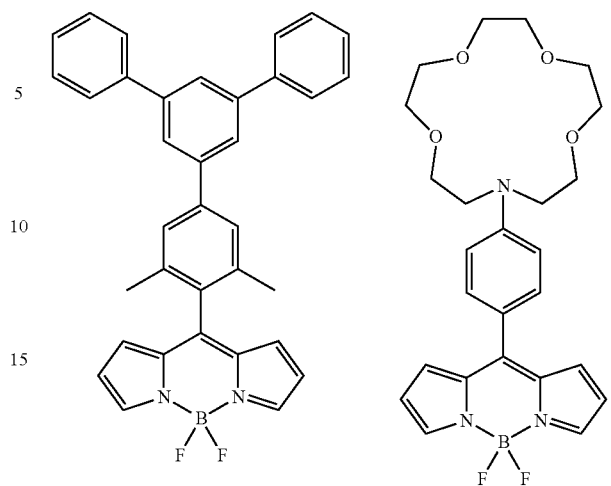
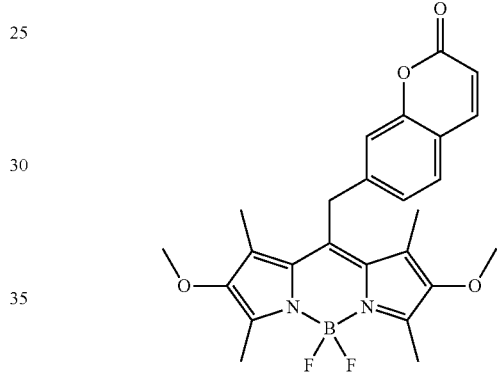
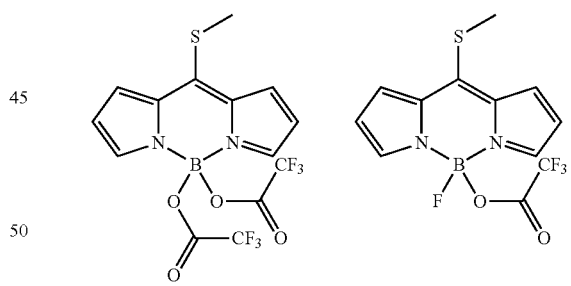
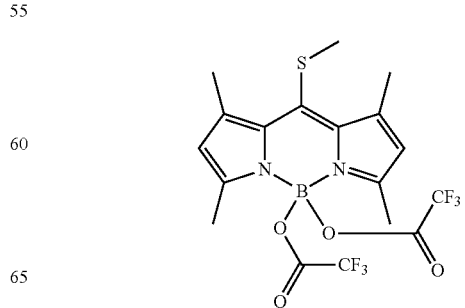

-continued
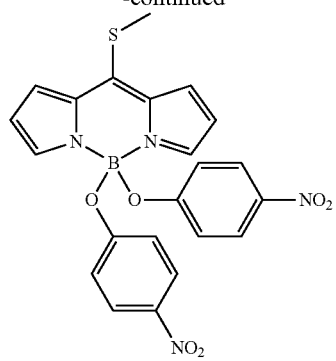
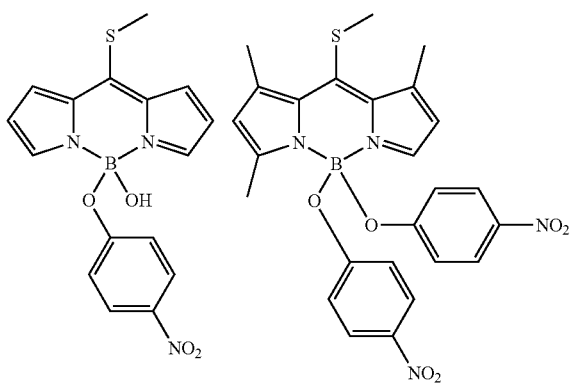
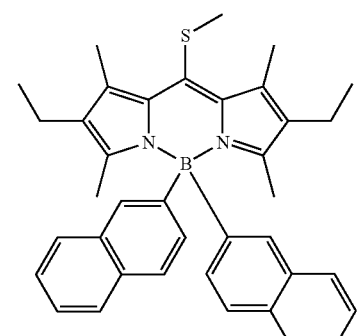
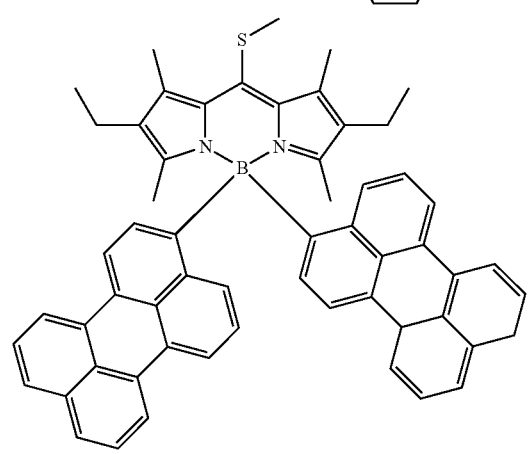
-continued
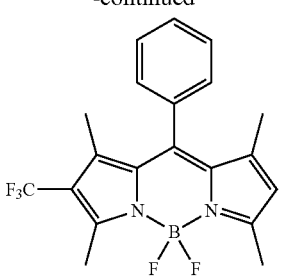
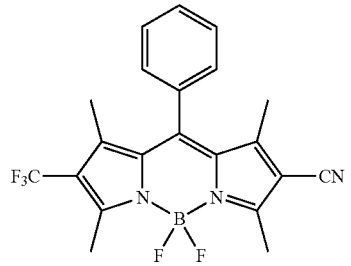
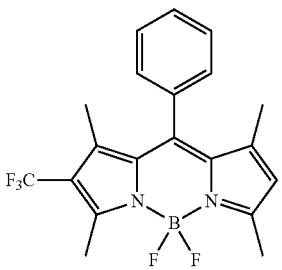
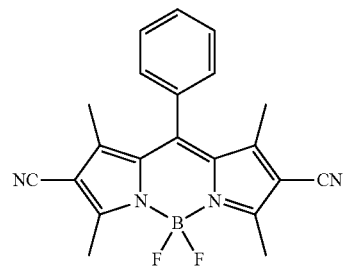
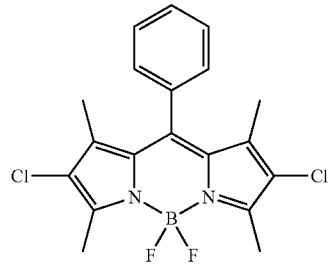
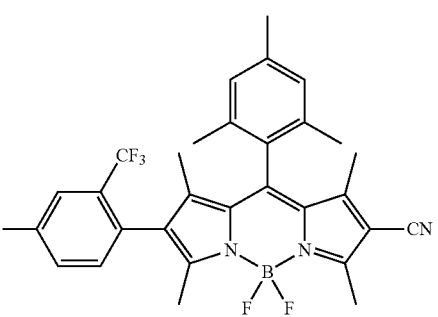

-continued
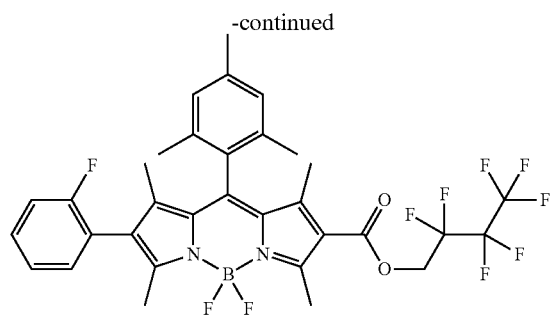
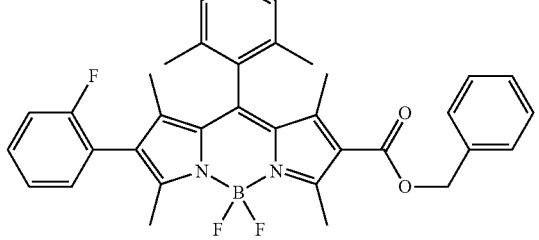
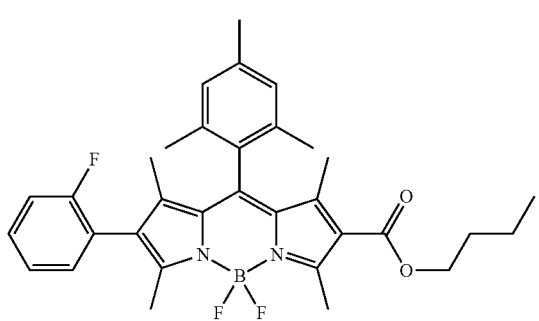
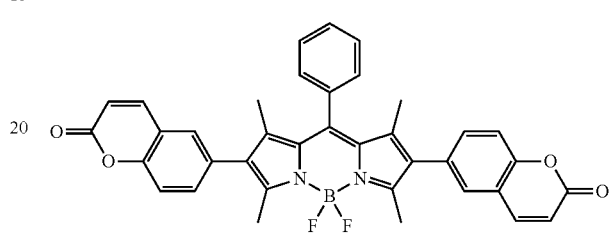
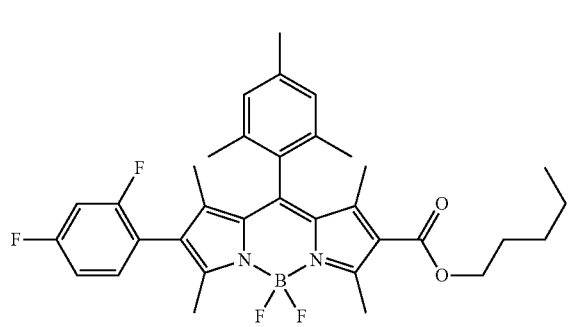
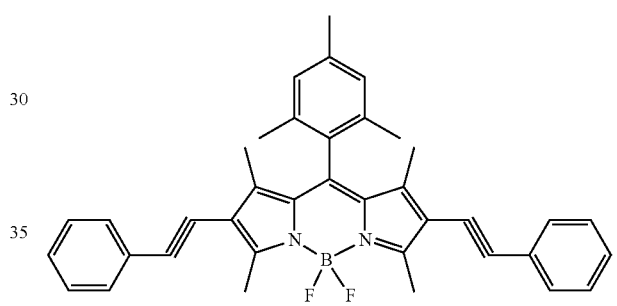
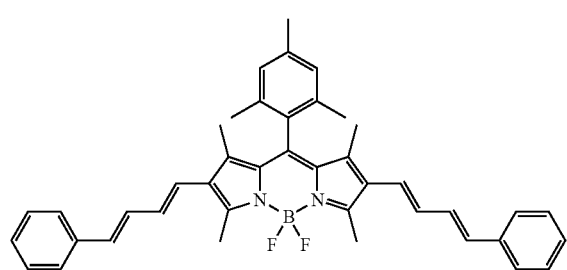
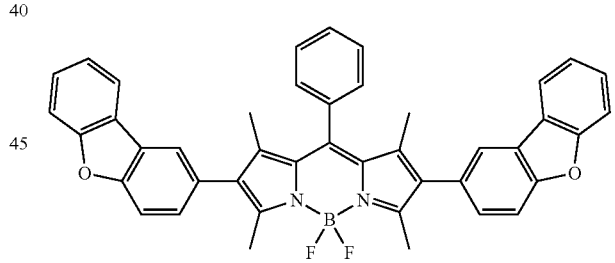
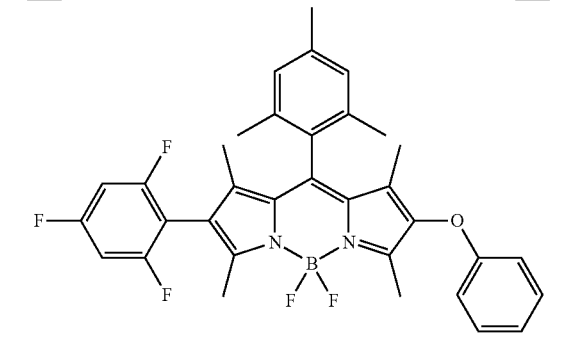
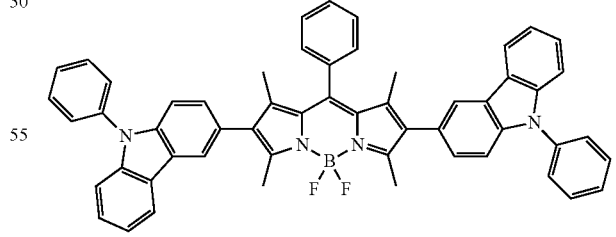
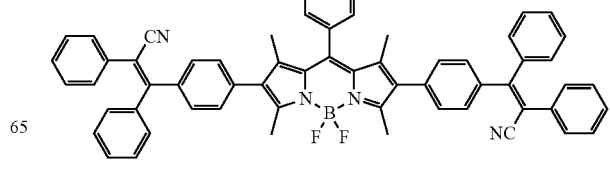

47
-continued
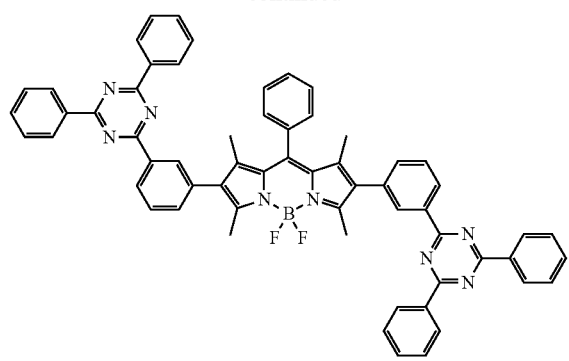
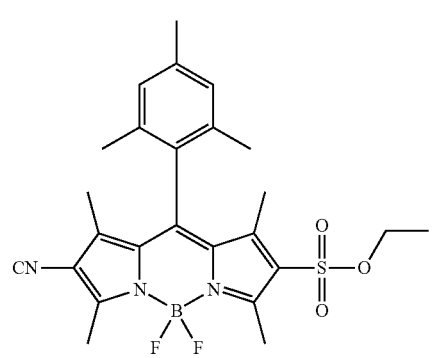
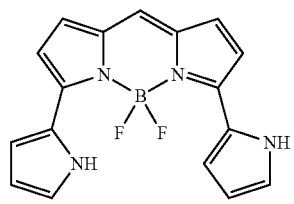
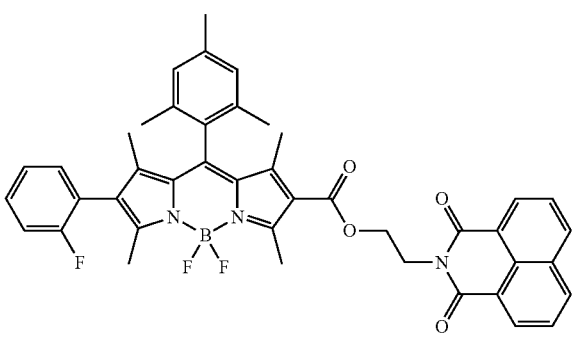
48
-continued
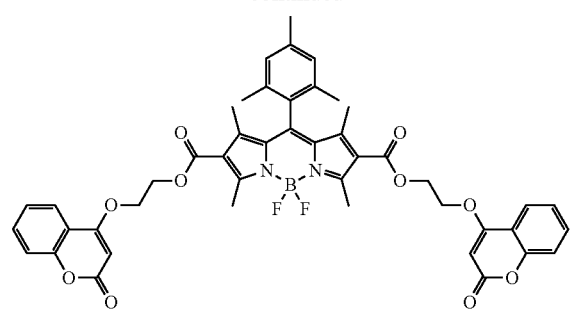
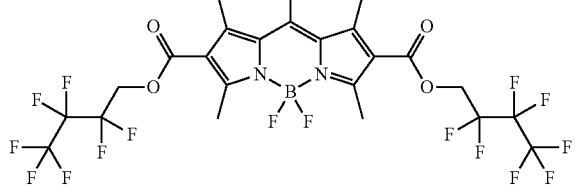
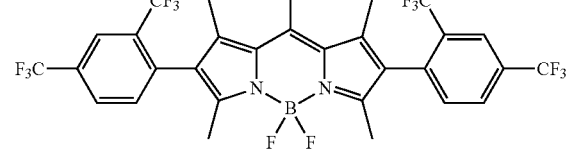
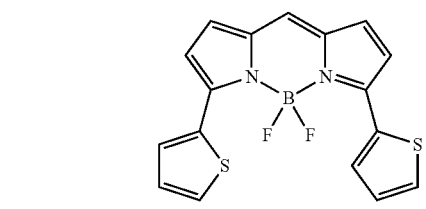
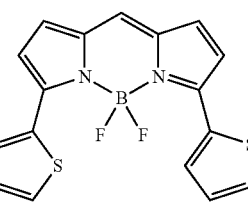

49
-continued
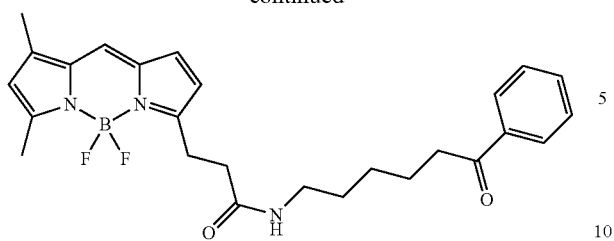
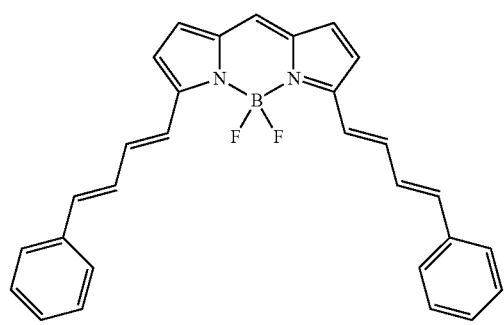
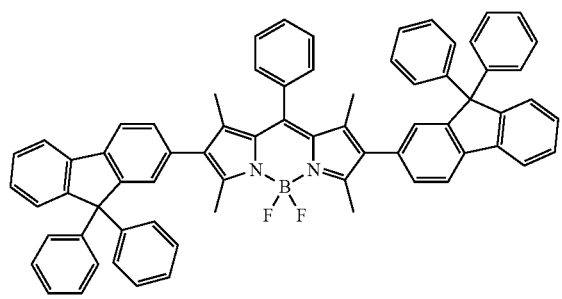
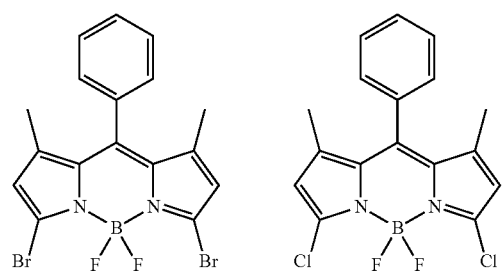
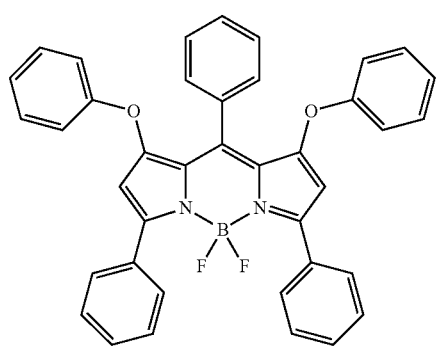
50
-continued
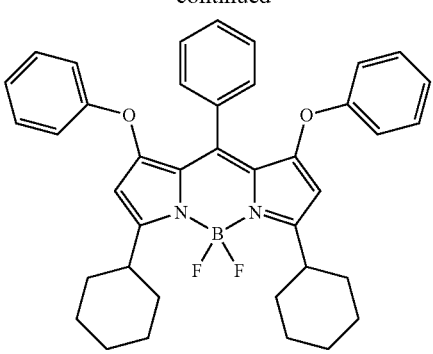
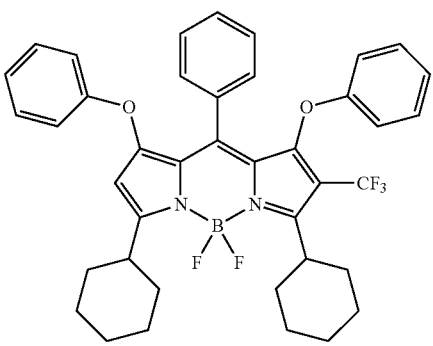
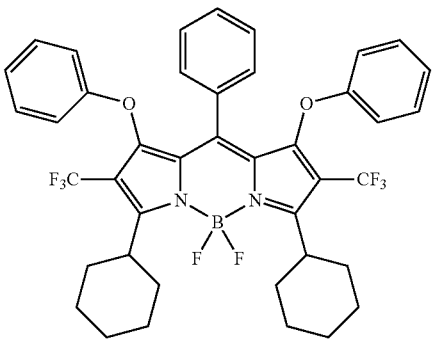
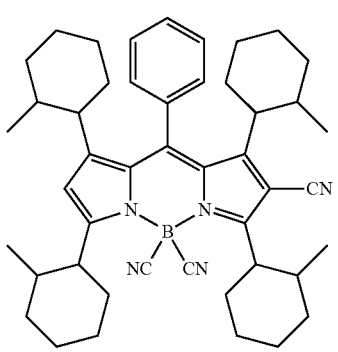
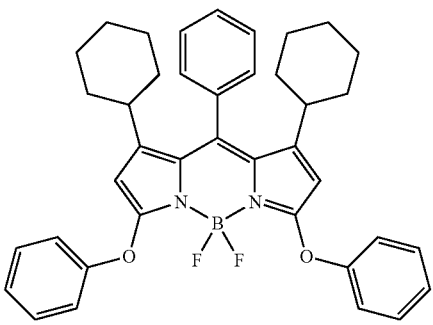

51
-continued
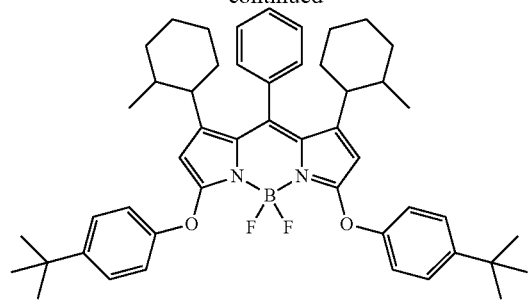
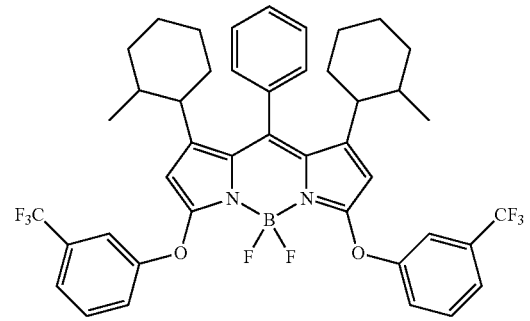
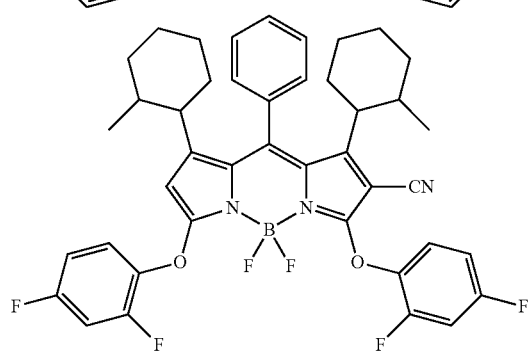
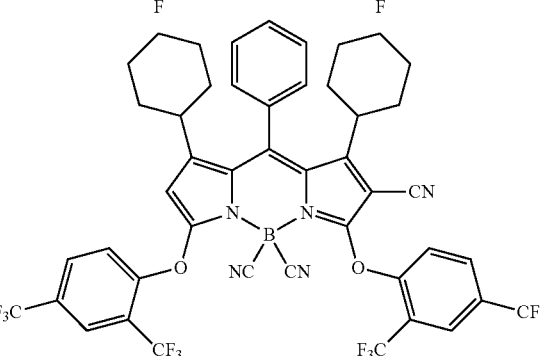
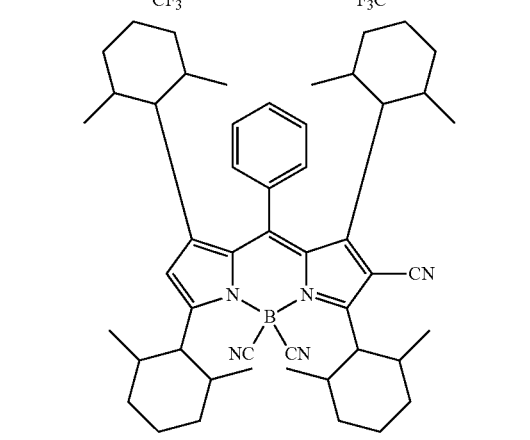
52
-continued
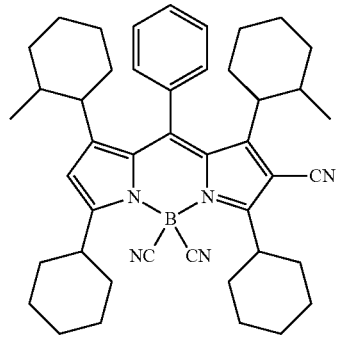
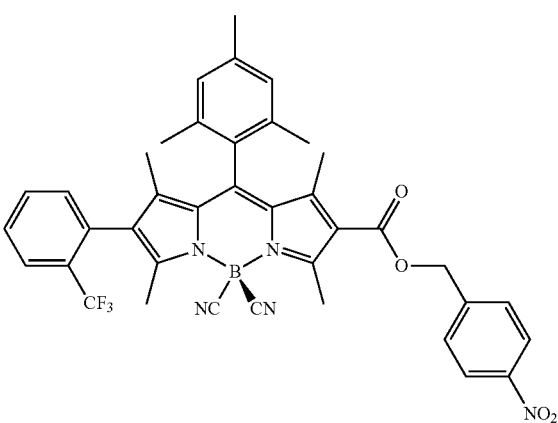
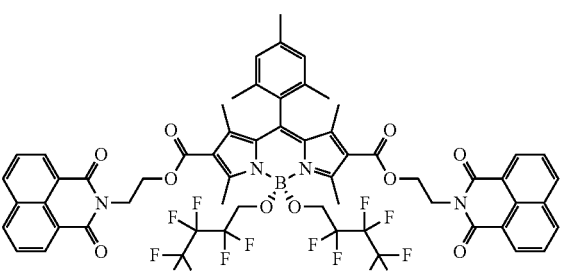
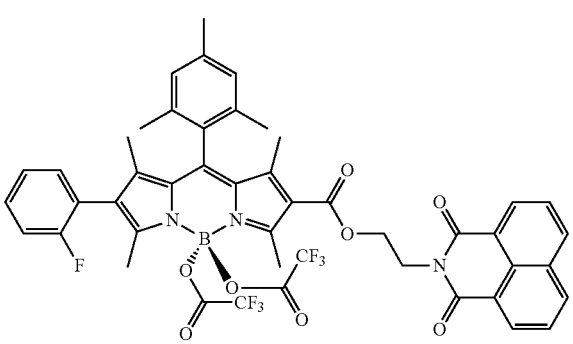

53
-continued
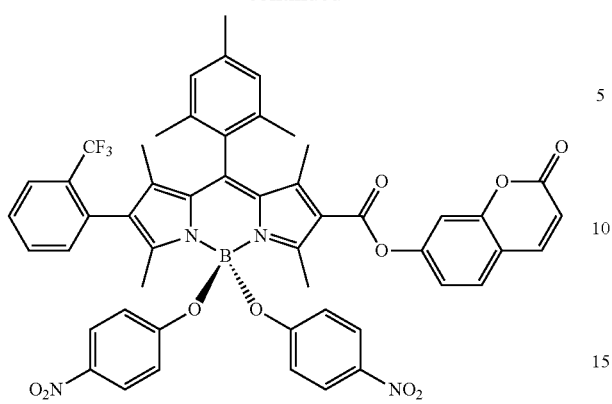
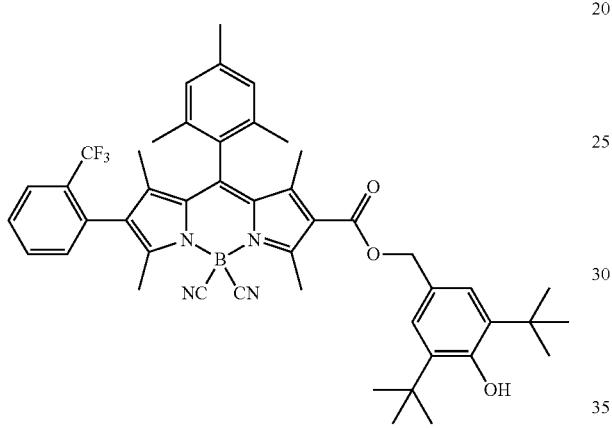
54
-continued
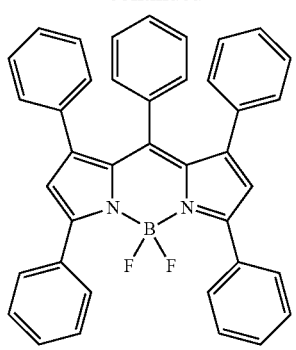
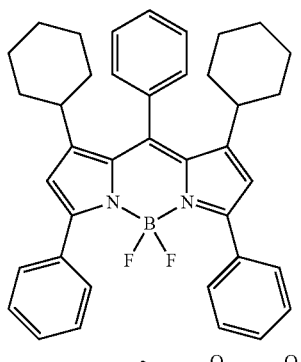
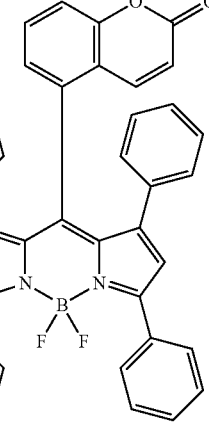
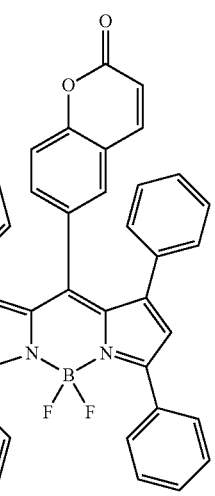

55
-continued
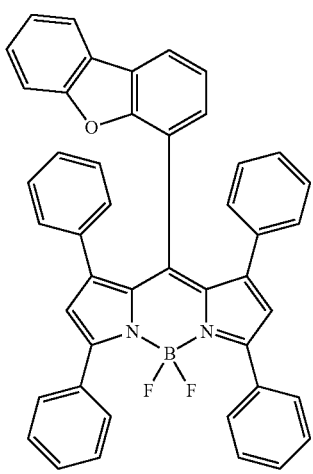
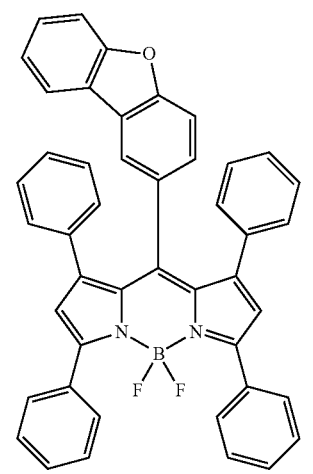
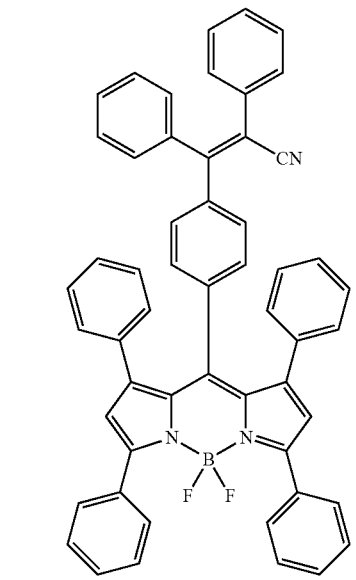
56
-continued
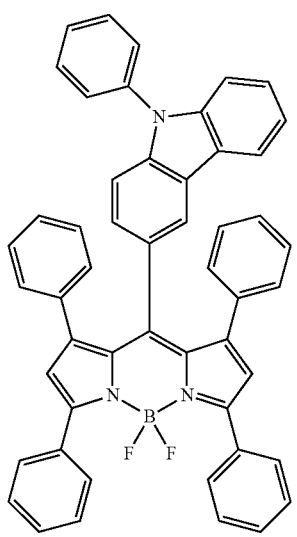
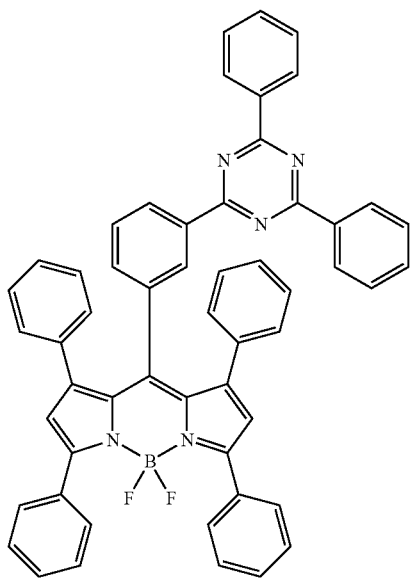
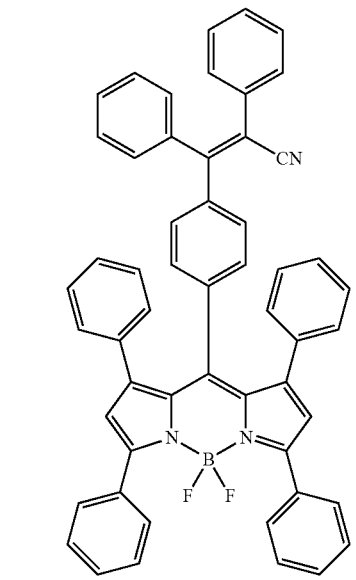

-continued
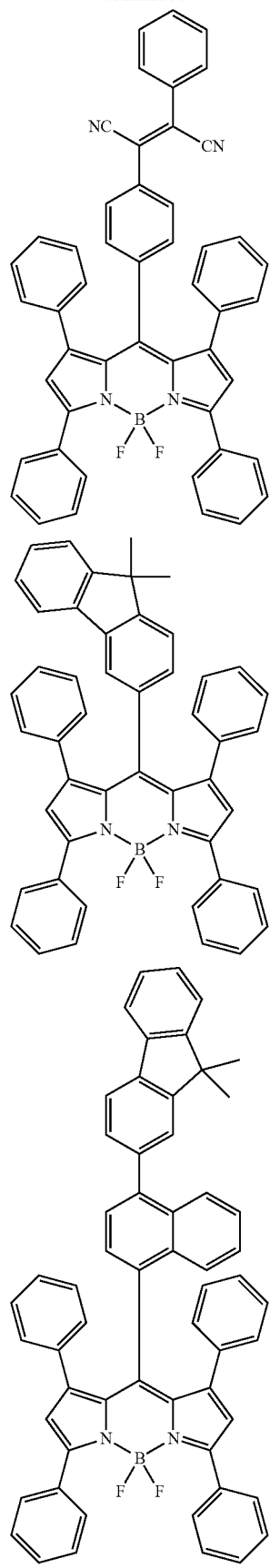
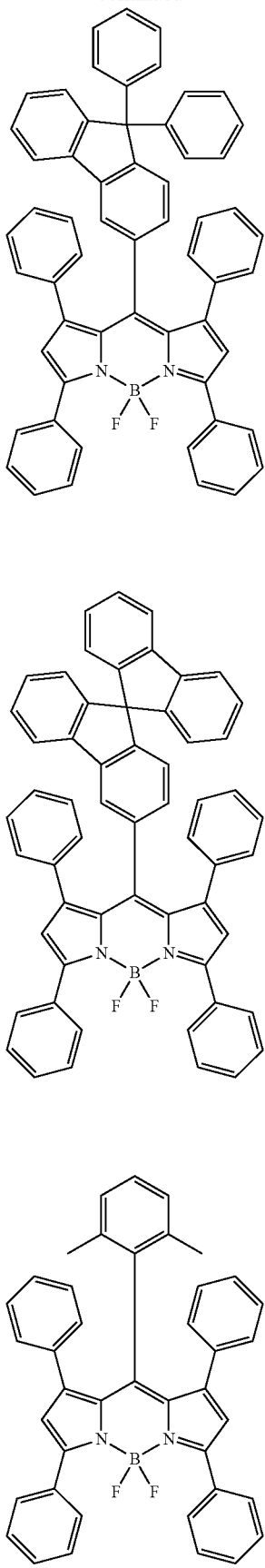

59
-continued
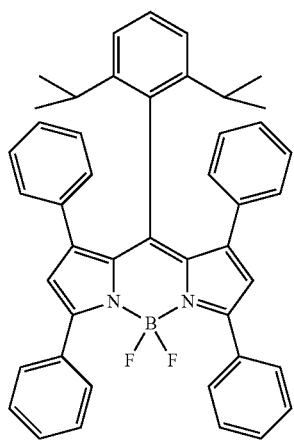
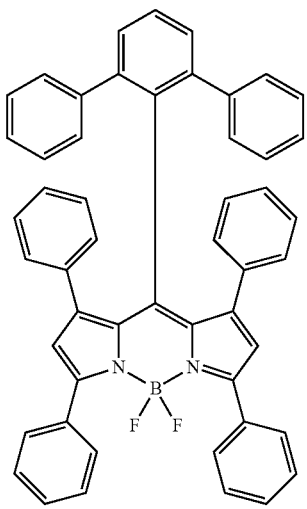
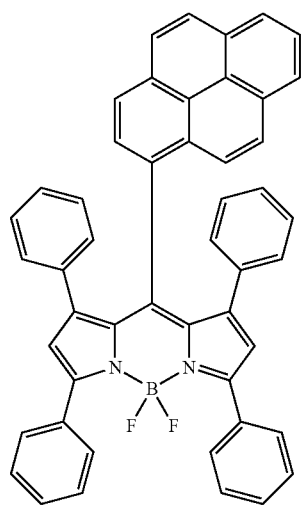
60
-continued
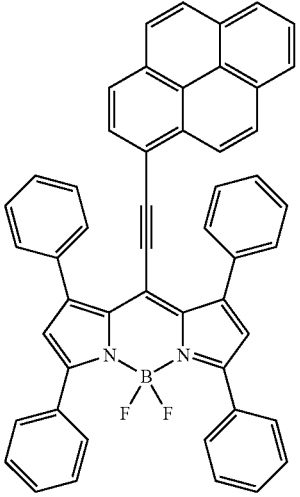
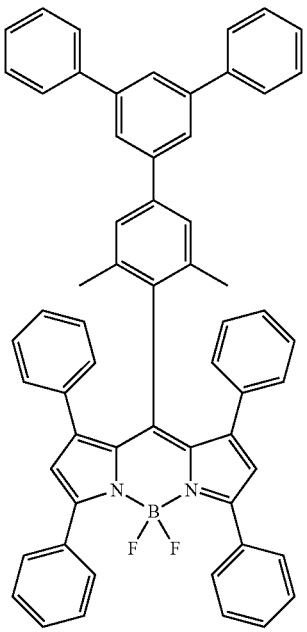
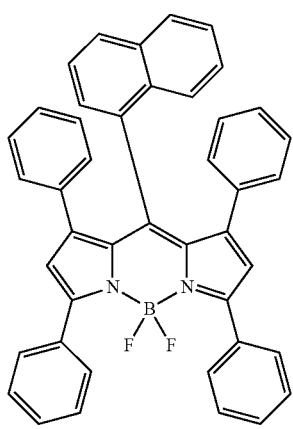

-continued
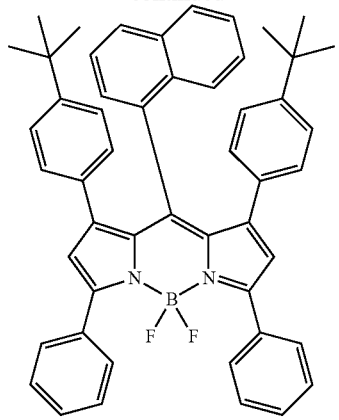
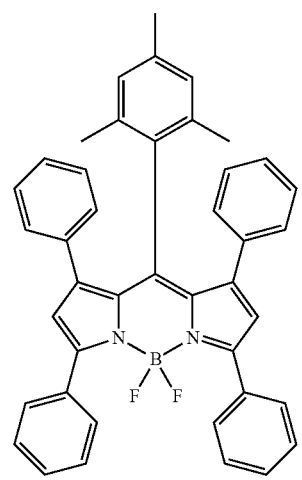
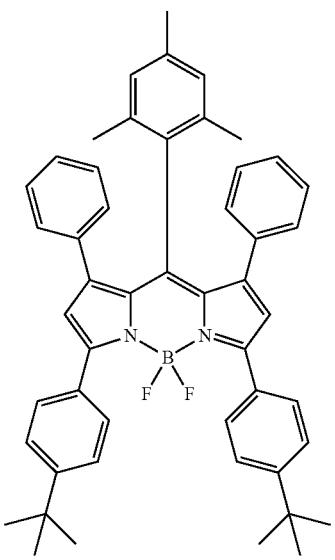
-continued
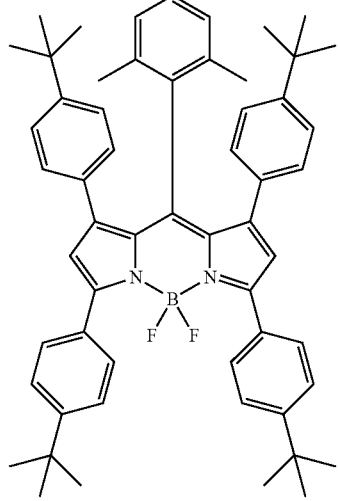
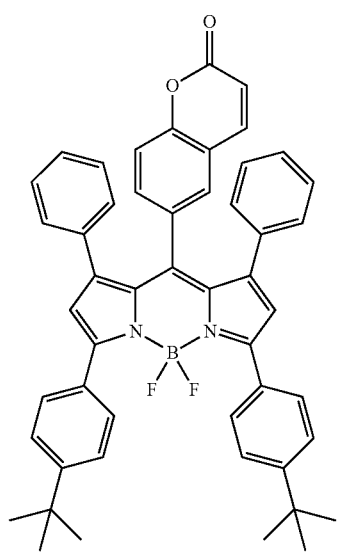
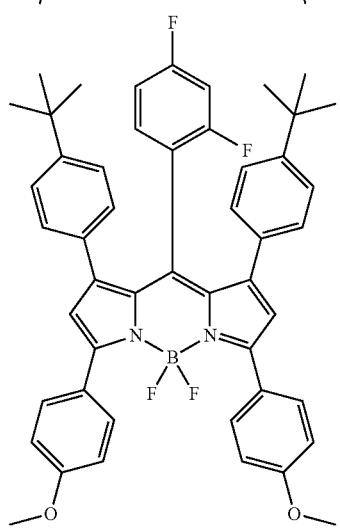

63
-continued
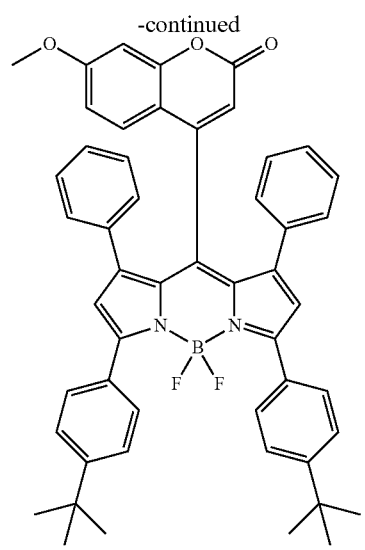
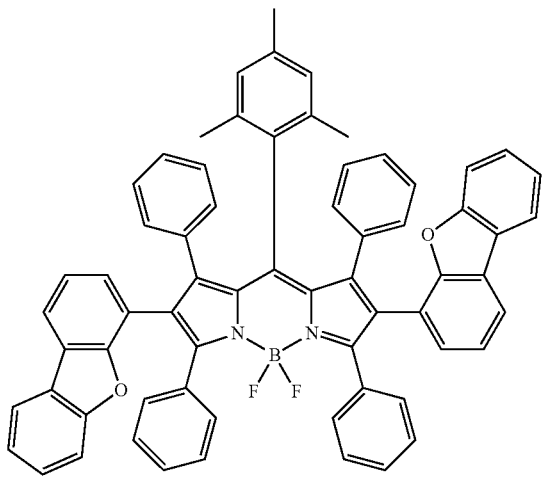
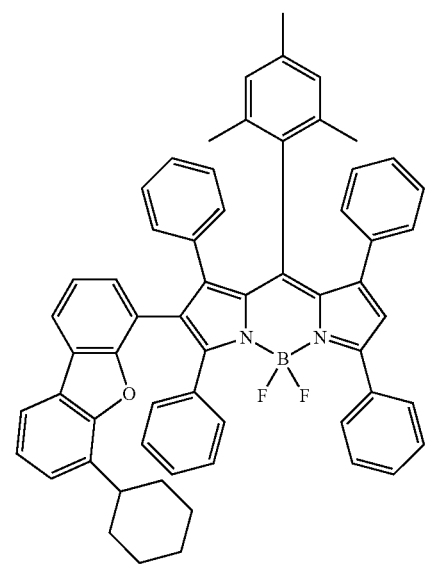
64
-continued
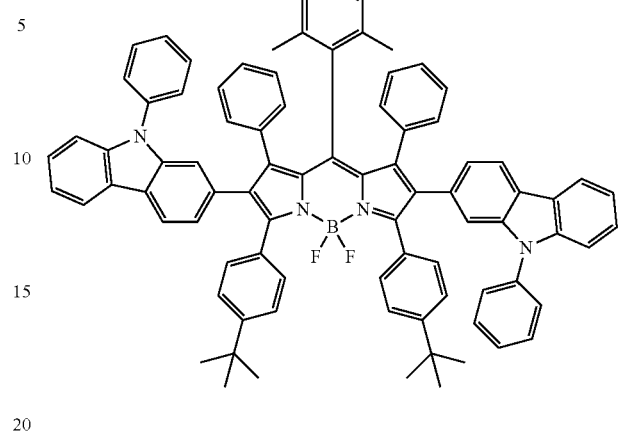
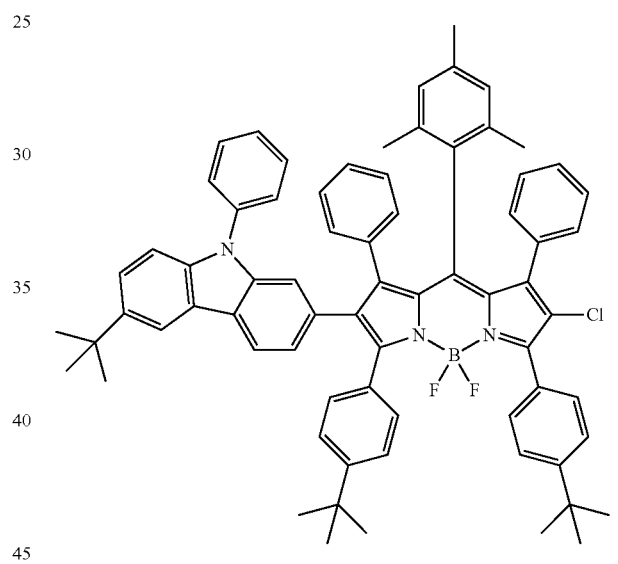
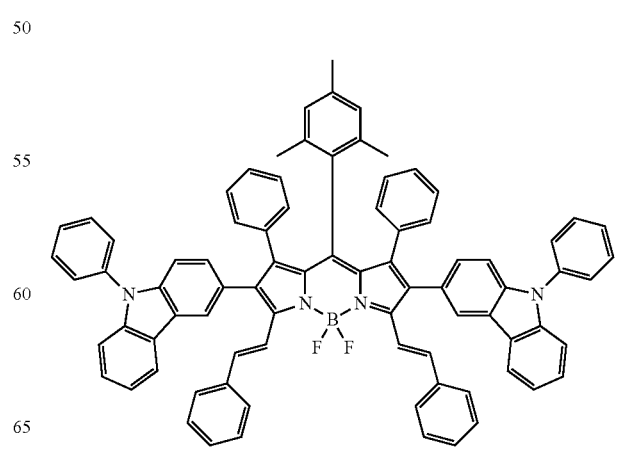

-continued
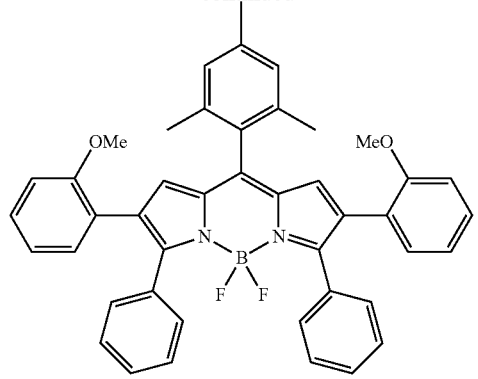
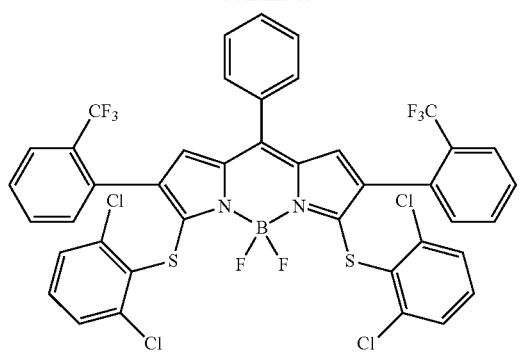
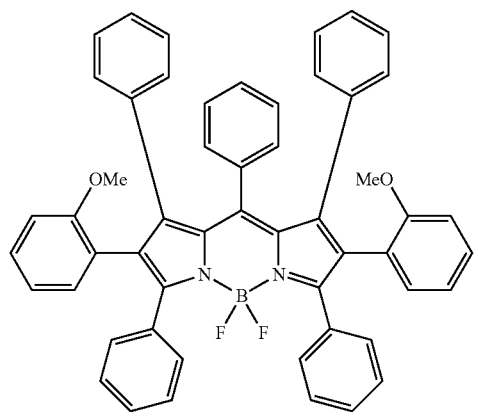
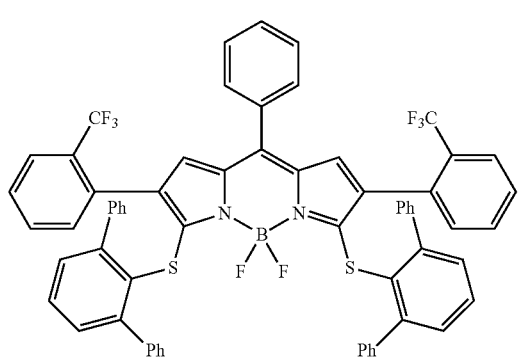
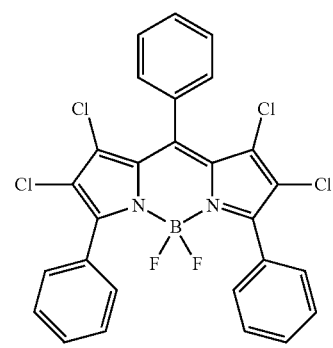
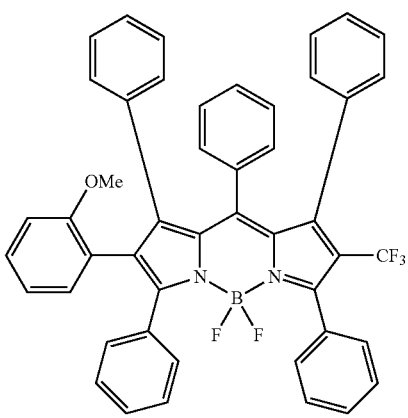
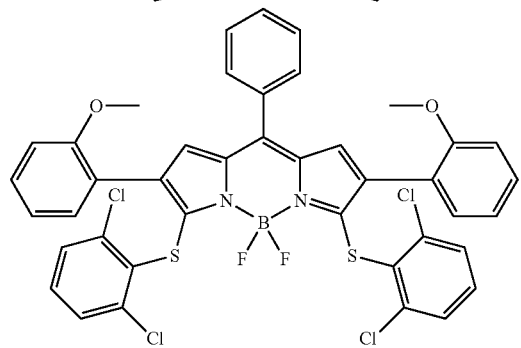
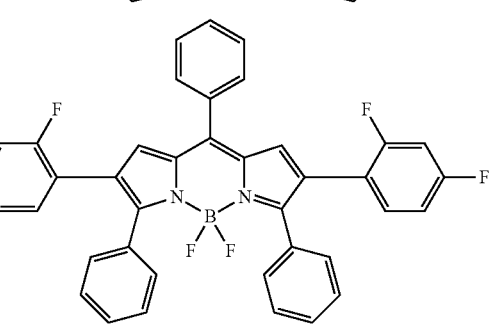

67
-continued
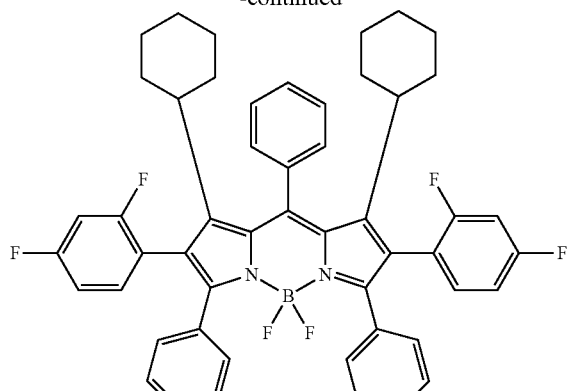
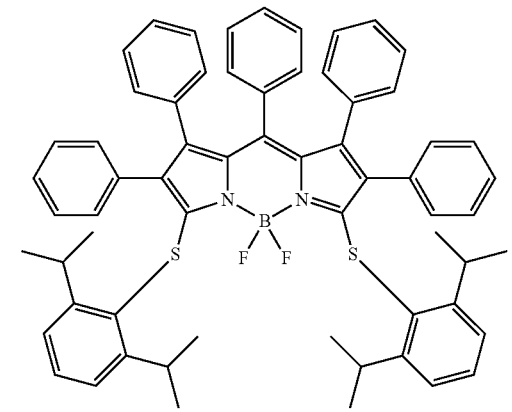
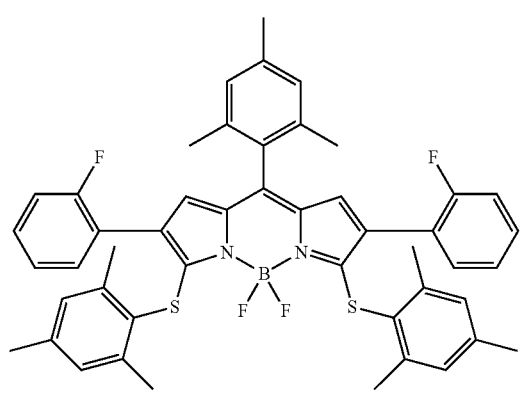
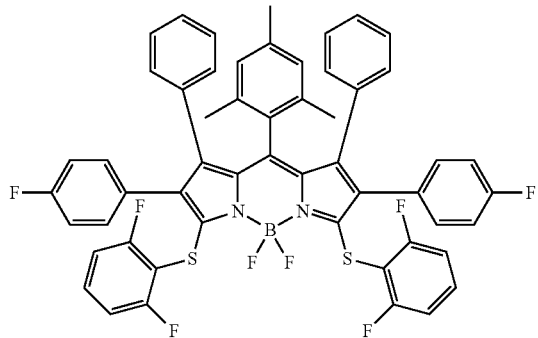
68
-continued
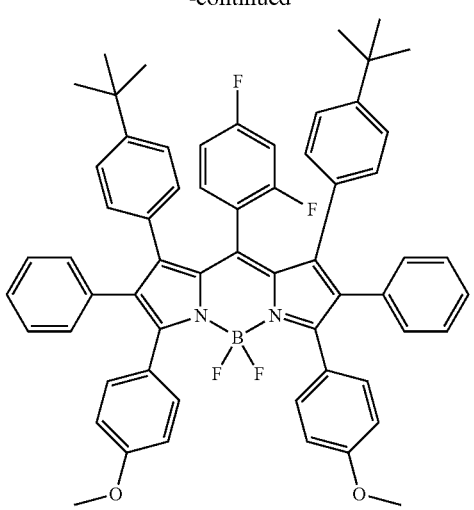
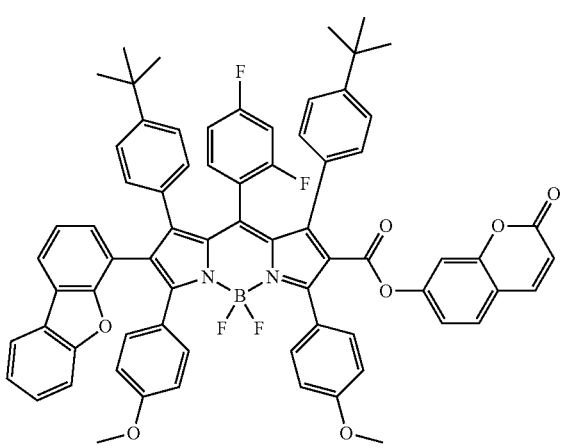

69
-continued
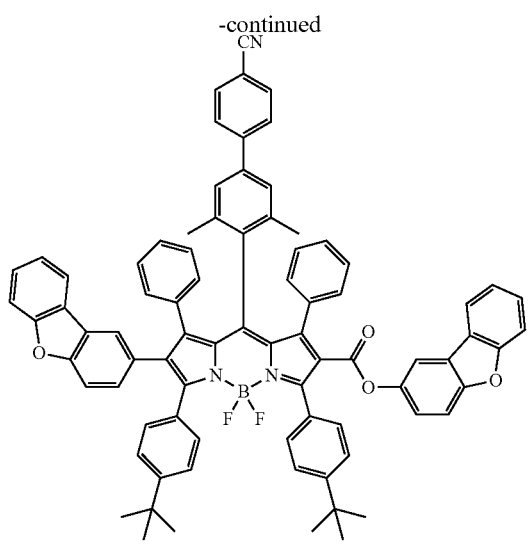
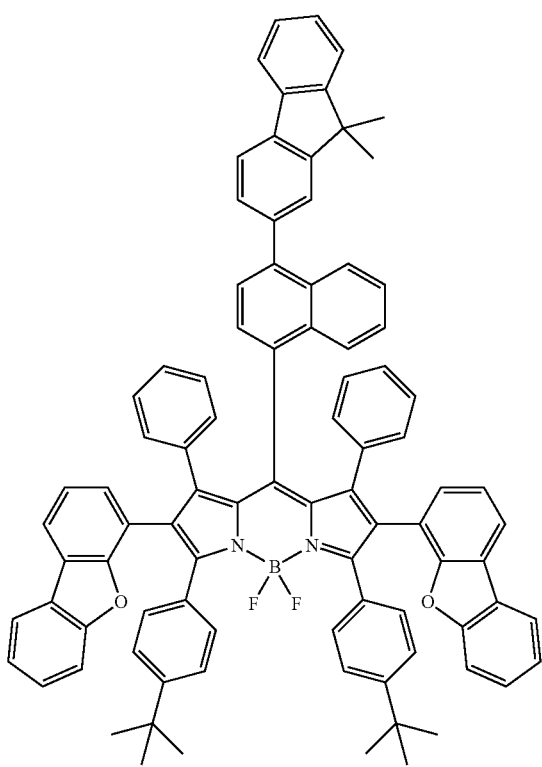
70
-continued
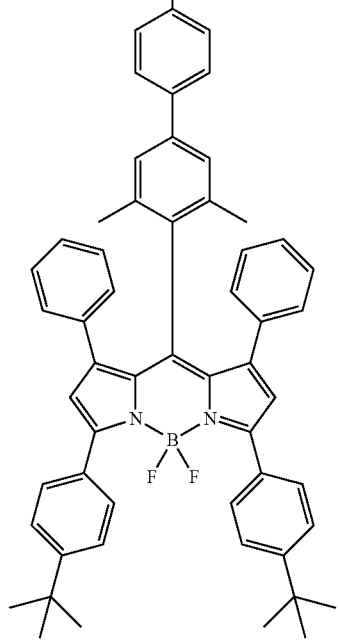
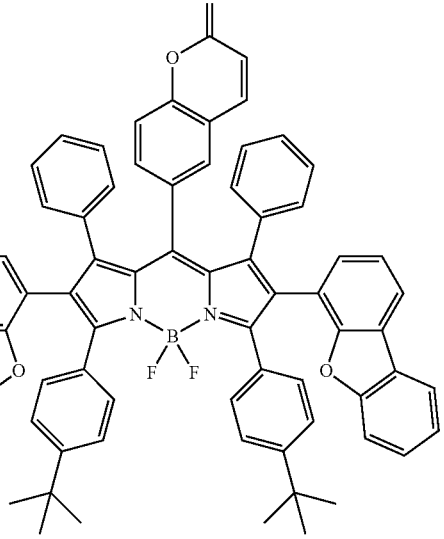
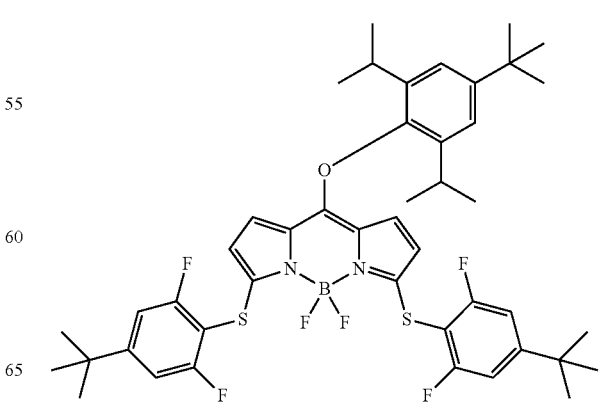

71
-continued
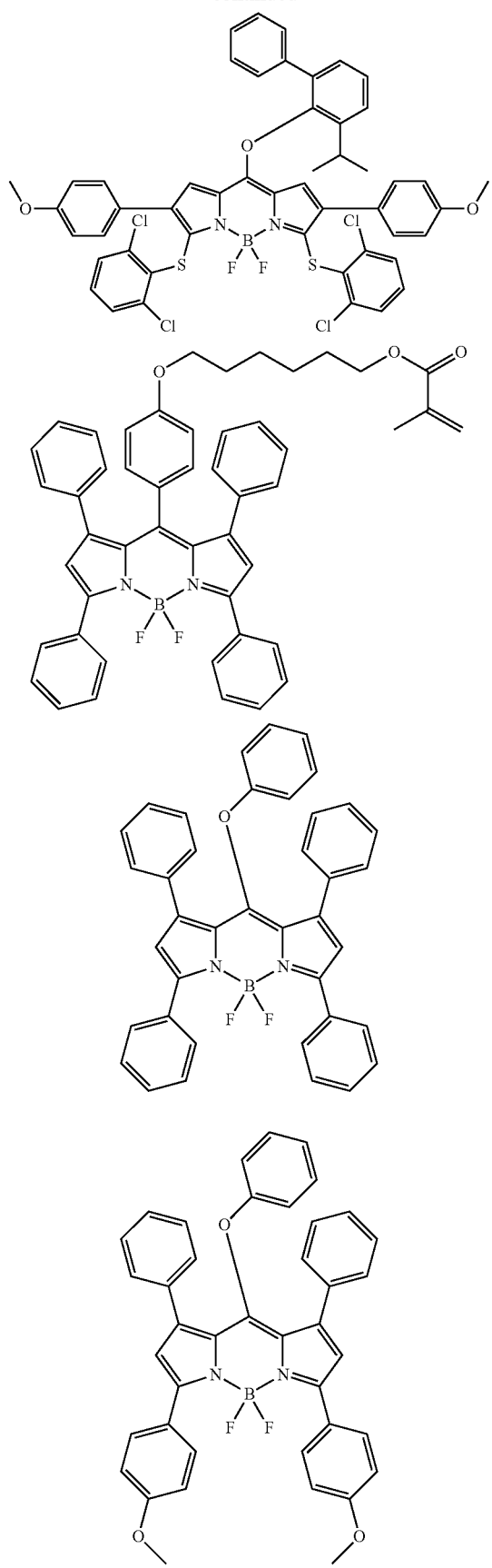
72
-continued
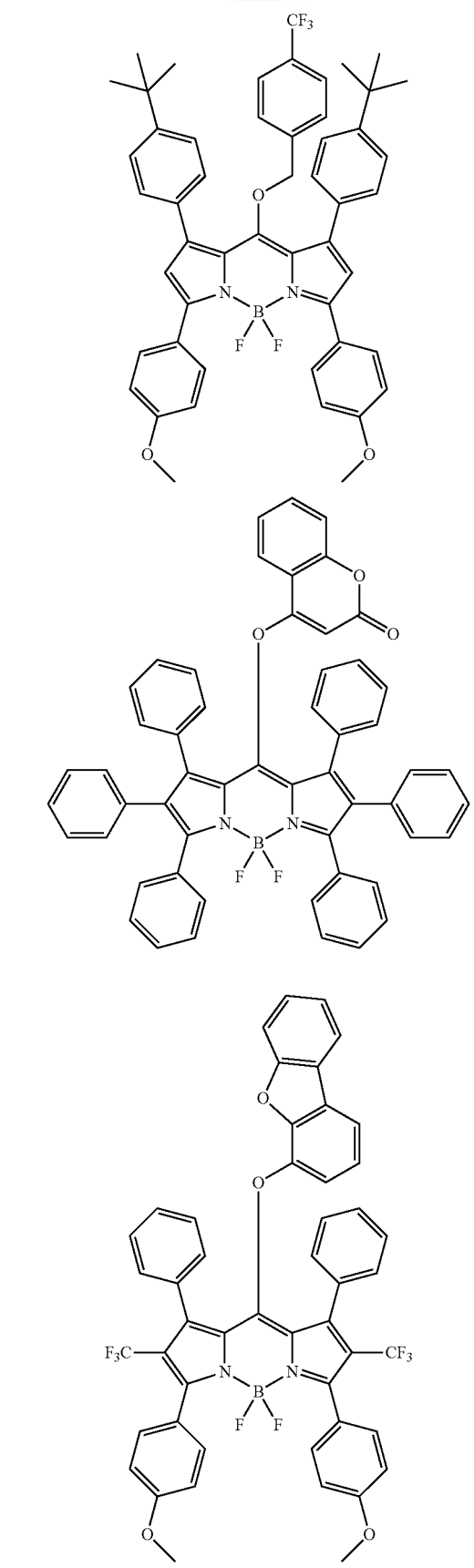

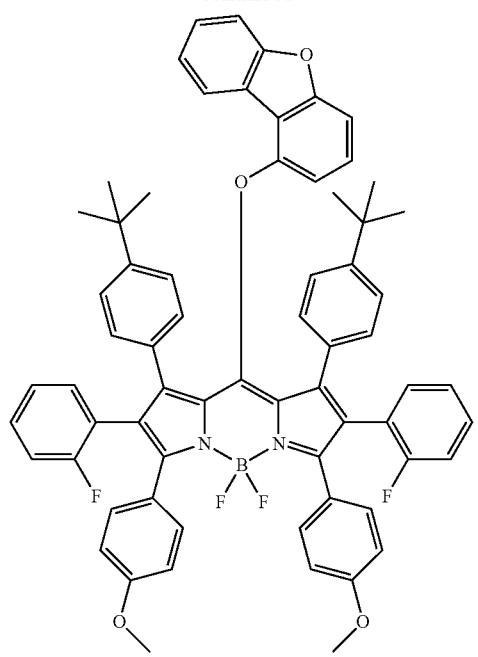
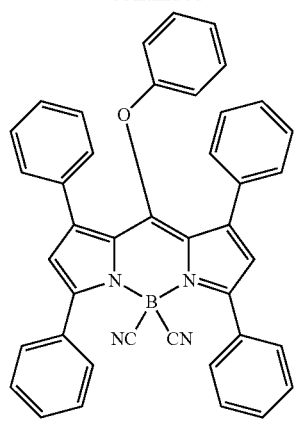
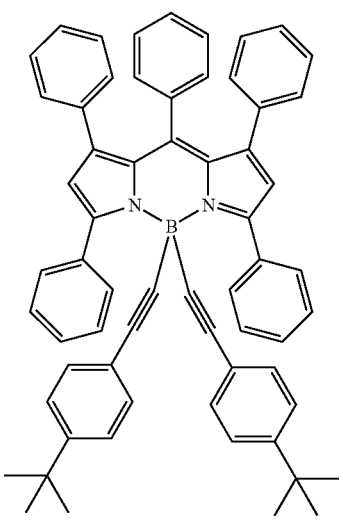
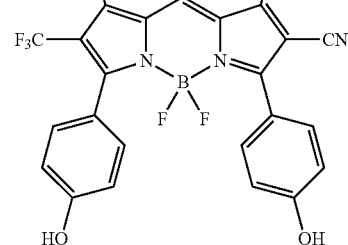
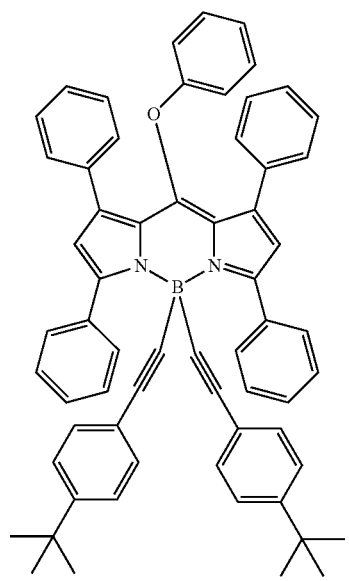
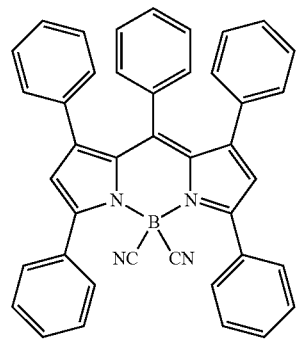

75
-continued
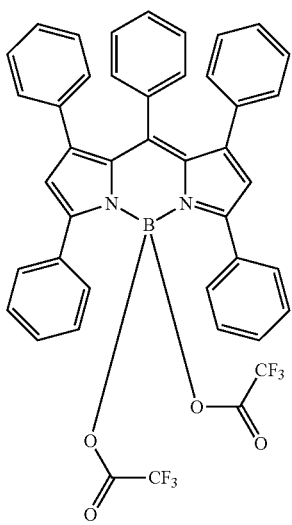
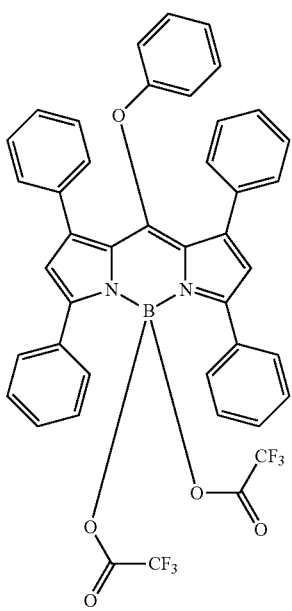
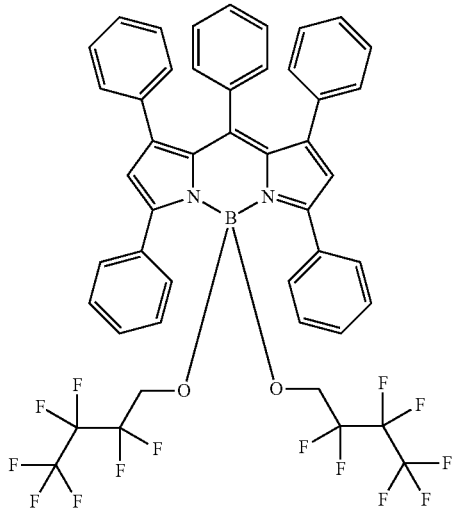
76
-continued
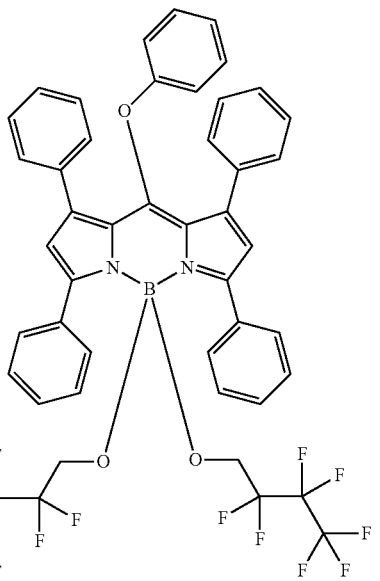
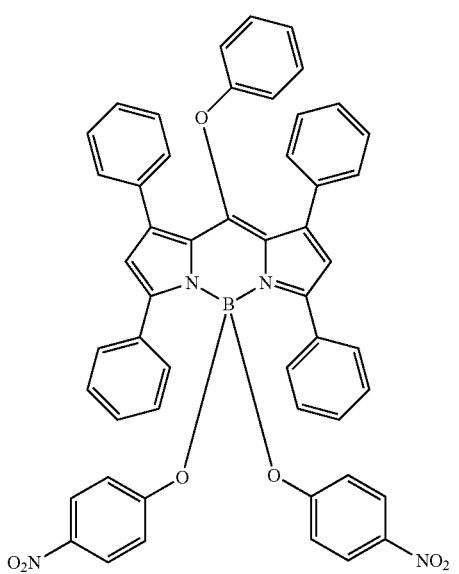

-continued

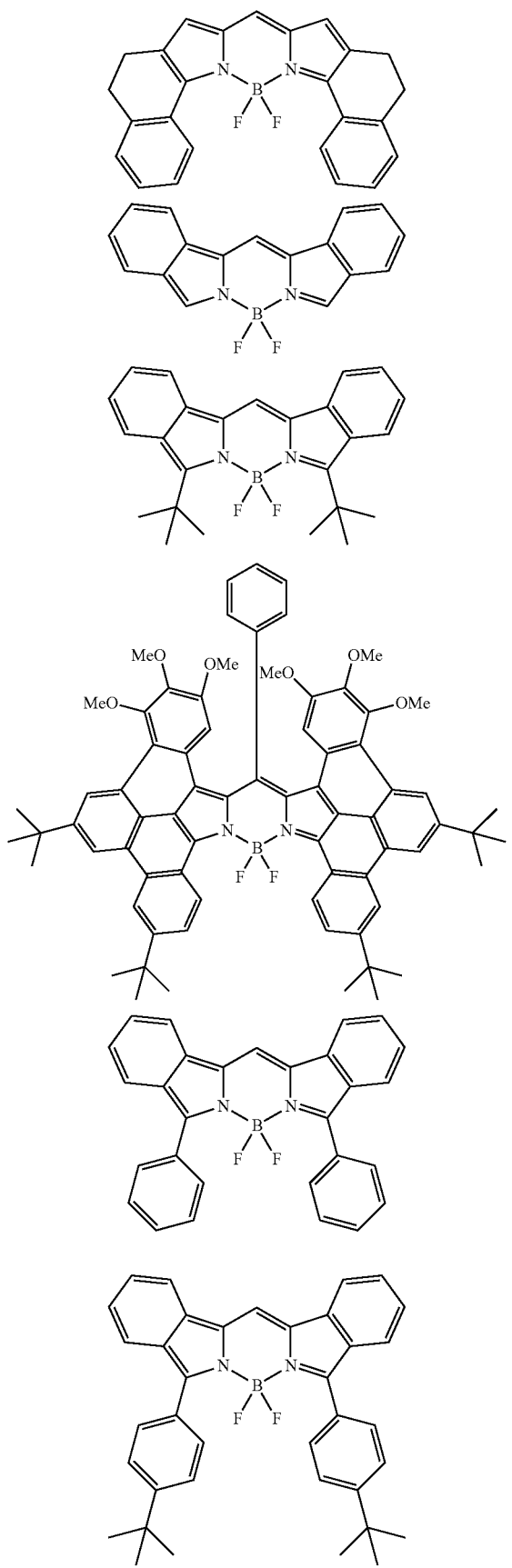

-continued

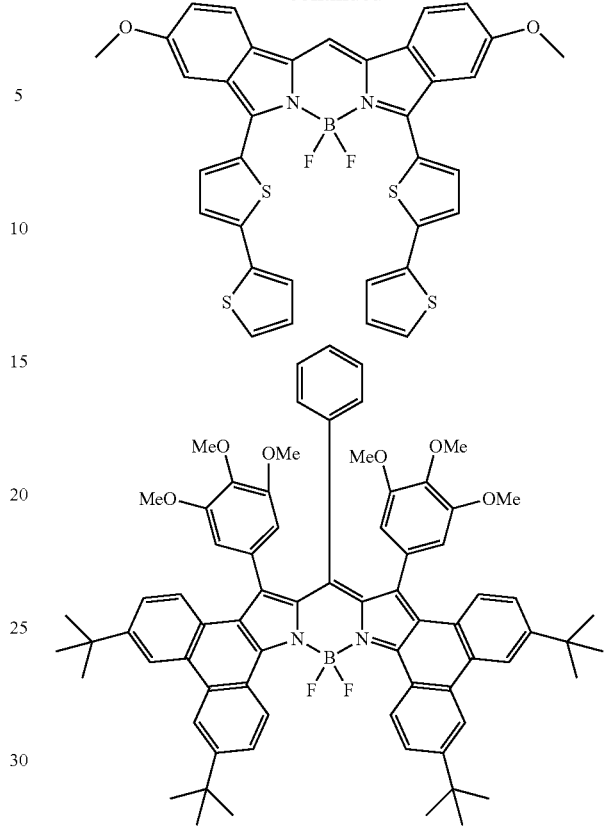

In the compounds, Me is a methyl group, and Ph is a phenyl group.

According to one embodiment of the present specification, the content of the compound represented by Chemical Formula 1 may be from 0.1 parts by weight to 10 parts by weight, specifically from 0.1 parts by weight to 5 parts by weight, and more specifically from 0.1 parts by weight to 3 parts by weight based on a total 100 parts by weight of the color conversion composition.

When the content of the compound represented by Chemical Formula 1 satisfies the above-mentioned range, energy absorbed from a blue light OLED may be effectively transferred to the compound represented by Chemical Formula 2.

According to one embodiment of the present specification, the content of the compound represented by Chemical Formula 2 may be from 0.1 parts by weight to 10 parts by weight, specifically from 0.1 parts by weight to 5 parts by weight, and more specifically from 0.15 parts by weight to 2.5 parts by weight based on a total 100 parts by weight of the color conversion composition.

When the content of the compound represented by Chemical Formula 2 satisfies the above-mentioned range, light having a maximum emission wavelength in 500 nm to 650 nm may be emitted with enhanced luminance by receiving energy that the compound represented by Chemical Formula 1 absorbs.

According to one embodiment of the present specification, the color conversion composition may further include a resin matrix, a functional monomer and a photoinitiator.

According to one embodiment of the present specification, the color conversion composition may further include a resin matrix.

The resin matrix material is preferably a thermoplastic polymer or a thermocurable polymer. Specifically, a poly (meth)acryl-based such as polymethyl methacrylate (PMMA), a polycarbonate (PC)-based, a polystyrene (PS)-based, a polyarylene (PAR)-based, a polyurethane (PU)-based, a styrene-acrylonitrile (SAN)-based, a polyvinylidene fluoride (PVDF)-based, a modified polyvinylidene fluoride (modified-PVDF)-based and the like may be used as the resin matrix material.

The content of the resin matrix may be from 5 parts by weight to 80 parts by weight, from 10 parts by weight to 70 parts by weight, or from 15 parts by weight to 50 parts by weight based on a total 100 parts by weight of the color conversion composition.

In one embodiment of the present specification, as examples of the functional monomer, one or more types selected from the group consisting of monofunctional monomers such as polyethylene glycol mono(meth)acrylate, polypropylene glycol mono(meth)acrylate and phenoxyethyl (meth)acrylate; and multifunctional monomers such as polyethylene glycol (meth)acrylate, polypropylene glycol (meth) acrylate, trimethylolethane triacrylate, trimethylolpropane triacrylate, neopentyl glycol (meth)acrylate, pentaerythritol tetraacrylate, pentaerythritol triacrylate, dipentaerythritol pentaacrylate and dipentaerythritol hexaacrylate may be used, however, the functional monomer is not limited thereto.

In one embodiment of the present specification, the color conversion composition may include a multifunctional monomer. When including a multifunctional monomer, more efficient color conversion may be achieved and physical stability is enhanced by bonding with the compound of Chemical Formula 1 and the compound of Chemical Formula 2.

The content of the functional monomer may be from 1 parts by weight to 70 parts by weight, from 10 parts by weight to 60 parts by weight, or from 30 parts by weight to 60 parts by weight based on a total 100 parts by weight of the color conversion composition.

According to one embodiment of the present specification, the photoinitiator is not particularly limited as long as it is an initiator generating radicals by light to trigger crosslinkage, and examples thereof may include one or more types selected from the group consisting of an acetophenone-based compound, a biimidazole-based compound, a triazine-based compound and an oxime-based compound.

The acetophenone-based compound may be selected from among 2-hydroxy-2-methyl-1-phenylpropan-1-one, 1-(4-isopropylphenyl)-2-hydroxy-2-methylpropan-1-one, 4-(2-hydroxyethoxy)-phenyl-(2-hydroxy-2-propyl)ketone, 1-hydroxycyclohexylphenyl ketone, benzoin methyl ether, benzoin ethyl ether, benzoin isobutyl ether, benzoin butyl ether, 2,2-dimethoxy-2-phenylacetophenone, 2-methyl-(4-methylthio)phenyl-2-morpholino-1-propan-1-one, 2-benzyl-2-dimethylamino-1-(4-morpholinophenyl)-butan-1-one, 2-(4-bromo-benzyl-2-dimethylamino-1-(4-morpholinophenyl)-butan-1-one and 2-methyl-1-[4-(methylthio)phenyl]-2-morpholinopropan-1-one, but is not limited thereto.

The biimidazole-based compound may be selected from among 2,2-bis(2-chlorophenyl)-4,4',5,5'-tetra phenyl biimidazole, 2,2'-bis(o-chlorophenyl)-4,4',5,5'-tetrakis(3,4,5-trimethoxyphenyl)-1,2'-biimidazole, 2,2'-bis(2,3-dichlorophenyl)-4,4',5,5'-tetraphenyl biimidazole and 2,2'-bis(o-chlorophenyl)-4,4,5,5'-tetraphenyl-1,2'-biimidazole, but is not limited thereto.

The triazine-based compound may be selected from among 3-{4-[2,4-bis(trichloromethyl)-s-triazin-6-yl] phenylthio}propionic acid, 1,1,1,3,3,3-hexafluoroisopropyl-3-{4-[2,4-bis(trichloromethyl)-s-triazin-6-yl] phenylthio}propionate, ethyl-2-{4-[2,4-bis (trichloromethyl)-s-triazin-6-yl]phenylthio}acetate, 2-epoxymethyl-2-{4-[2,4-bis(trichloromethyl)-s-triazin-6-yl]phenylthio}acetate, cyclohexyl-2-{4-[2,4-bis(trichloromethyl)-s-triazin-6-yl]phenylthio}acetate, benzyl-2-{4-[2,4-bis(trichloromethyl)-s-triazin-6-yl]phenylthio}acetate, 3-{chloro-4-[2,4-bis(trichloromethyl)-s-triazin-6-yl] phenylthio}propionic acid, 3-{4-[2,4-bis(trichloromethyl)-s-triazin-6-yl]phenylthio}propionamide, 2,4-bis(trichloromethyl)-6-p-methoxystyryl-s-triazine, 2,4-bis(trichloromethyl)-6-(1-p-dimethylaminophenyl)-1,3,-butadienyl-s-triazine, 2-hydroxyphenyl-s-triazine and 2-trichloromethyl-4-amino-6-p-methoxystyryl-s-triazine, but is not limited thereto.

The oxime-based compound may be selected from among 1,2-octadione-1-(4-phenylthio)phenyl-2-(o-benzoyloxime) (Ciba-Geigy Corporation, CGI 124), ethanone-1-(9-ethyl)-6-(2-methylbenzoyl-3-yl)-1-(O-acetyloxime) (CGI 242), N-1919 (Adeka Corporation) and OXE-02 ((E)-1-(((1-(9-ethyl-6-(2-methylbenzoyl)-9H-carbazol-3-yl)ethylidene) amino)oxy)ethan-1-one, BASF Corporation), but is not limited thereto.

The content of the photoinitiator may be from 0.1 parts by weight to 10 parts by weight, and preferably from 1 parts by weight to 5 parts by weight based on a total 100 parts by weight of the color conversion composition.

According to one embodiment of the present specification, the color conversion film according to the embodiments described above additionally includes light diffusing particles. By dispersing light diffusing particles into the color conversion film instead of a light diffusing film used in the art for enhancing luminance, higher luminance may be exhibited compared to using a separate light diffusing film, and an adhering process may be skipped as well.

As the light diffusing particles, particles having a high refractive index with the resin matrix may be used, and examples thereof may include $TiO_2$, silica, borosilicate, alumina, sapphire, air or other air-filled hollow beads or particles (for example, air/gas-filled glass or polymers); polystyrene, polycarbonate, polymethyl methacrylate, acryl, methyl methacrylate, styrene, a melamine resin, a formaldehyde resin, or polymer particles including melamine and formaldehyde resins, or any suitable combination thereof.

The light diffusing particles may have particle diameters in a range of 0.01 μm to 5 μm, for example, in a range of 0.3 μm to 1 μm. The content of the light diffusing particles may be determined as necessary, and for example, may be in a range of approximately 1 part by weight to 30 parts by weight based on 100 parts by weight of the resin matrix.

In one embodiment of the present specification, the color conversion composition may further include one or more types of additives selected from among a curing agent, a surfactant, an adhesion promoter, an adhesion aid, an ultraviolet absorber and an anti-coagulant, and the content of the additive is from 0.1 parts by weight to 10 parts by weight, and preferably from 0.1 parts by weight to 5 parts by weight based on a total 100 parts by weight of the color conversion composition.

In one embodiment of the present specification, the color conversion film includes a cured material of the color conversion composition described above.

The color conversion film may further include an additional layer including a compound emitting light with a wavelength different from the color conversion composition described above.

The color conversion film according to the embodiments described above may have a thickness of 2 μm to 200 μm. Particularly, the color conversion film may exhibit high luminance even with a small thickness of 2 μm to 20 μm. This is due to the fact that the content of the fluorescent material molecules included in the unit volume is higher compared to quantum dots.

The color conversion film according to the embodiments described above may have a substrate provided on one surface. This substrate may function as a support when preparing the color conversion film. Types of the substrate are not particularly limited, and the material or thickness is not limited as long as it is transparent and is capable of functioning as the support. Herein, being transparent means having visible light transmittance of 70% or higher. For example, a PET film may be used as the substrate.

The color conversion film described above may be prepared by coating a solution in which the color conversion composition is dissolved on a substrate and drying the result, or by extruding and filming the color conversion composition.

The color conversion composition is dissolved in the solution, and therefore, the color conversion composition is homogeneously distributed in the solution. This is different from a quantum dot film preparation process that requires a separate dispersion process.

As for the color conversion composition-dissolved solution, the preparation method is not particularly limited as long as the color conversion composition is dissolved in the solution.

According to one example, the color conversion composition-dissolved solution may be prepared by dissolving the above-described color conversion composition in a solvent.

According to another example, the color conversion composition-dissolved solution may be prepared by preparing a first solution by dissolving the color conversion composition in a solvent, preparing a second solution by dissolving a resin in a solvent, and mixing the first solution and the second solution. When mixing the first solution and the second solution, it is preferred that these be homogeneously mixed. However, the method is not limited thereto, and a method of simultaneously adding and dissolving the color conversion composition and a resin in a solvent, a method of dissolving the color conversion composition in a solvent and subsequently adding and dissolving a resin, a method of dissolving a resin in a solvent and then subsequently adding and dissolving the color conversion composition, and the like, may be used.

As the resin included in the solution, the resin matrix material described above, a monomer curable to this resin matrix resin, or a mixture thereof, may be used. For example, the monomer curable to the resin matrix resin includes a (meth)acryl-based monomer, and this may be formed to a resin matrix material by UV curing. When using such a curable monomer, an initiator required for curing may be further added as necessary.

The solvent is not particularly limited as long as it is capable of being removed by drying afterword while having no adverse effects on the coating process.

Non-limiting examples of the solvent may include toluene, xylene, acetone, chloroform, various alcohol-based solvents, methyl ethyl ketone (MEK), methyl isobutyl ketone (MIBK), ethyl acetate (EA), butyl acetate, dimethylformamide (DMF), dimethylacetamide (DMAc), dimethyl sulfoxide (DMSO), N-methyl-pyrrolidone (NMP), propylene glycol monomethyl ether acetate (PGEMA), and the like, but are not limited thereto. In addition, the solvent may be used in one type or as a mixture of two or more types.

In the color conversion composition-dissolved solution, the solid content may be from 10% by weight to 30% by weight, or from 15% by weight to 25% by weight.

The process of coating the color conversion composition-dissolved solution described above on a substrate may use a roll-to-roll process. For example, a process of unwinding a substrate from a substrate-wound roll, coating the color conversion composition-dissolved solution on one surface of the substrate, drying the result, and then winding the result again on the roll may be used. When a roll-to-roll process is used, viscosity of the resin solution is preferably determined in a range capable of conducting the process, and for example, may be determined in a range of 200 cps to 2,000 cps.

As the coating method, various known methods may be used, and for example, a die coater may be used, or various bar coating methods such as a comma coater and a reverse comma coater may be used.

After the coating, a drying process is conducted. The drying process may be conducted under a condition required to remove a solvent. For example, a color conversion film including a fluorescent material including the color conversion composition having target thickness and concentration may be obtained on a substrate by conducting the drying in an oven located close to a coater under a condition to sufficiently evaporate a solvent, in a direction of the substrate progressing during the coating process.

When a monomer curable to the resin matrix resin is used as the resin included in the solution, curing, for example, UV curing, may be conducted prior to or at the same time as the drying.

When the color conversion composition is filmed by being extruded with a resin, extrusion methods known in the art may be used, and for example, the color conversion film may be prepared by extruding the color conversion composition with a resin such as a polycarbonate (PC)-based, a poly(meth)acryl-based and a styrene-acrylonitrile (SAN)-based.

According to one embodiment of the present specification, the color conversion film may have a protective film or a barrier film provided on at least one surface. As the protective film or the barrier film, those known in the art may be used.

One embodiment of the present specification provides a backlight unit including the color conversion film including the color conversion composition described above. The backlight unit may have backlight unit constitutions known in the art except for including the color conversion film. FIG. 1 illustrates a mimetic diagram of a backlight unit structure according to one embodiment. According to FIG. 1, the color conversion film including the color conversion composition is provided on a surface opposite to a surface facing a reflecting plate of a light guide plate. FIG. 1 illustrates a constitution including a light source and a reflecting plate surrounding the light source, however, the constitution is not limited to such a structure, and may vary depending on the backlight unit structure known in the art.

According to one embodiment of the present specification, the backlight unit includes a light source, and the light source may emit blue light.

In another embodiment, the backlight unit includes a light source, and light emitted from the light source may have an emission peak in a region of 430 nm to 470 nm.

In another embodiment, the backlight unit includes a light source, the light source may be a white light source, and light emitted from the white light source includes an emission peak in a region of 430 nm to 470 nm.

In another embodiment, the backlight unit includes a light source, the light source may be a blue light source, and light emitted from the blue light source includes a light emission peak in a region of 430 nm to 470 nm.

In another embodiment, the backlight unit includes a light source, and the light source may be a blue light OLED.

The backlight unit according to one embodiment of the present specification uses blue light, and blue, red and green light emission may be obtained by the color conversion film including the compound of Chemical Formula 1 and the compound of Chemical Formula 2.

In addition, as the light source, a direct type as well as a side chain type may be used, and the reflecting plate or the reflective layer may not be included or may be replaced with other constituents as necessary, and as necessary, additional films such as a light diffusing film, a light concentrating film and a luminance enhancing film may be further provided. Preferably, a prism sheet, a multilayer reflective polarizer film, a light concentrating film or a luminance enhancing film is further provided on the color conversion film.

In the constitution of the backlight unit as in FIG. 1, a scattering pattern may be provided as necessary on an upper surface or a lower surface of the light guide plate. Light introduced into the light guide plate has non-uniform light distribution due to repetition of optical processes such as reflection, total reflection, refraction or transmission, and the scattering pattern may be used to induce the non-uniform light distribution to uniform brightness.

One embodiment of the present specification provides a display apparatus including the backlight unit. The display apparatus is not particularly limited as long as it includes the backlight unit. For example, the display apparatus includes a display module and a backlight unit. FIG. 2 illustrates a structure of the display apparatus. However, the structure is not limited thereto, and between the display module and the backlight unit, additional films such as a light diffusing film, a light concentrating film and a luminance enhancing film may be further provided as necessary.

Hereinafter, the present specification will be described in detail with reference to examples. However, the examples according to the present specification may be modified to various other forms, and the scope of the present specification is not to be construed as being limited to the examples described below. Examples of the present specification are provided in order to more fully describe the present specification to those having average knowledge in the art.

The compounds according to one embodiment of the present application may be prepared using preparation methods to describe below.

For example, the compound of Chemical Formula 1 may have its core structure prepared as in the following Reaction Formula 1. Pyrrole, an intermediate of the compound of Chemical Formula 2, may be prepared as in Reaction Formula 2. Substituents may bond using methods known in the art, and types, positions, or the number of the substituents may vary depending on technologies known in the art.

[Reaction Formula 1]

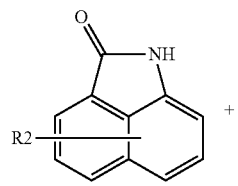

+

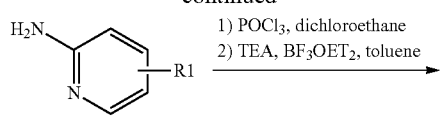

-continued

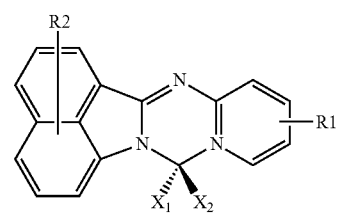

Benzo[c,d]indol-2(1H)-one (1 equivalents) and aminopyrimidine (1.5 equivalents) were introduced to a solvent, and stirred while heating at 90° C. under nitrogen. After benzo[c,d]indol-2(1H)-one disappeared, the reaction material was cooled. After pouring water thereto, the result was stirred for 30 minutes, then extracted using chloroform, and dried with anhydrous magnesium sulfate. The result was concentrated through vacuum distillation, then dissolved in toluene, and stirred at 120° C. after adding TEA and $BF_3OET_2$ thereto while stirring. After the reaction was finished, the result was cooled, extracted with $CHCl_3$, dried with anhydrous magnesium sulfate, then concentrated through vacuum distillation, and purified through recrystallization or a column.

General Synthesis of Pyrrole

[Reaction Formula 2]

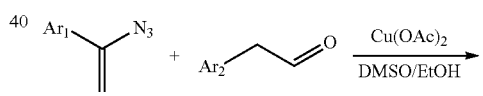

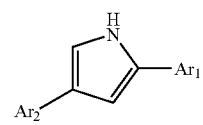

Aldehyde (1 equivalents) and azide (1.5 equivalents) were introduced to a solvent, and after introducing a catalyst (approximately 2% to 5%) thereto, the result was stirred while heating at 110° C. under argon. After the reaction was finished, the result was extracted using water and ethyl acetate, and dried with anhydrous magnesium sulfate. The result was concentrated through vacuum distillation, and then purified through a column.

In Reaction Formulae 1 and 2, R1, R2, $X_1$, $X_2$, $Ar_1$ and $Ar_2$ are the same as or different from each other, and each independently hydrogen; deuterium; or a monovalent substituent.

[Preparation Example 1] Preparation of Compound 1

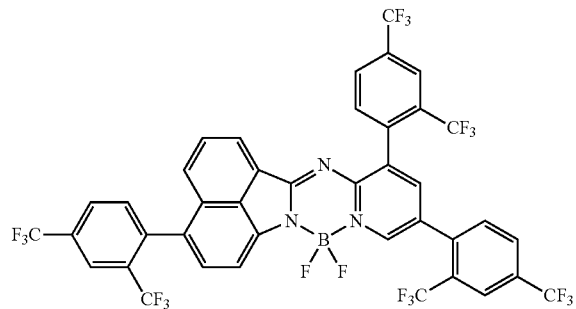

Preparation was conducted in the same manner as in the method of Reaction Formula 1, and Compound 1 was obtained in a 38% yield through column purification.

HR LC/MS/MS m/z calculated for $C_{40}H_{16}BF_{20}N_3$ (M+): 929.1118. found: 929.1119.

[Preparation Example 2] Preparation of Compound 2

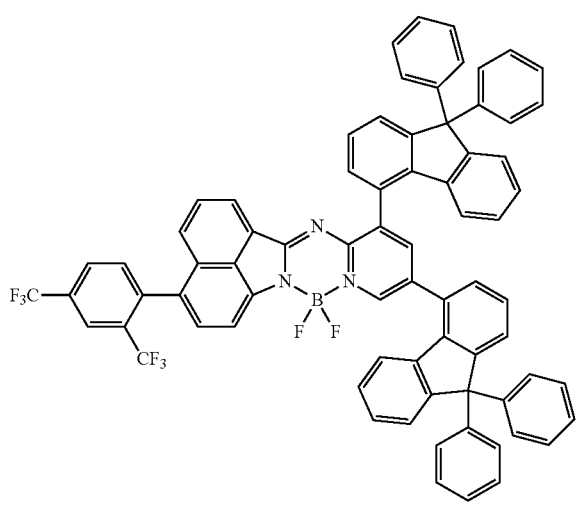

Preparation was conducted in the same manner as in the method of Reaction Formula 1, and Compound 2 was obtained in a 78% yield through column purification.

HR LC/MS/MS m/z calculated for $C_{74}H_{44}BF_8N_3$ (M+): 1137.3501. found: 1137.3508.

[Preparation Example 3] Preparation of Compound 3

Preparation was conducted in the same manner as in the method of Reaction Formula 1, and Compound 3 was obtained in a 55% yield through column purification.

HR LC/MS/MS m/z calculated for $C_{33}H_{13}BF_{17}N_3$ (M+): 785.0931. found: 785.0928.

[Preparation Example 4] Preparation of Compound 4

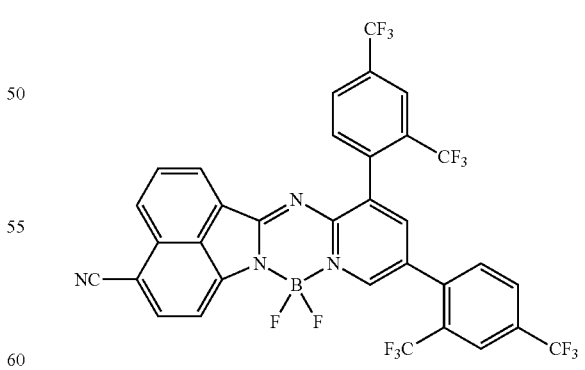

Preparation was conducted in the same manner as in the method of Reaction Formula 1, and Compound 4 was obtained in a 58% yield through column purification.

HR LC/MS/MS m/z calculated for $C_{33}H_{13}BF_{14}N_3$ (M+): 742.1010. found: 742.1011.

[Preparation Example 5] Preparation of Compound 5

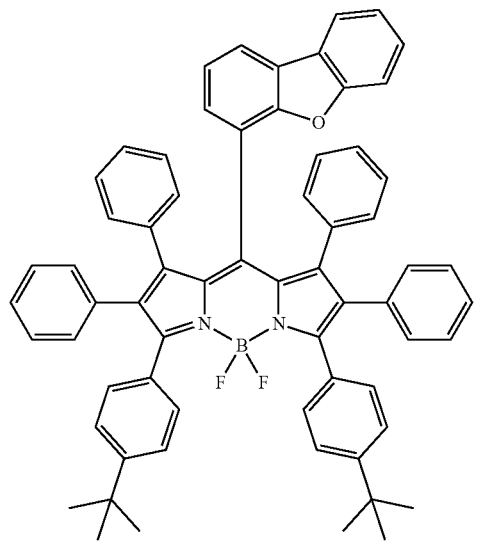

Preparation was conducted in the same manner as in the method of Reaction Formula 2, and Compound 5 was obtained in a 62% yield through column purification.

HR LC/MS/MS m/z calculated for $C_{65}H_{53}BF_2N_2O$ (M+): 926.4219. found: 926.4223.

[Preparation Example 6] Preparation of Compound 6

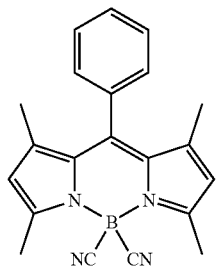

Preparation was conducted in the same manner as in the method of Reaction Formula 2, and Compound 6 was obtained in a 78% yield through column purification.

HR LC/MS/MS m/z calculated for $C_{21}H_{19}BN_4$ (M+): 338.1703. found: 338.1699.

Properties of Compounds 1 to 6 prepared in Preparation Examples 1 to 6 are as shown in the following Table 1, and measurements were made after preparing the solution to $10^{-5}$ M using toluene.

TABLE 1

| Compound | Abs (nm) | PL (nm) | Quantum Efficiency (%) | FWHM (nm) | Abs Intensity (@450 nm) |
|---|---|---|---|---|---|
| 1 | 458 | 504 | 90.0 | 63 | 0.3247 |
| 2 | 461 | 509 | 94.0 | 60 | 0.3236 |
| 3 | 456 | 504 | 92.8 | 68 | 0.3001 |
| 4 | 452 | 496 | 99.3 | 58 | 0.4203 |
| 5 | 590 | 627 | 97.2 | 39 | 0.0574 |
| 6 | 509 | 520 | 94.2 | 23 | 0.0528 |

Abs (maximum absorption wavelength) was measured using a MEGA-2100 device of SCINCO Co., Ltd. and Abs intensity (absorbance in absorption region of 450 nm) was identified, and PL (maximum emission wavelength) was measured using an FS-2 device of SCINCO Co., Ltd. and FWHM (full width at half maximum) of PL was identified. In addition, quantum efficiency was measured using a Quantaurus-QY device of Hamamatsu Photonics K.K..

Example 1

A solution was prepared by dissolving 0.5 parts by weight of prepared Compound 5 (maximum absorption wavelength 590 nm, maximum emission wavelength 627 nm, and full width at half maximum 39 nm in toluene solution), 1.0 parts by weight of prepared Compound 1 (maximum absorption wavelength 458 nm, maximum emission wavelength 504 nm, and full width at half maximum 63 nm in toluene solution), 33.9 parts by weight of an acryl-based binder, 59.3 parts by weight of a multifunctional monomer (pentaerythritol triacrylate, Nippon Kayaku Co., Ltd.), 2.3 parts by weight of an adhesion aid and surfactant (KBM 503, Shin-Etsu Chemical Co., Ltd.), and 3.0 parts by weight of a photoinitiator (Tinuvin® 477, BASF Corporation) in a propylene glycol monomethyl ether acetate (PGEMA) solvent so as to have a solid content of 21% by weight.

After sufficiently stirring the mixed solution, the solution was coated as a thin film on a glass substrate, and then dried to prepare a color conversion film.

A luminance spectrum of the prepared color conversion film was measured using a spectroradiometer (SR series of Topcon Technohouse Corporation). Specifically, the prepared color conversion film was laminated on one surface of a light guide plate of a backlight unit including an LED blue backlight (maximum emission wavelength 450 nm) and the light guide plate, and after laminating a prism sheet and a DBEF film on the color conversion film, an initial value was set so that the brightness of the blue LED light was 600 nit based on the film.

Example 2

An experiment was performed in the same manner as in Example 1 except that Compound 1 was used in 0.5 parts by weight in Example 1.

Example 3

An experiment was performed in the same manner as in Example 1 except that Compound 1 was used in 1.5 parts by weight in Example 1.

Example 4

An experiment was performed in the same manner as in Example 1 except that Compound 2 (maximum absorption wavelength 461 nm, maximum emission wavelength 509 nm, and full width at half maximum 60 nm in toluene solution) was used instead of Compound 1 in Example 1.

Example 5

An experiment was performed in the same manner as in Example 1 except that Compound 3 (maximum absorption wavelength 456 nm, maximum emission wavelength 504 nm, and full width at half maximum 68 nm in toluene solution) was used instead of Compound 1 in Example 1.

Example 6

An experiment was performed in the same manner as in Example 1 except that Compound 6 (maximum absorption wavelength 509 nm, maximum emission wavelength 520 nm, and full width at half maximum 23 nm in toluene solution) was used instead of Compound 5 in Example 1.

Example 7

An experiment was performed in the same manner as in Example 6 except that Compound 3 (maximum absorption wavelength 456 nm, maximum emission wavelength 504 nm, and full width at half maximum 68 nm in toluene solution) was used instead of Compound 1 in Example 6.

Comparative Example 1

An experiment was performed in the same manner as in Example 1 except that Compound 1 was not added and Compound 5 was used in 0.5 parts by weight in Example 1.

Comparative Example 2

An experiment was performed in the same manner as in Example 6 except that Compound 1 was not added and Compound 6 was used in 0.5 parts by weight in Example 6.

Comparative Example 3

An experiment was performed in the same manner as in Example 1 except that Compound 5 was not added and Compound 1 was used in 1.0 parts by weight in Example 1.

Properties of the color conversion films measured in the examples and the comparative examples are described in the following Table 2.

TABLE 2

| | Thin Film Emission Wavelength | | Quantum Efficiency (QY, %) | Blue Light Source Absorption (%) | Intensity (a.u.) |
|---|---|---|---|---|---|
| | $\lambda_{max}$ (nm) | FWHM (nm) | | | |
| Example 1 | 637 | 52 | 84.9 | 80.7 | 0.0275 |
| Example 2 | 637 | 52 | 85.2 | 66.8 | 0.0235 |
| Example 3 | 636 | 52 | 84.9 | 86.7 | 0.0302 |
| Example 4 | 636 | 49 | 87.7 | 79.6 | 0.0280 |
| Example 5 | 636 | 49 | 88.1 | 78.7 | 0.0269 |
| Example 6 | 529 | 51 | 78.1 | 91.9 | 0.0274 |
| Example 7 | 529 | 50 | 68.3 | 88.6 | 0.0268 |
| Comparative Example 1 | 637 | 52 | 85.6 | 26.4 | 0.0109 |
| Comparative Example 2 | 528 | 50 | 82.04 | 47.2 | 0.0190 |
| Comparative Example 3 | 535 | 81 | 81.1 | 82.5 | 0.0193 |

In Table 2, blue light source absorption (%) represents a degree of the compound absorbing the used LED blue backlight (maximum emission wavelength 450 nm) as %, and intensity (a.u.) is a number representing a y value of a maximum peak in a 500 nm to 750 nm region in the luminance spectrum.

It was identified that, the prepared film including both the compound of Chemical Formula 1 and the compound of Chemical Formula 2 followed the film prepared using only the compound of Chemical Formula 1 (Comparative Example 3) in the quantum efficiency and the degree of blue light source absorption while following the maximum emission wavelength and full width at half maximum properties of the films prepared using only the compound of Chemical Formula 2 (Comparative Examples 1 and 2). In addition, the film according to the present disclosure was measured to have higher intensity compared to the films prepared using only one of the compounds alone, and thereby exhibited more favorable efficiency.

The invention claimed is:

1. A color conversion composition comprising:
   a compound selected from any one of compounds in the following Group I; and
   a compound represented by the following Chemical Formula 2,
   wherein the compound selected from any one of the compounds in the Group I and the compound represented by the Chemical Formula 2 have a molar ratio of 1:1 to 5:1:

[Group I]

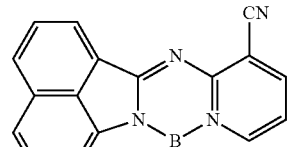

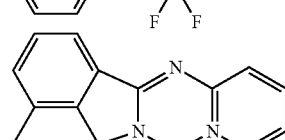

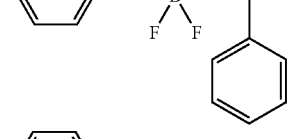

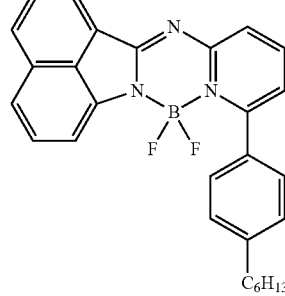

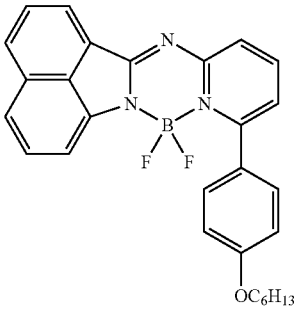

91
-continued
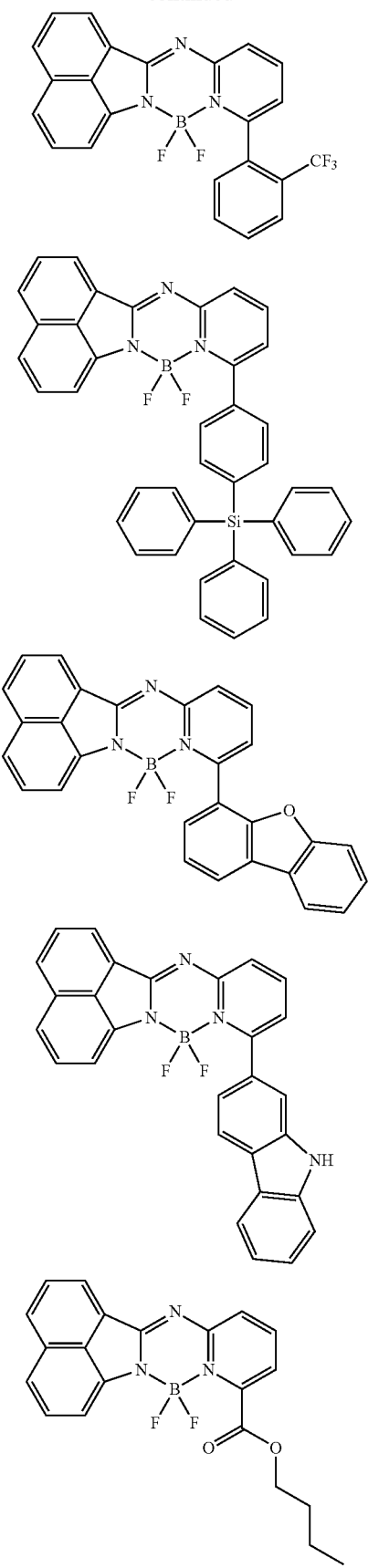
92
-continued
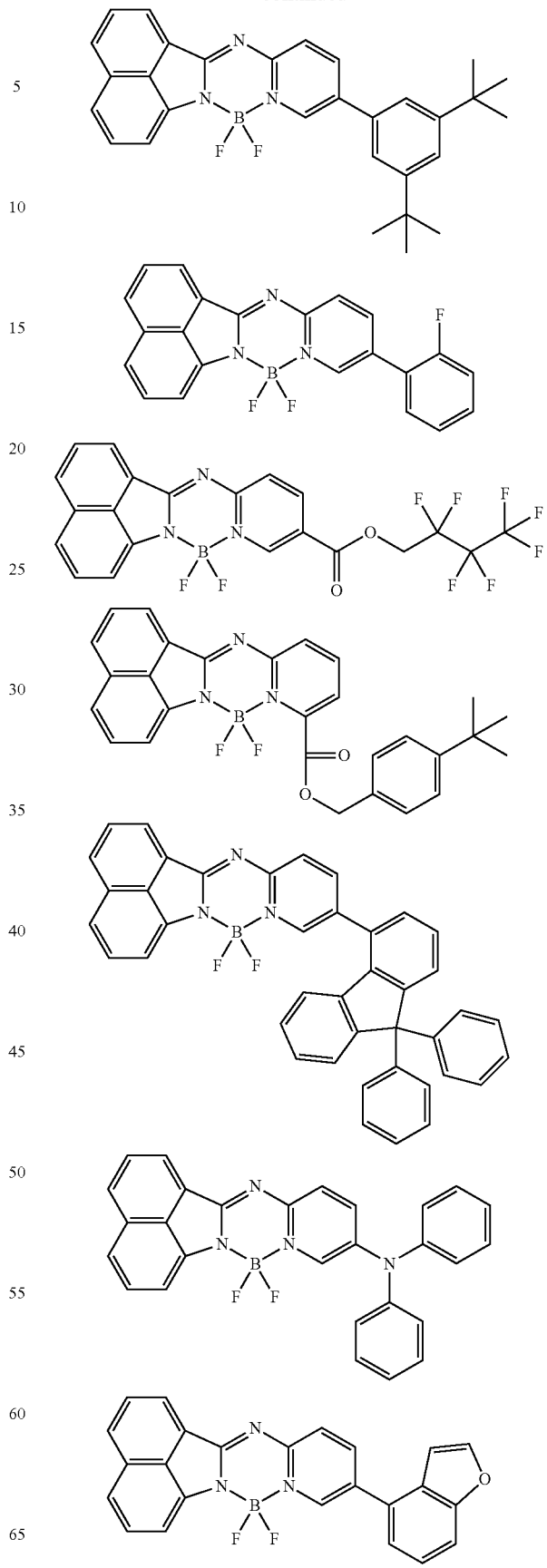

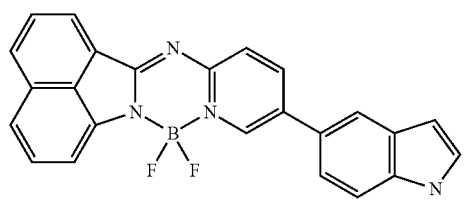
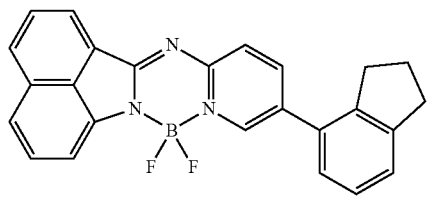
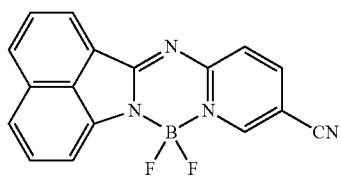
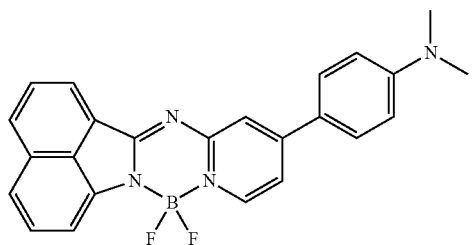
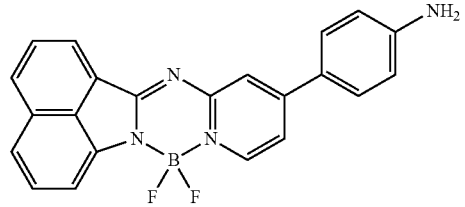
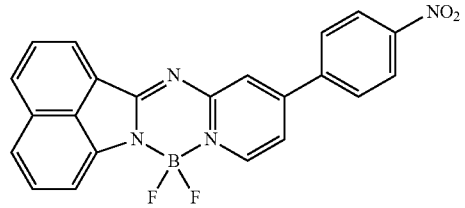
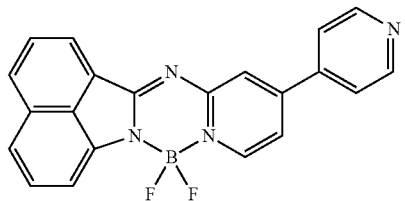
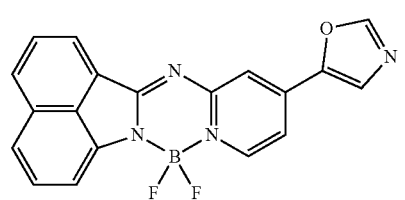
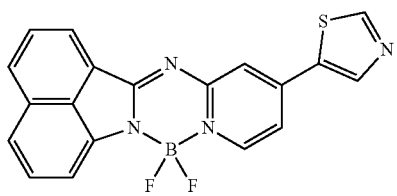
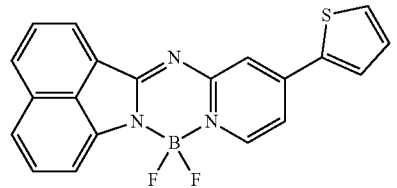
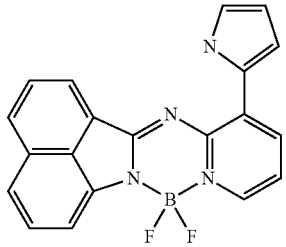
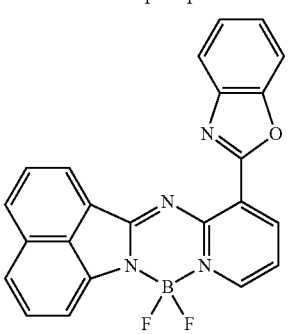
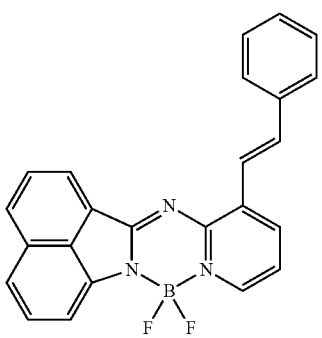
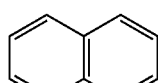
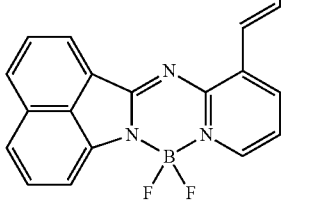

-continued
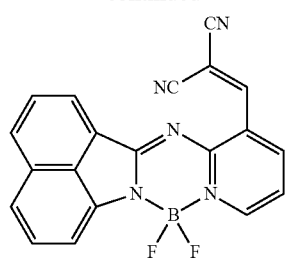
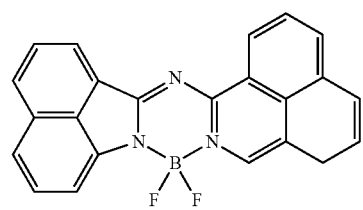
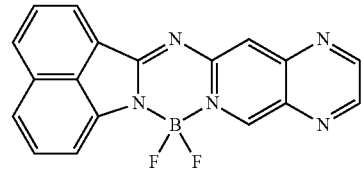
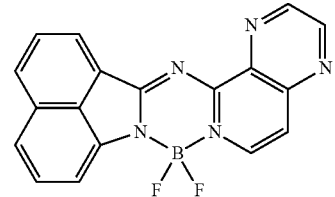
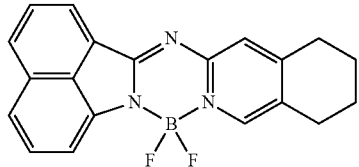
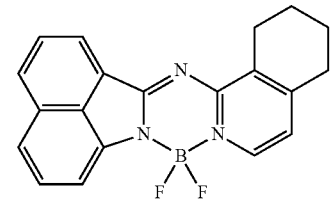
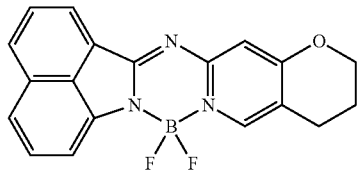
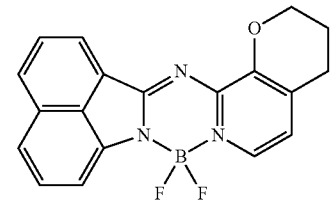
-continued
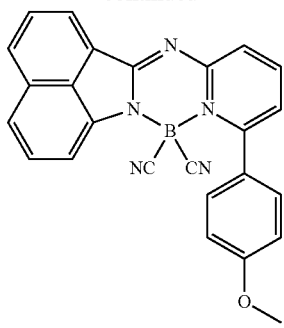
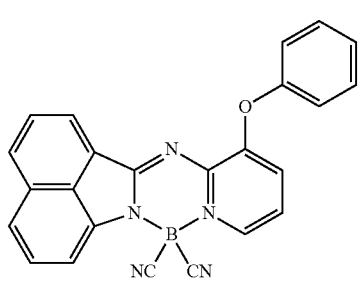
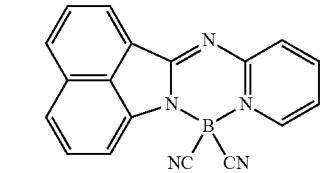
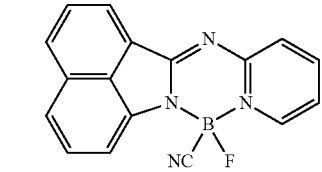
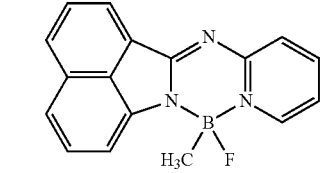
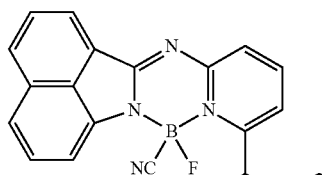
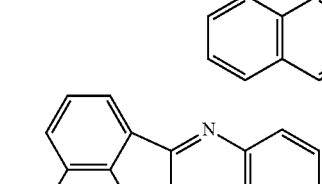
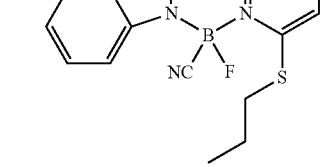

97
-continued
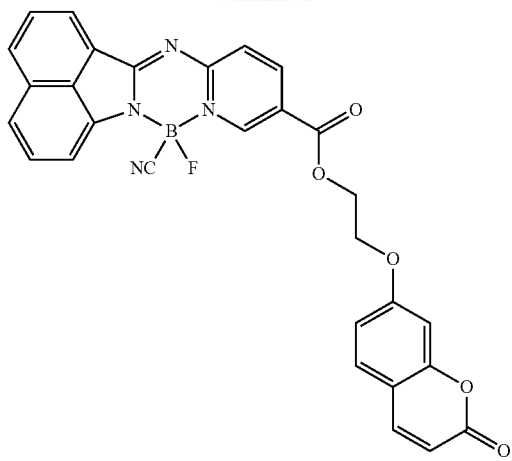
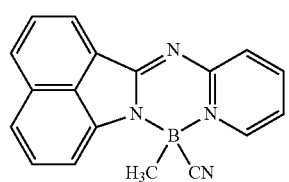
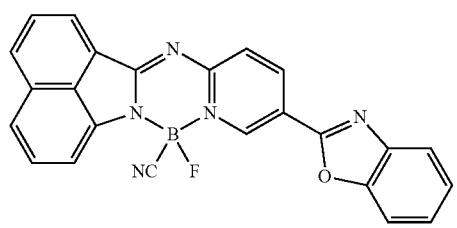
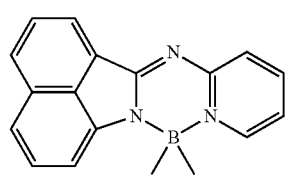
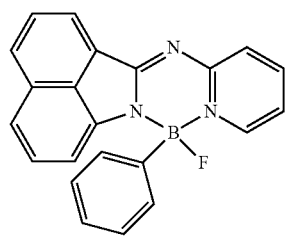
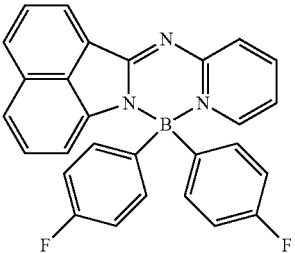
98
-continued
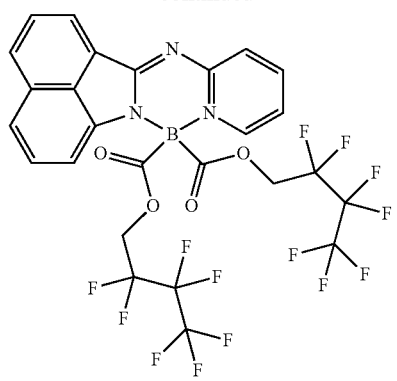
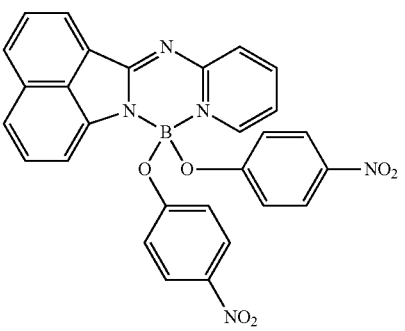
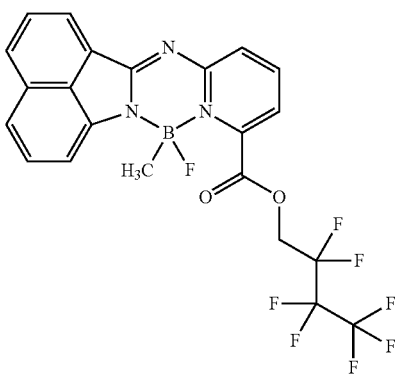
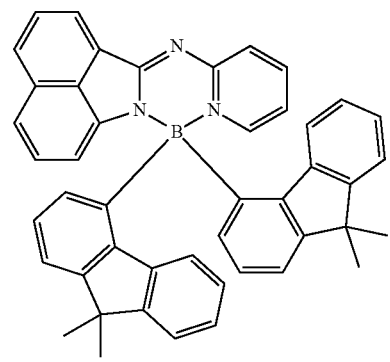

99
-continued
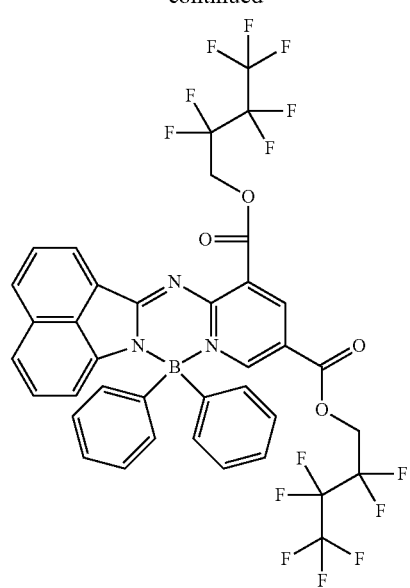
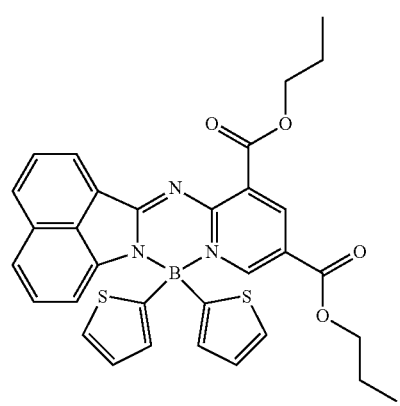
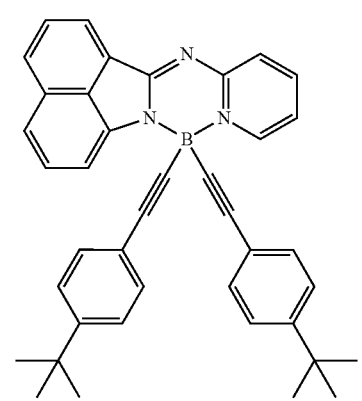
100
-continued
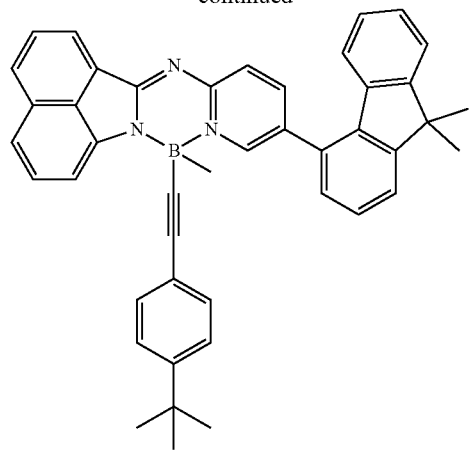
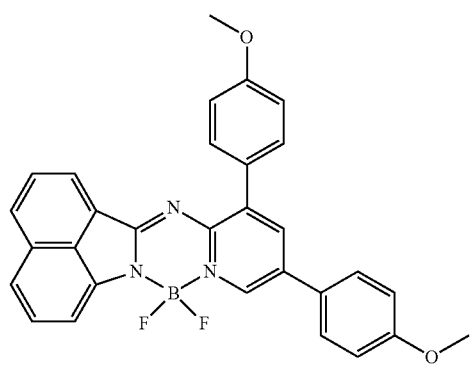
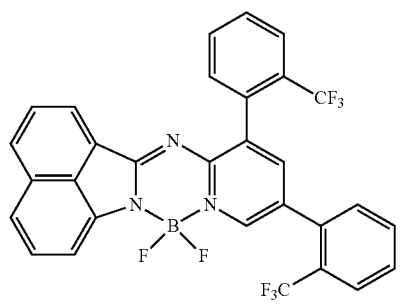
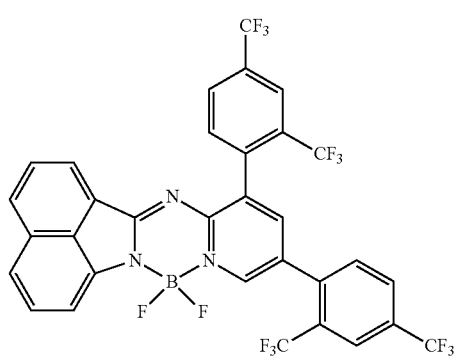

101
-continued
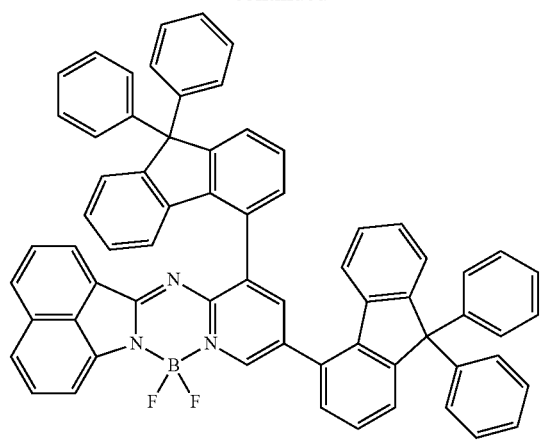
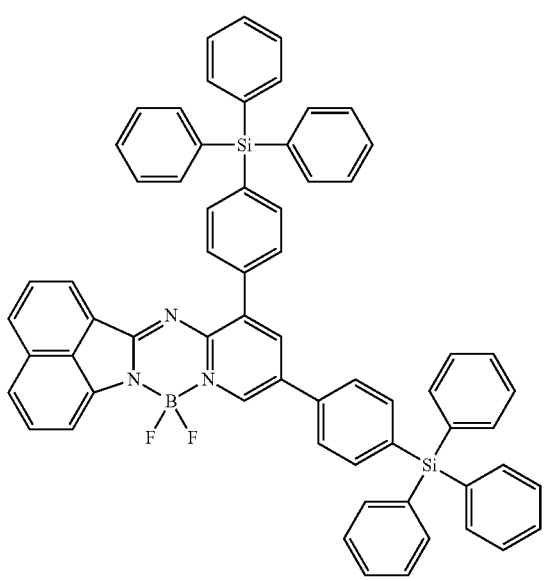
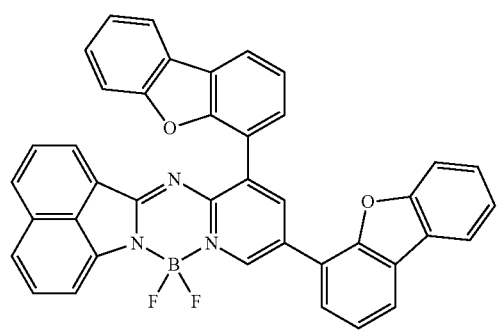
102
-continued
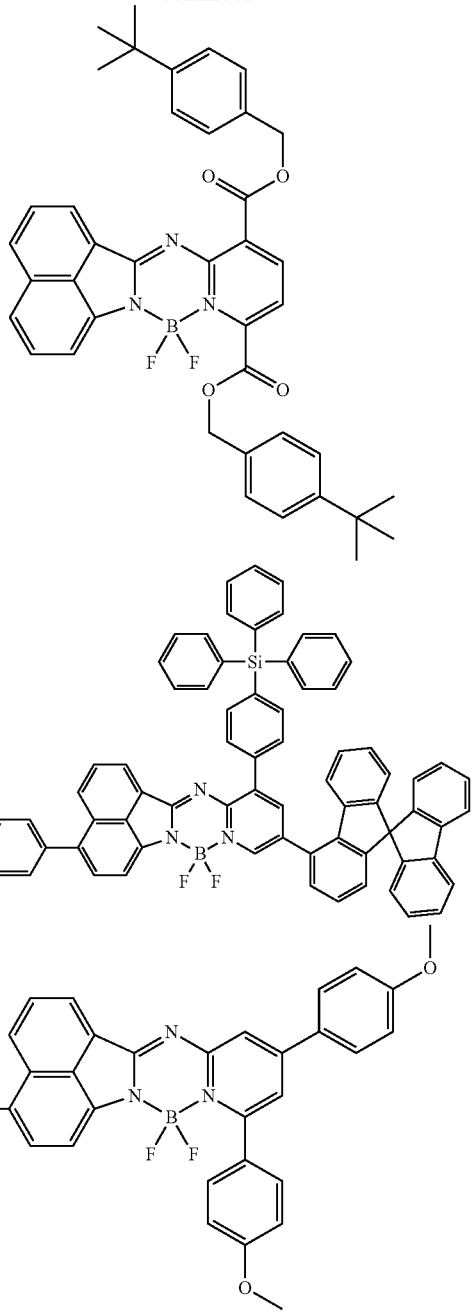
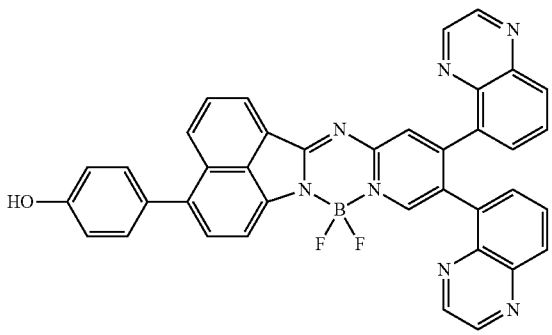

103
-continued
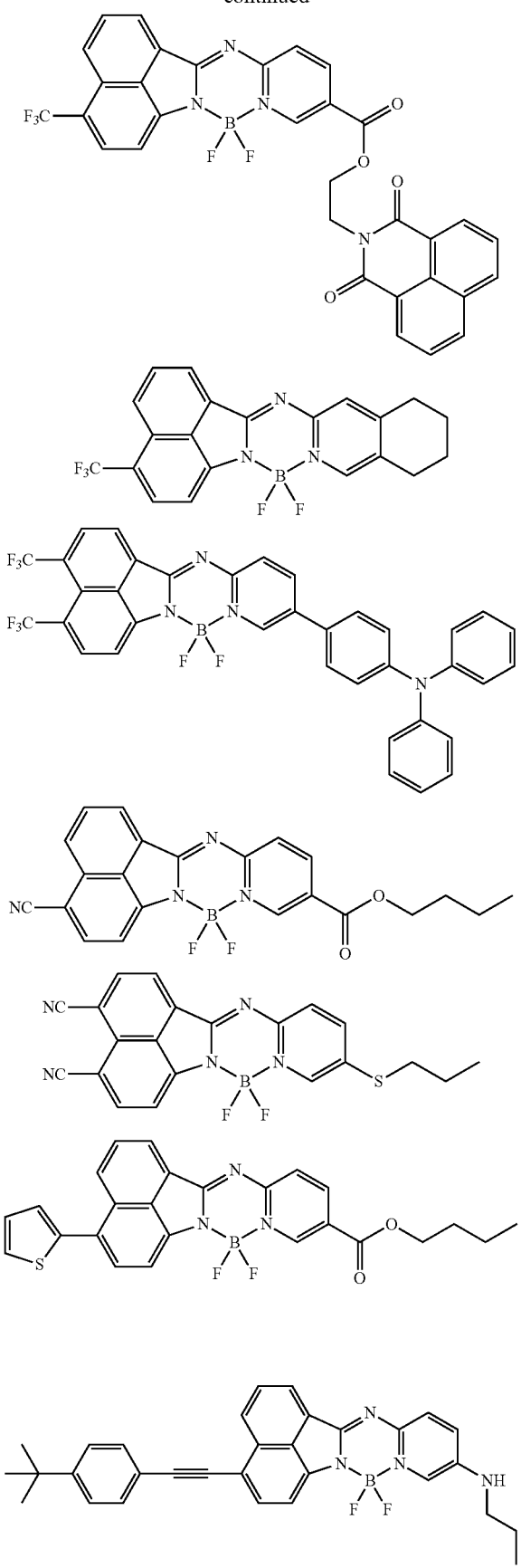
104
-continued
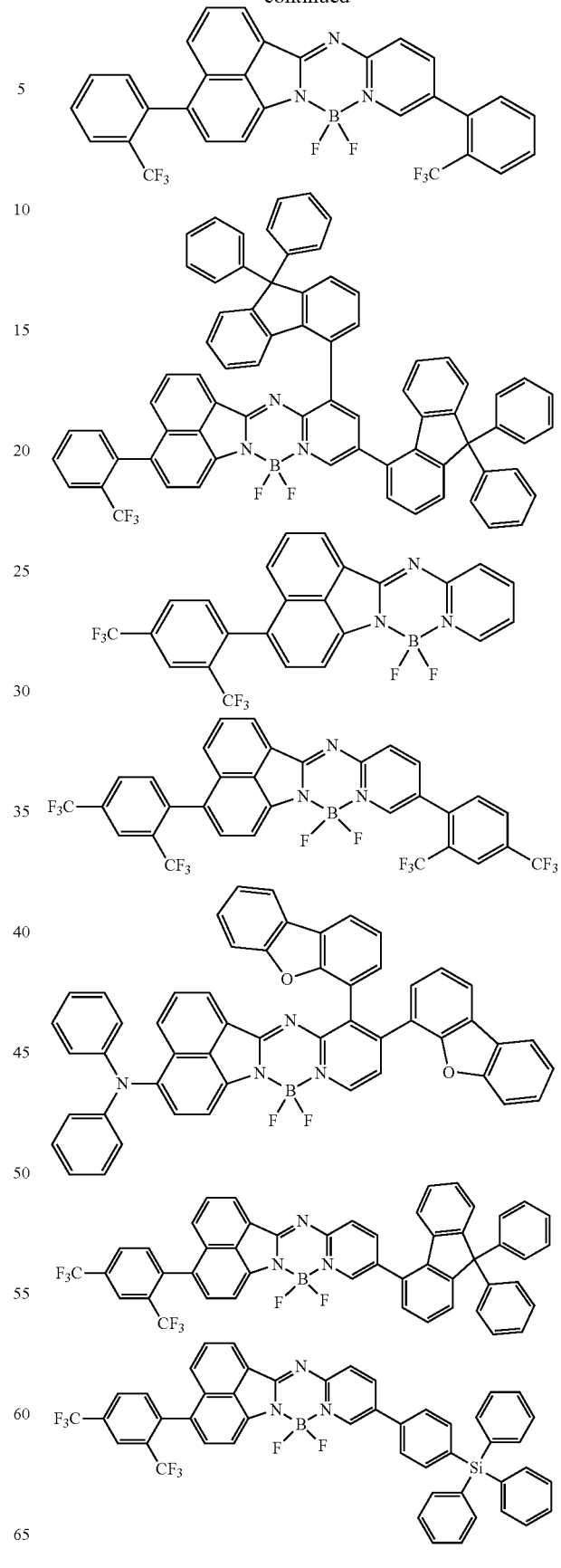

105 106
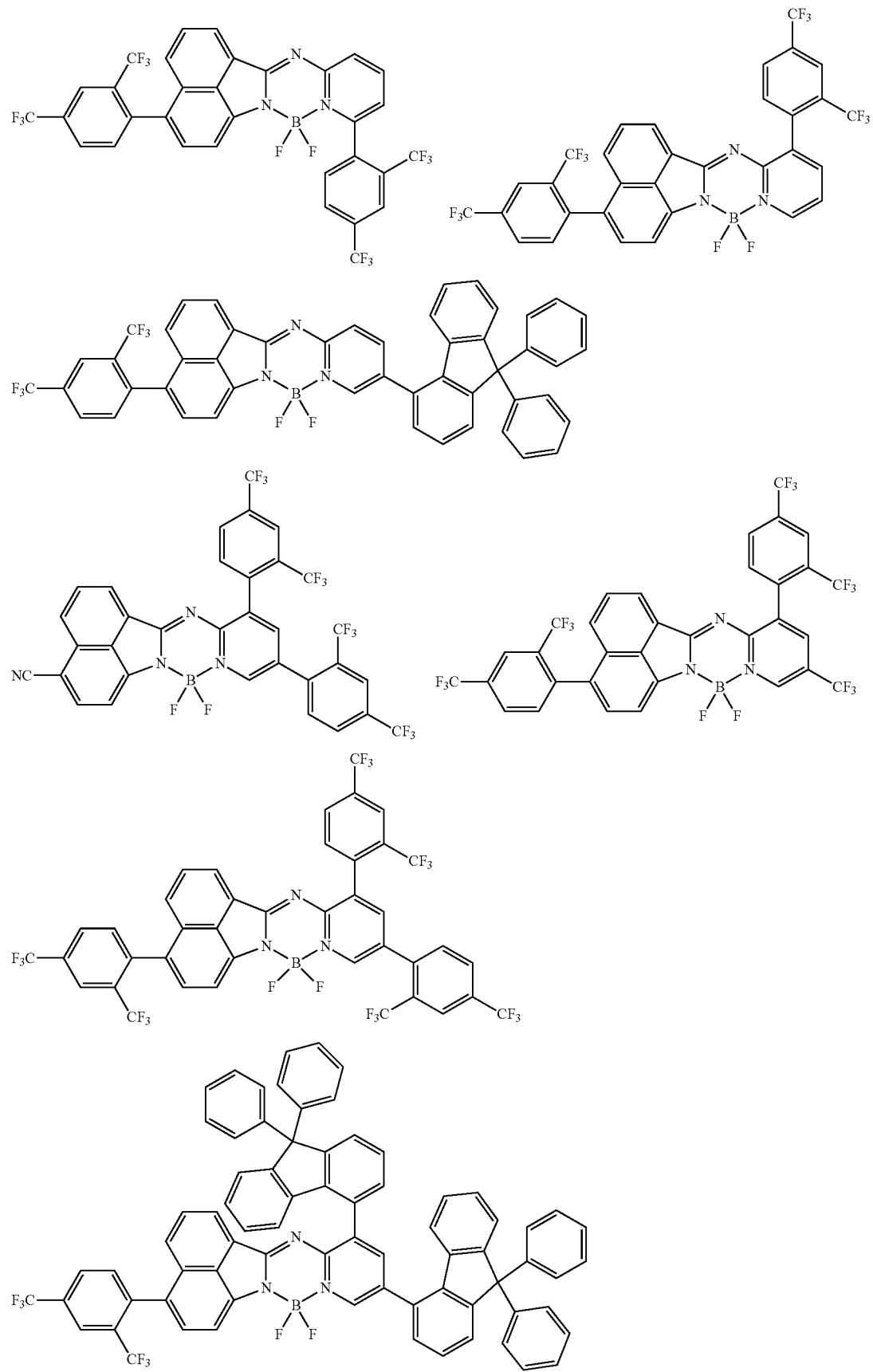

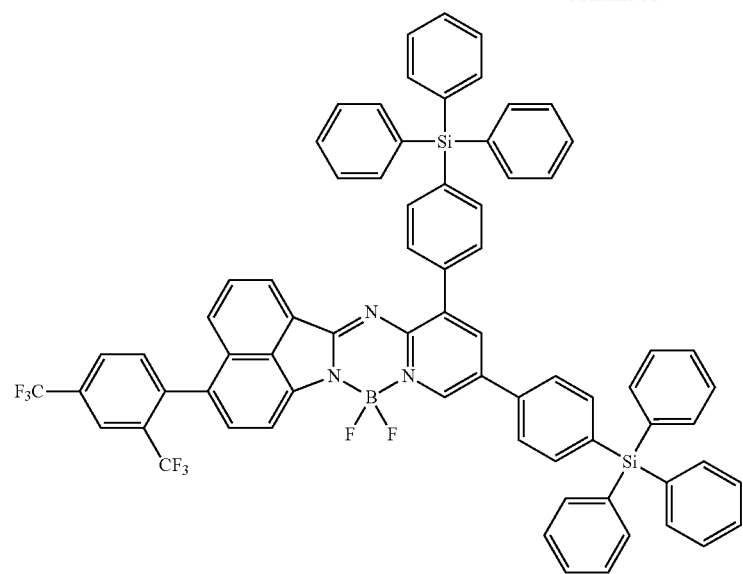
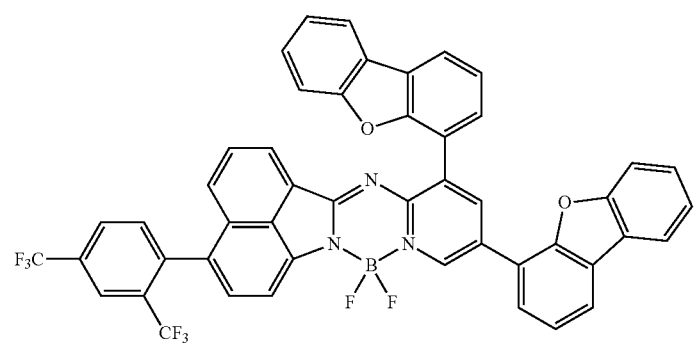
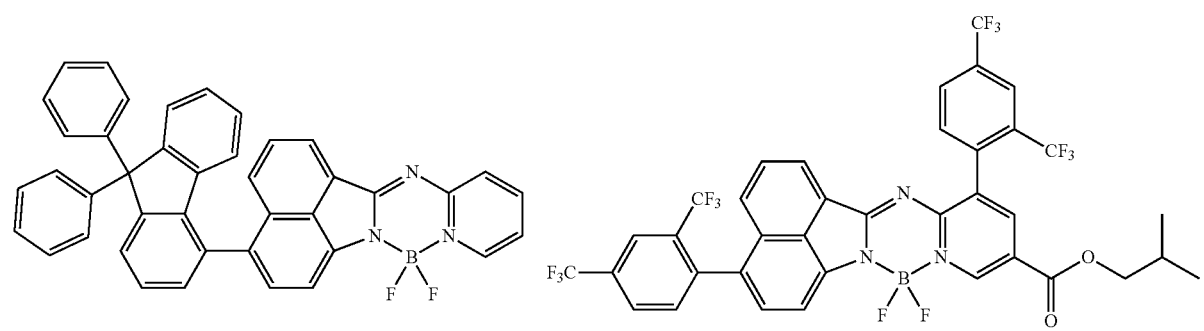
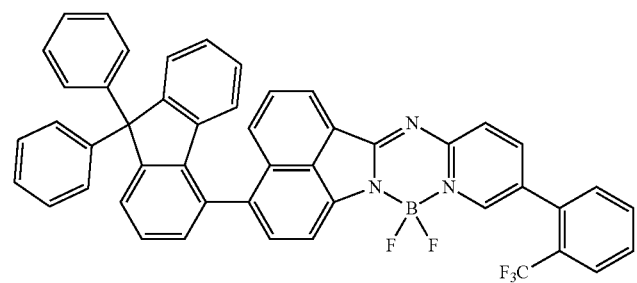

-continued
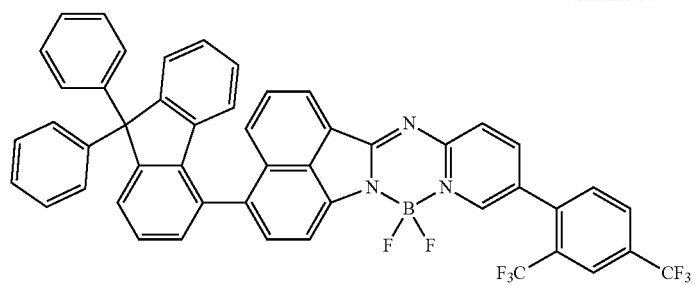
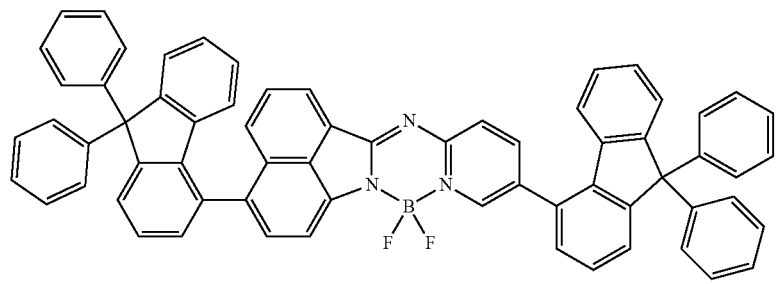
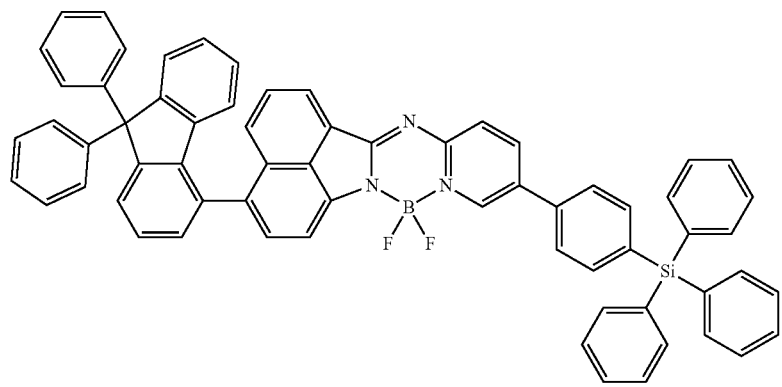
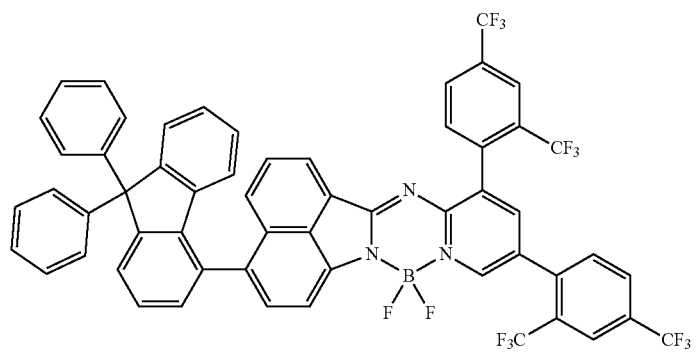

-continued
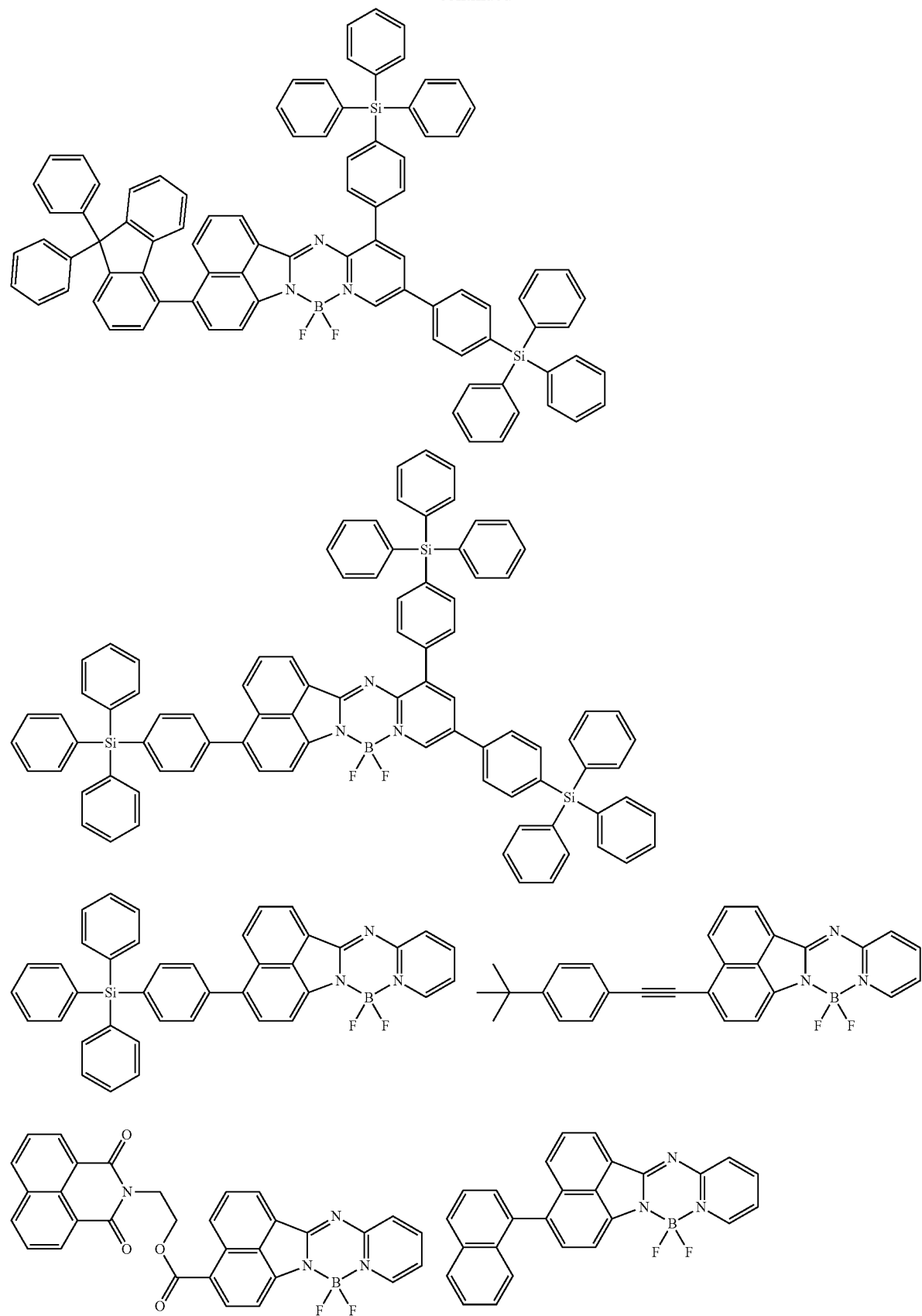

[Chemical Formula 2]

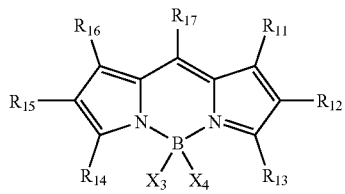

in the Chemical Formula 2, $X_3$ and $X_4$ are the same as or different from each other, and each independently a halogen group; a cyano group; a hydroxyl group; —$OR_A$; —C(=O)$OR_B$; —OC(=O)$R_C$; a substituted or unsubstituted C2 to C30 alkynyl group; or a substituted or unsubstituted C6 to C30 aryl group;

$R_{11}$ to $R_{16}$ are the same as or different from each other, and each independently hydrogen; deuterium; a halogen group; a cyano group; —$OR_D$; —C(=O)$OR_E$; —$SR_F$; —S(=O)2$OR_J$; a substituted or unsubstituted amine group; a substituted or unsubstituted silyl group; a substituted or unsubstituted C1 to C30 alkyl group; a substituted or unsubstituted C2 to C30 alkenyl group; a substituted or unsubstituted C2 to C30 alkynyl group; a substituted or unsubstituted C3 to C30 cycloalkyl group; a substituted or unsubstituted C6 to C30 aryl group; a substituted or unsubstituted C2 to C30 heteroaryl group; or a substituted or unsubstituted coumarin group, or adjacent groups bond to each other to form a ring;

$R_{17}$ is hydrogen; deuterium; a halogen group; a cyano group; —$OR_D$; —C(=O)$OR_E$; —$SR_F$; a substituted or unsubstituted amine group; a substituted or unsubstituted C1 to C30 alkyl group; a substituted or unsubstituted cyclohexyl group; a substituted or unsubstituted C6 to C30 aryl group; a substituted or unsubstituted C2 to C30 heteroaryl group; or a substituted or unsubstituted coumarin group; and $R_A$ to $R_F$, $R_I$ and $R_J$ are the same as or different from each other, and each independently a substituted or unsubstituted alkyl group; a substituted or unsubstituted aryl group; a substituted or unsubstituted heteroaryl group; a substituted or unsubstituted coumarin group; or a substituted or unsubstituted naphthalimide group.

2. The color conversion composition of claim 1, wherein the compound selected from any one of the compounds in the Group I has a maximum absorption wavelength in a wavelength region of 400 nm to 500 nm.

3. The color conversion composition of claim 1, wherein the compound represented by the Chemical Formula 2 has a maximum emission wavelength in a wavelength region of 500 nm to 650 nm.

4. The color conversion composition of claim 1, wherein $X_3$ and $X_4$ are the same as or different from each other, and each independently a halogen group; a cyano group; a hydroxyl group; —$OR_A$; —OC(=O)$R_C$; a substituted or unsubstituted ethynyl group; a substituted or unsubstituted naphthyl group; or a substituted or unsubstituted perylenyl group; and $R_A$ and $R_C$ have the same definitions as in the Chemical Formula 2.

5. The color conversion composition of claim 1, wherein $R_{17}$ is hydrogen; deuterium; a halogen group; a cyano group; a pyrenyl group; a pyridine group; a furan group; a thiophene group; —$OR_D$; —C(=O)$OR_E$; —$SR_F$; a substituted or unsubstituted amine group; a substituted or unsubstituted methyl group; a substituted or unsubstituted cyclohexyl group; a substituted or unsubstituted phenyl group; a substituted or unsubstituted naphthyl group; a substituted or unsubstituted fluorenyl group; a substituted or unsubstituted dibenzofuran group; a substituted or unsubstituted dibenzothiophene group; a substituted or unsubstituted carbazole group; or a substituted or unsubstituted coumarin group; and $R_D$, $R_E$ and $R_I$ have the same definitions as in the Chemical Formula 2.

6. The color conversion composition of claim 1, wherein the compound represented by the Chemical Formula 2 is any one of the following compounds:

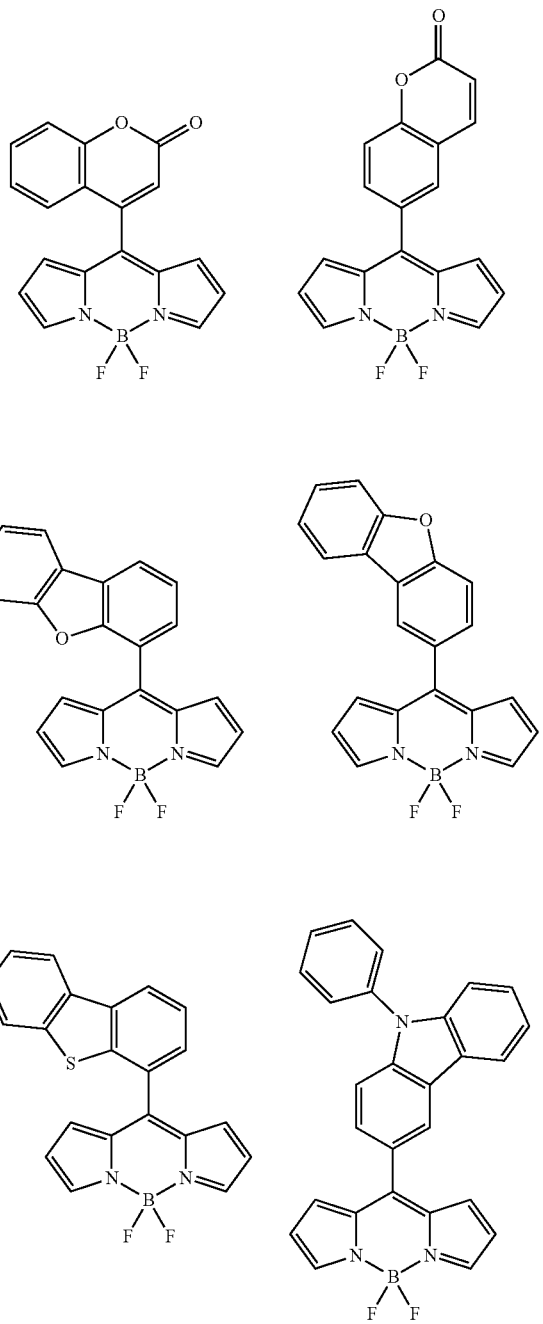

115
-continued
116
-continued
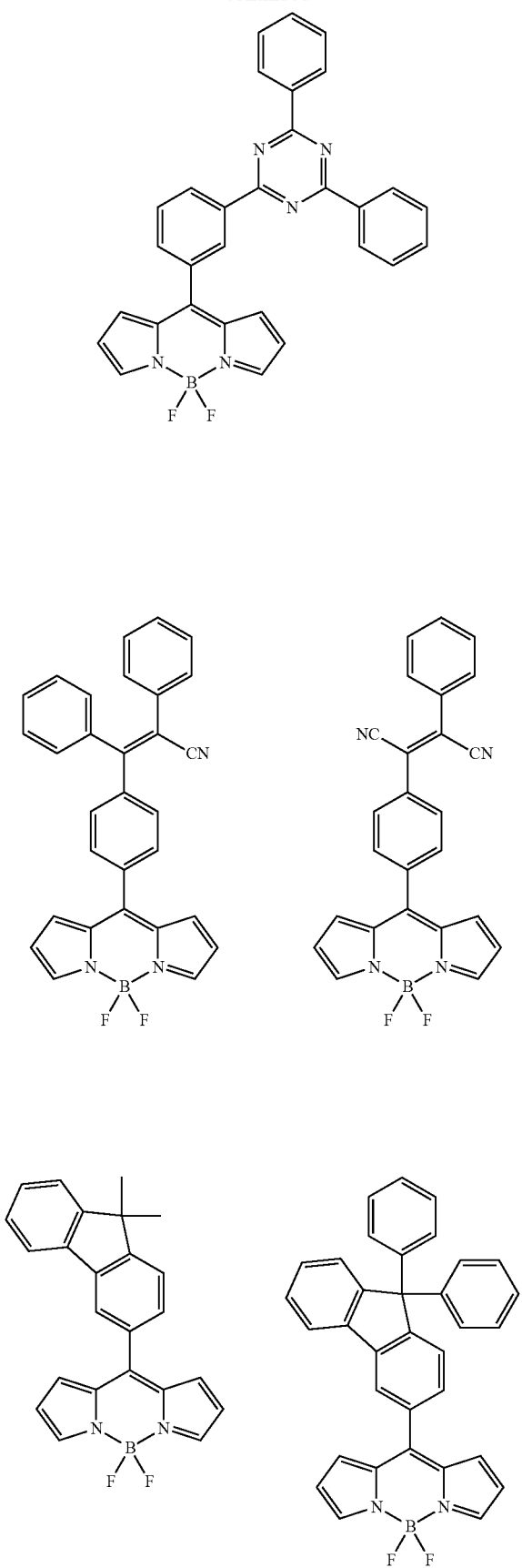
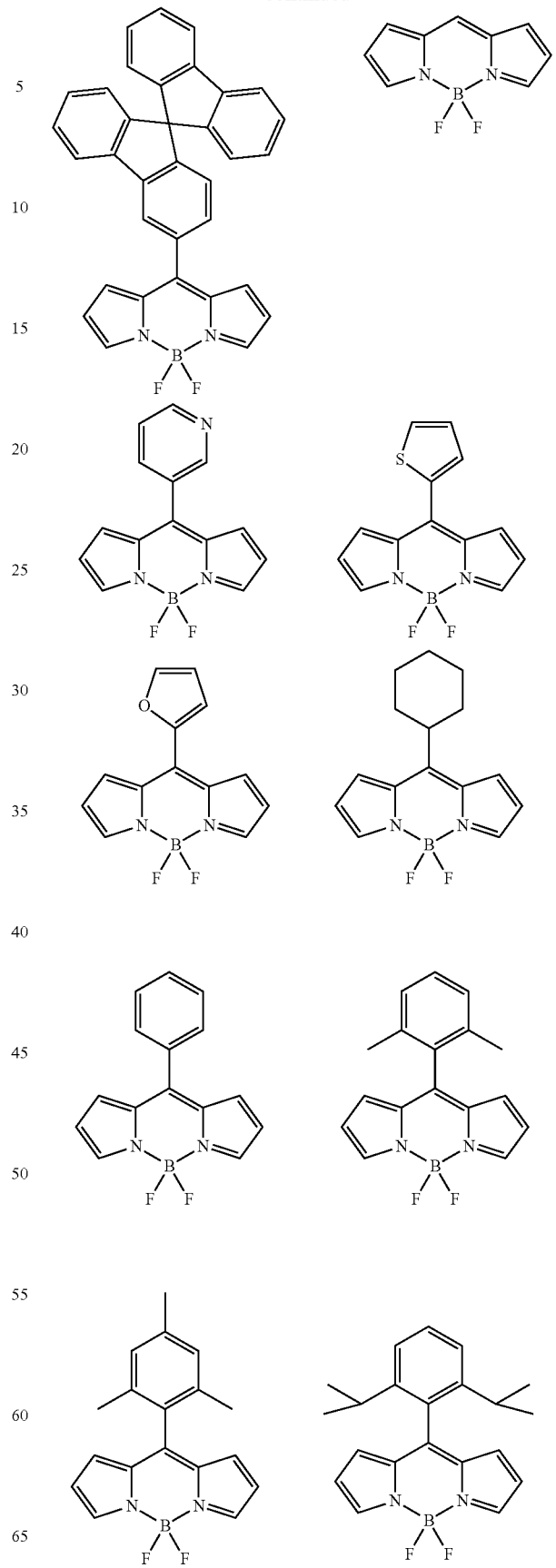

117
-continued
118
-continued
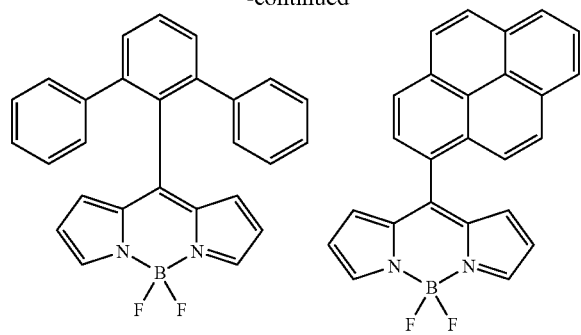
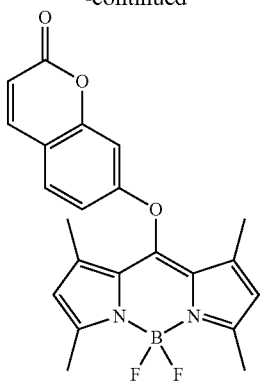
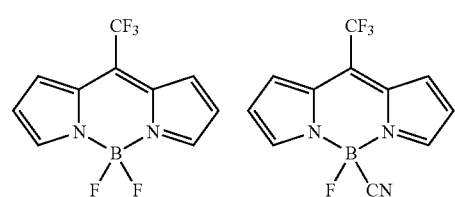
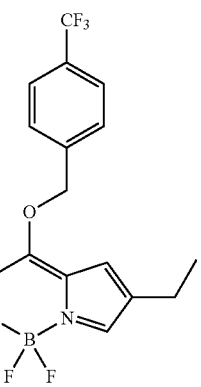
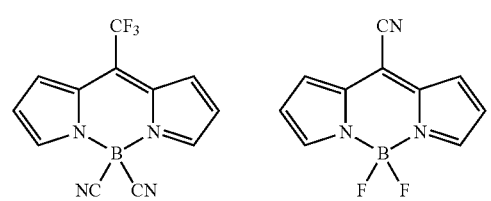
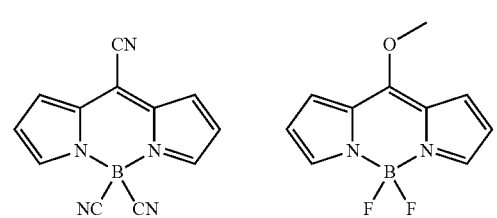
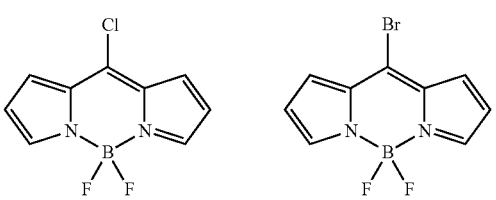
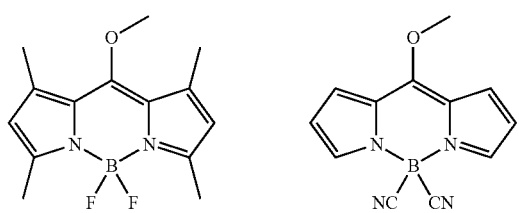
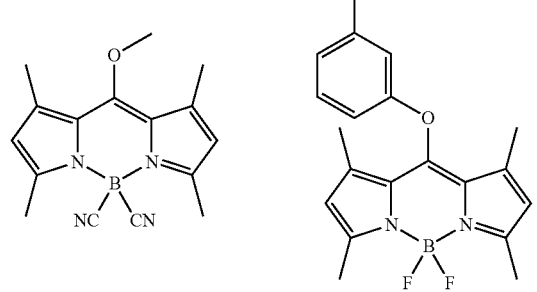
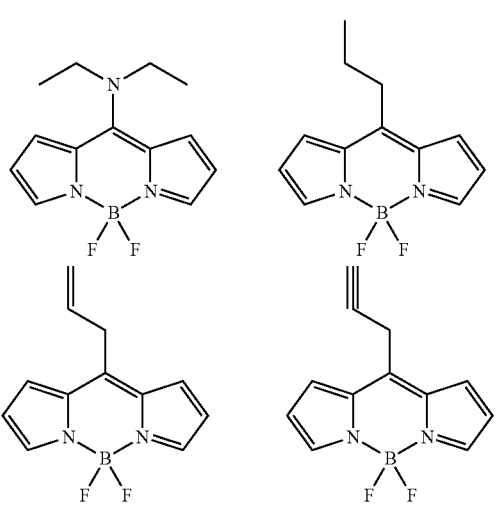

119
-continued
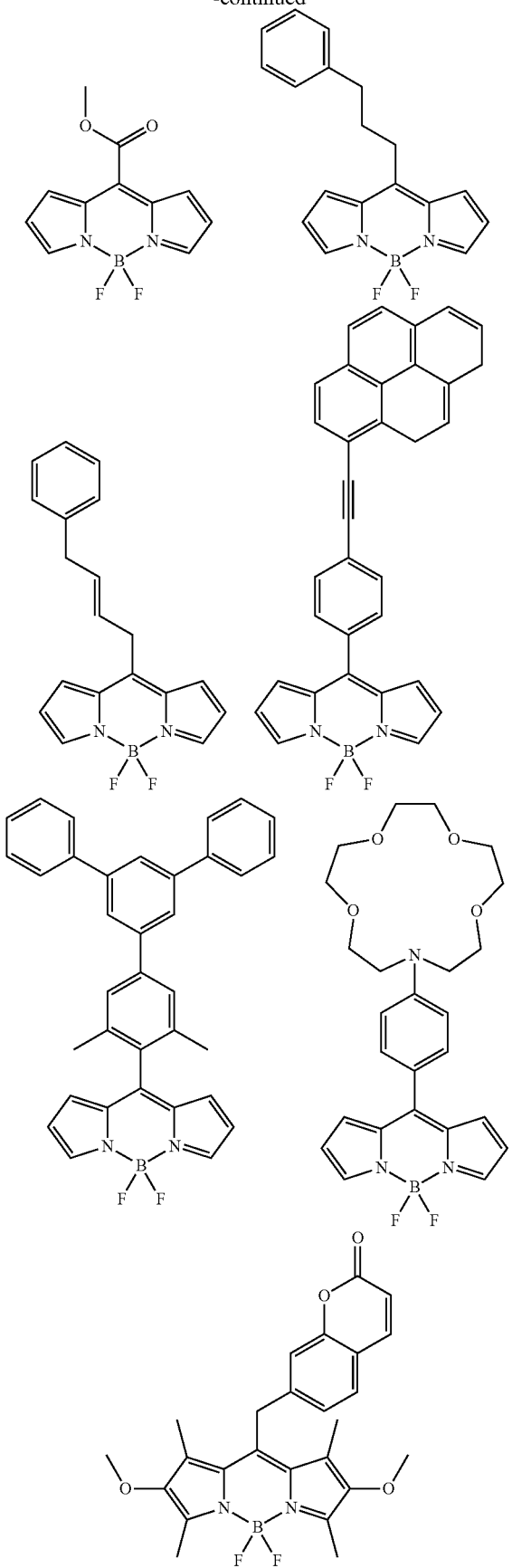
120
-continued
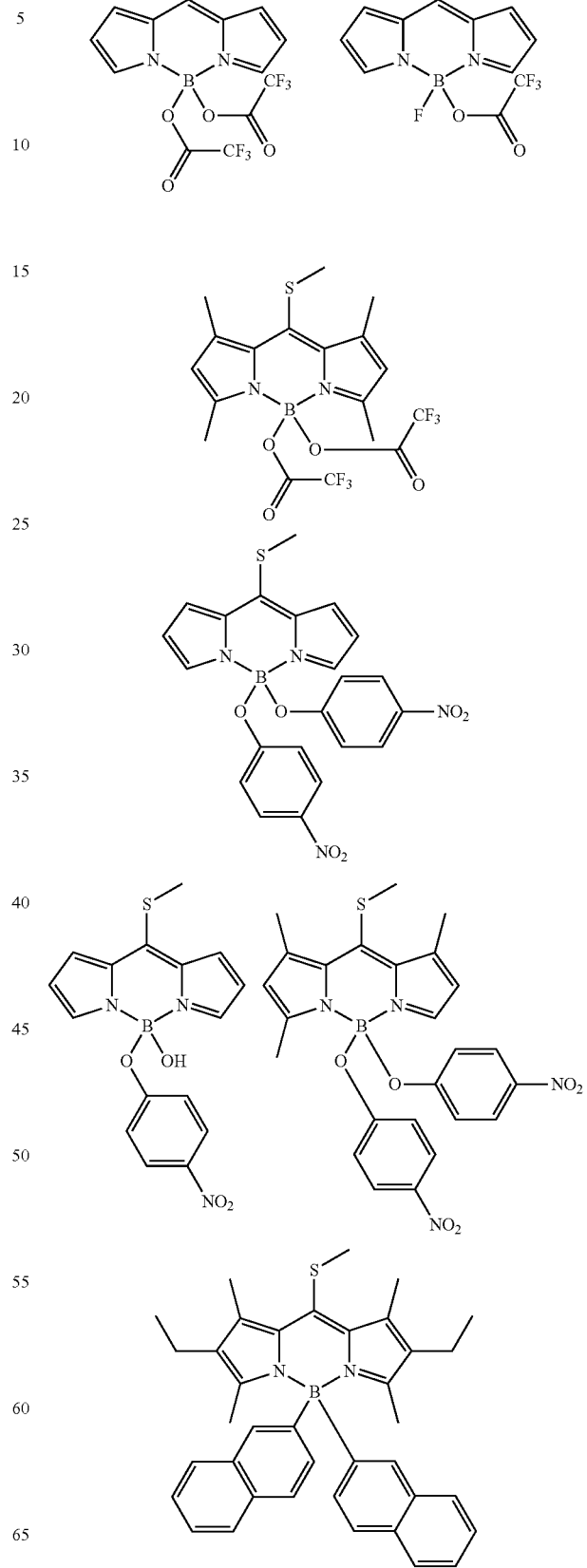

121
-continued
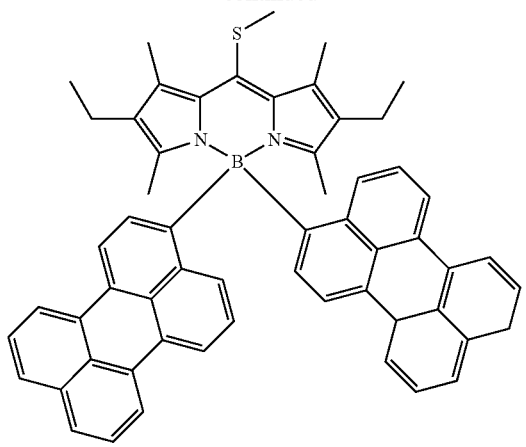
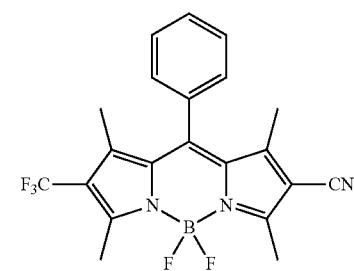
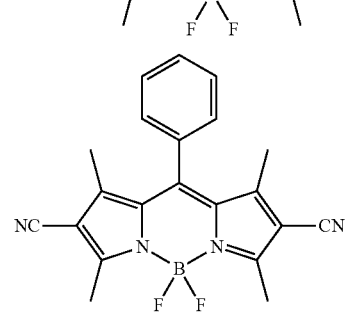
122
-continued
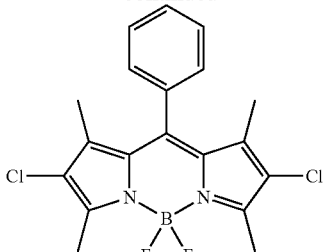
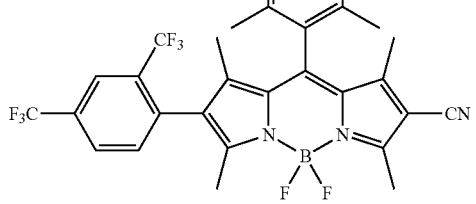
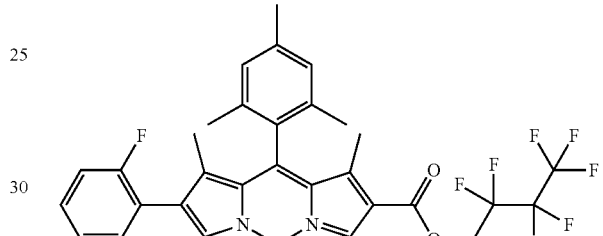
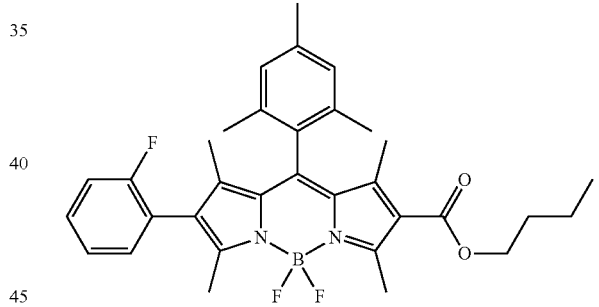
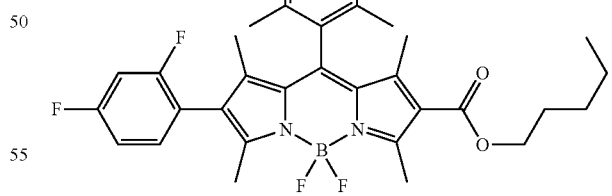

123
-continued
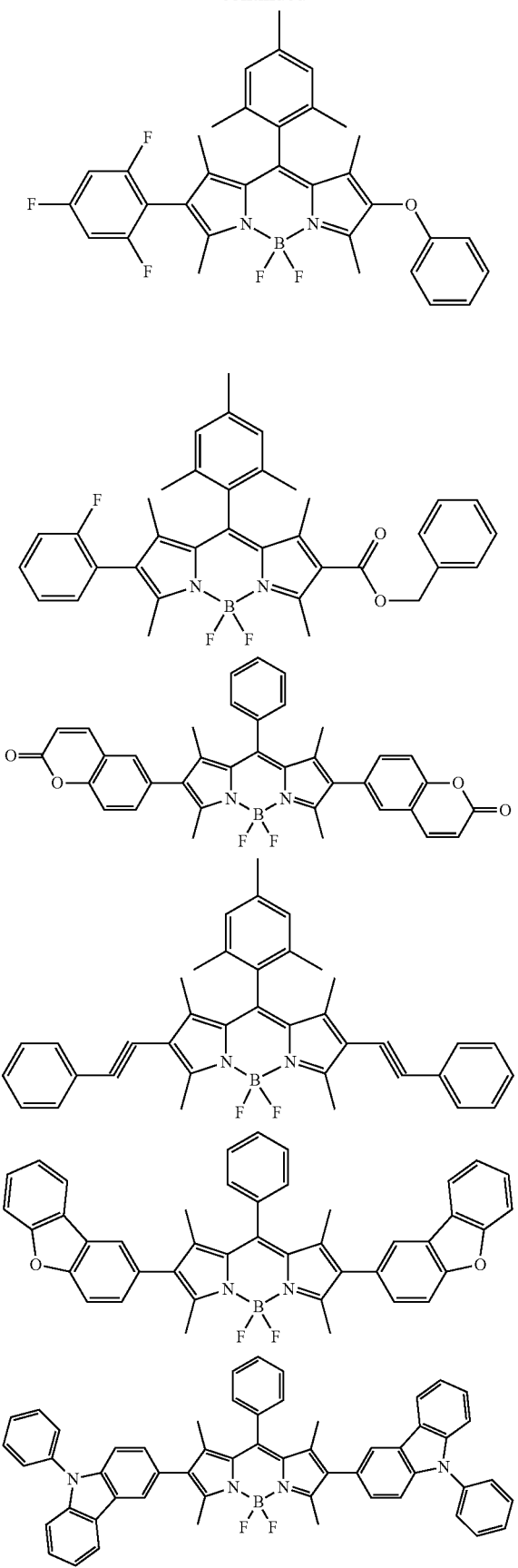
124
-continued
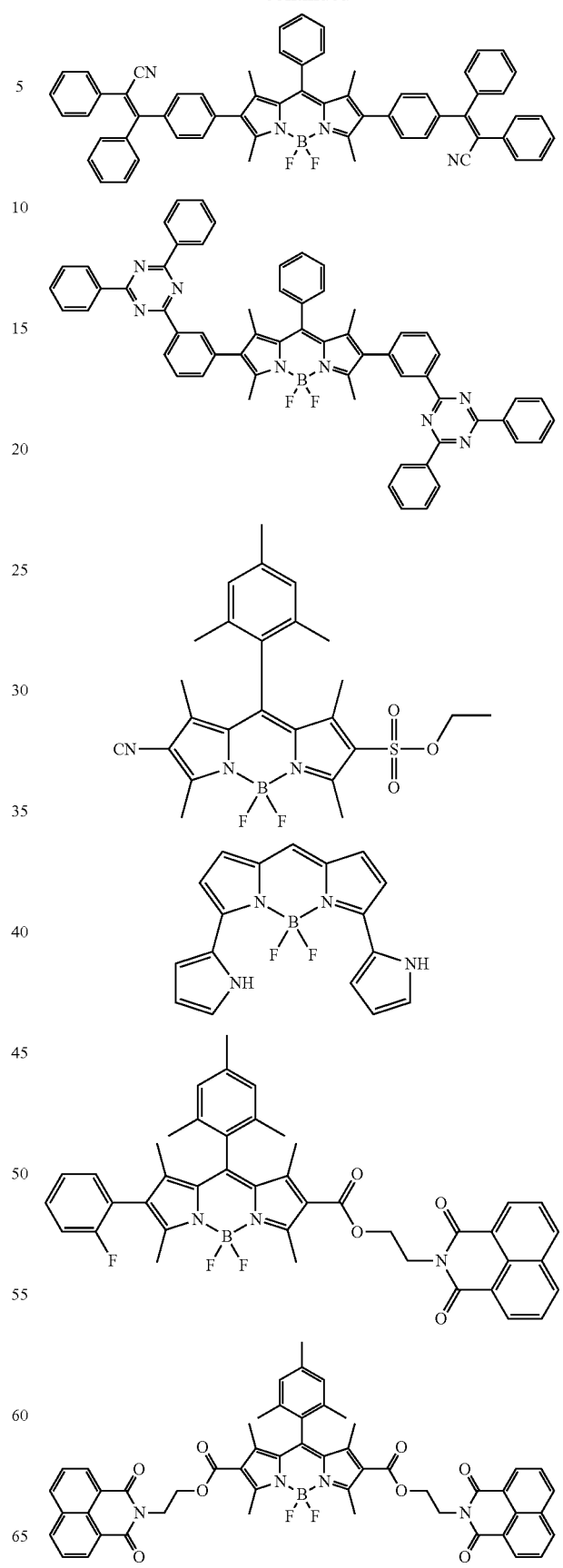

125
-continued
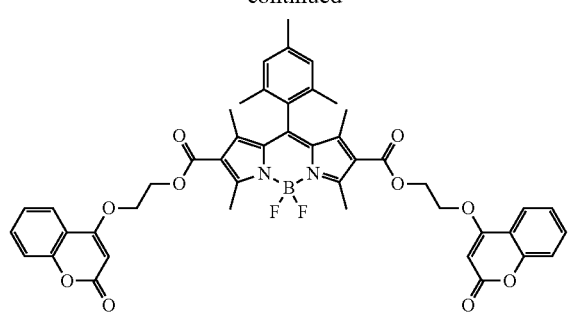
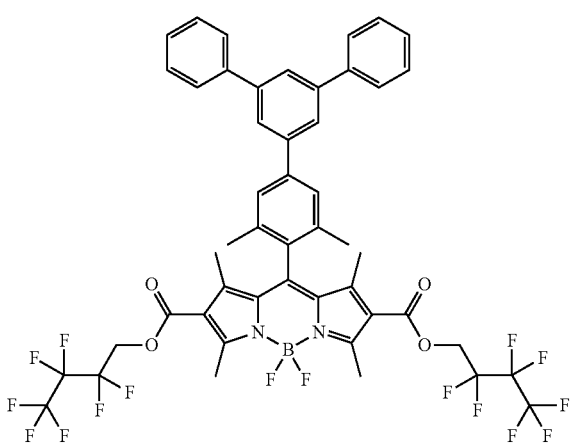
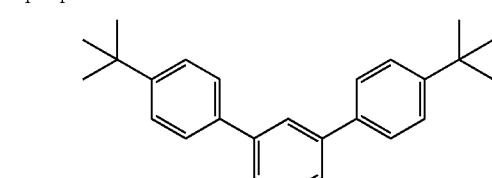
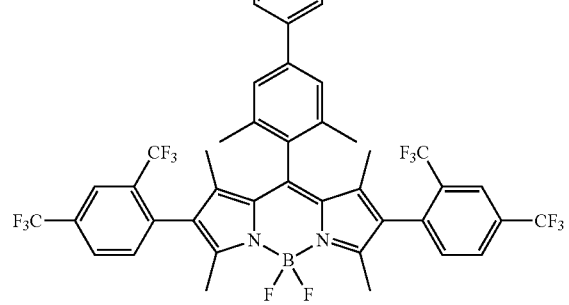
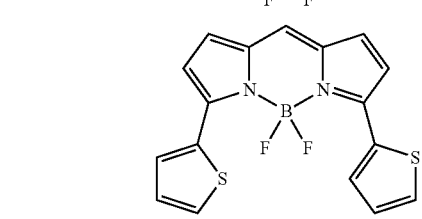
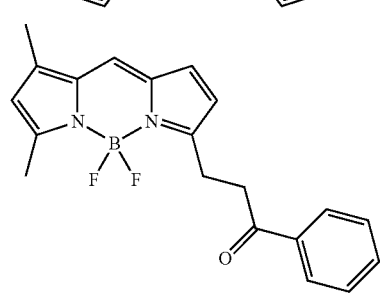
126
-continued
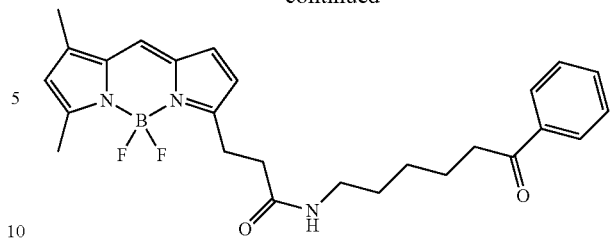
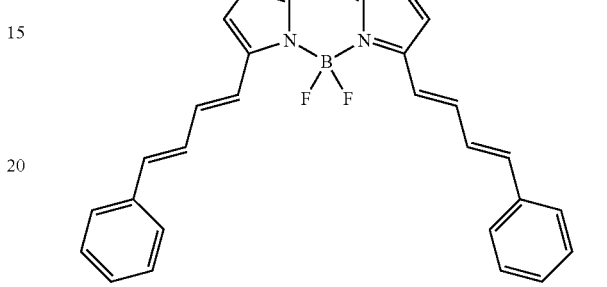
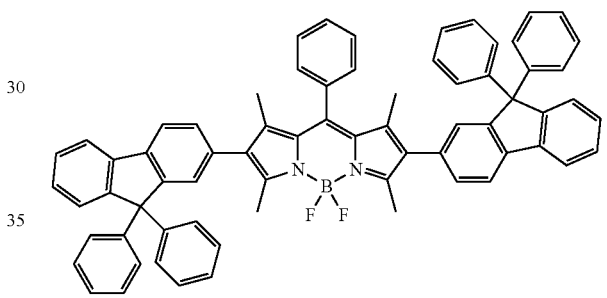
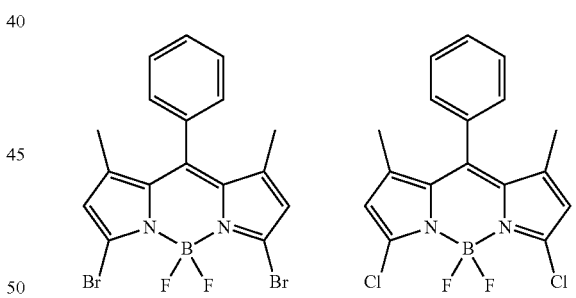

127
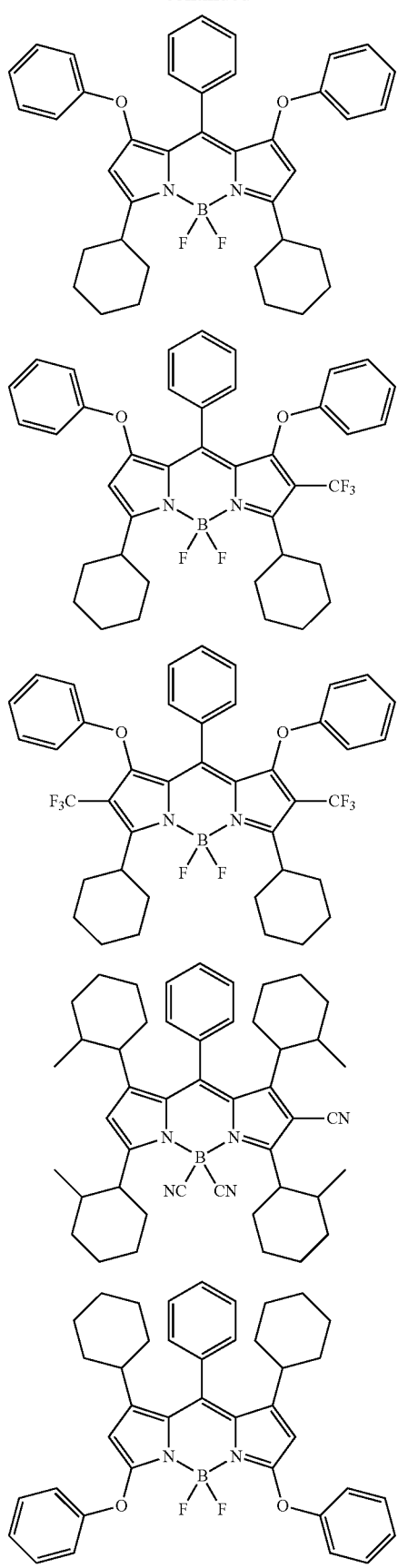
128
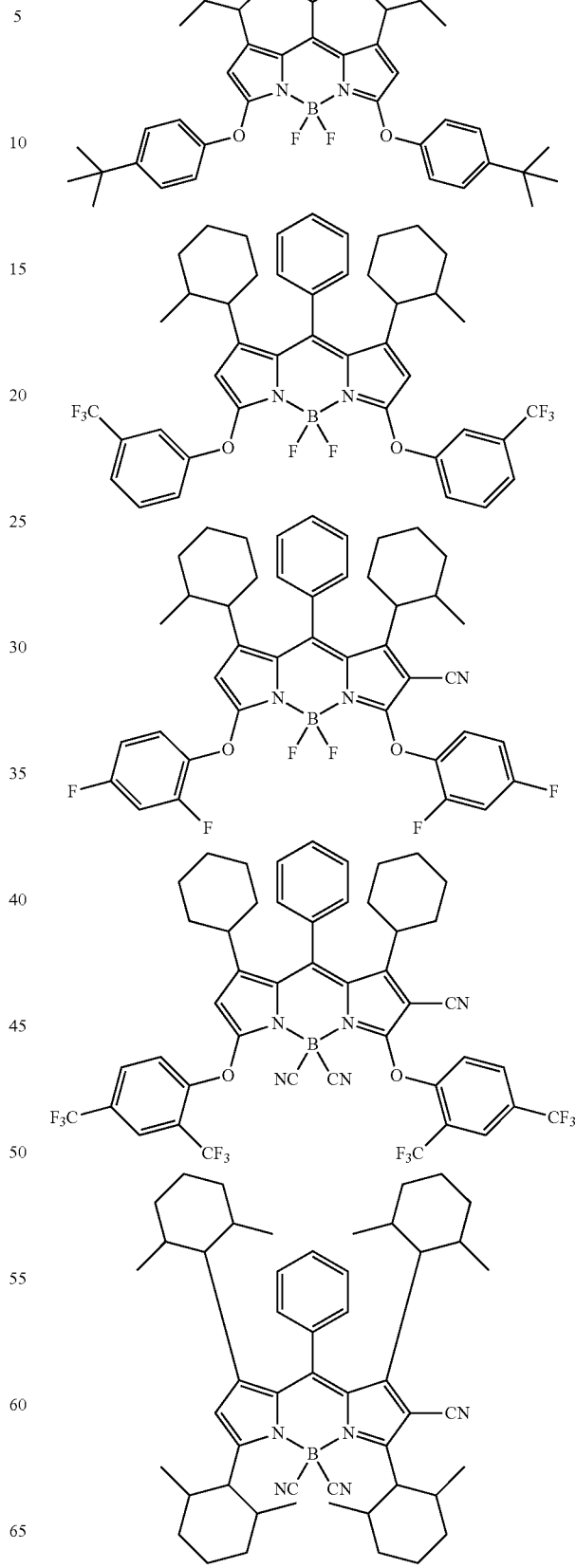

129
-continued
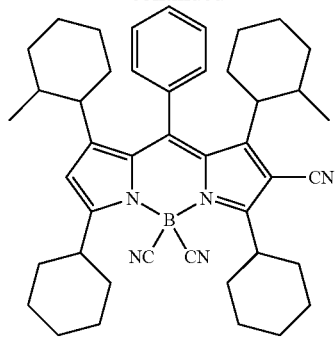
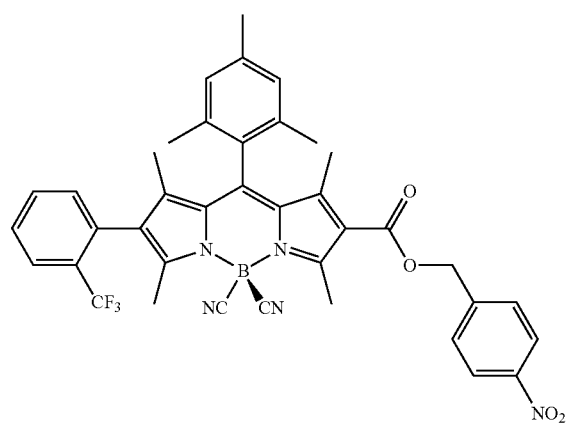
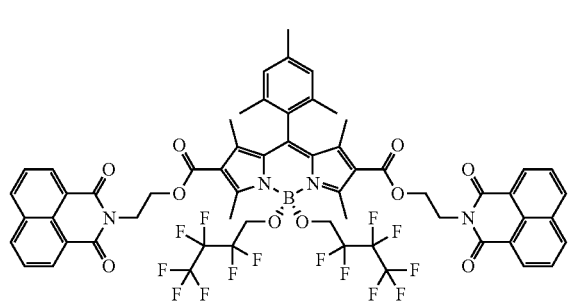
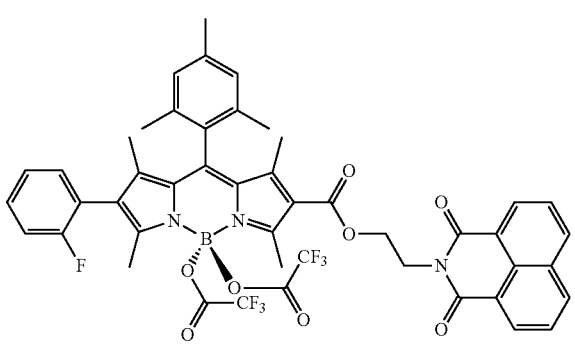
130
-continued
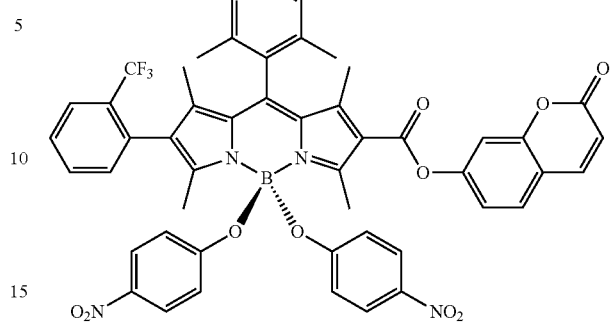
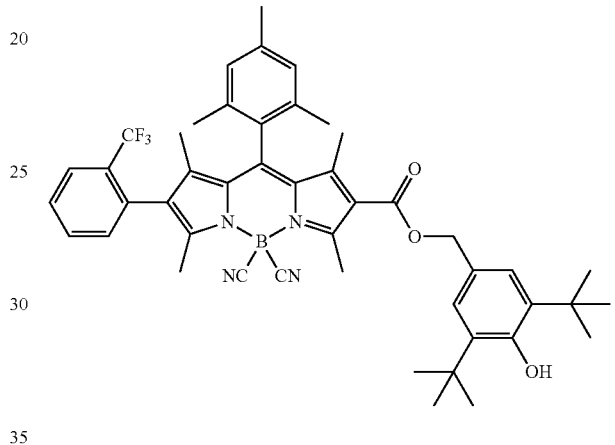
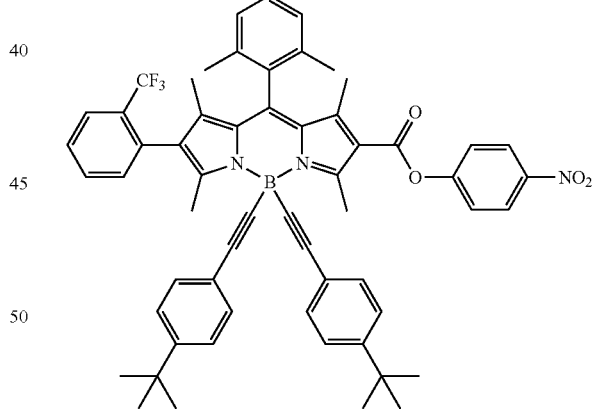
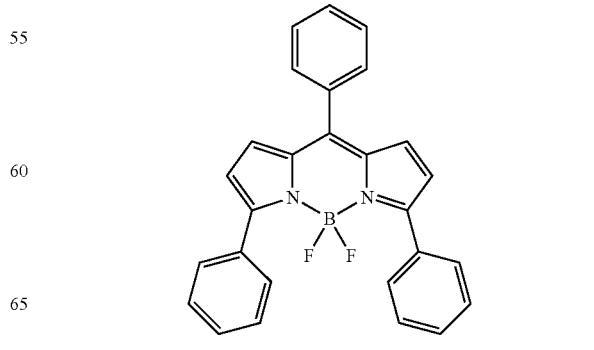

131
-continued
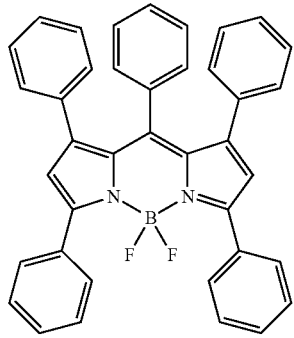
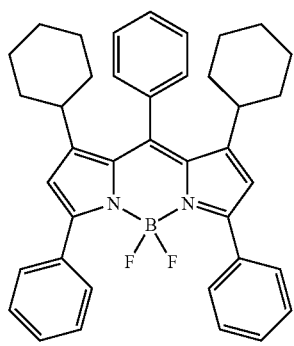
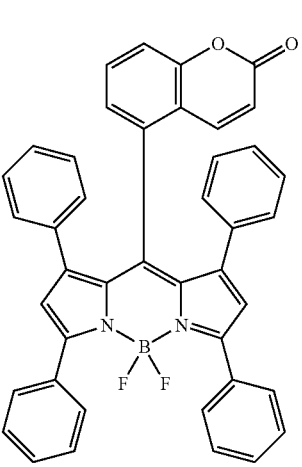
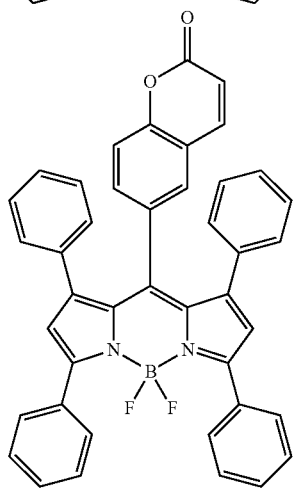
132
-continued
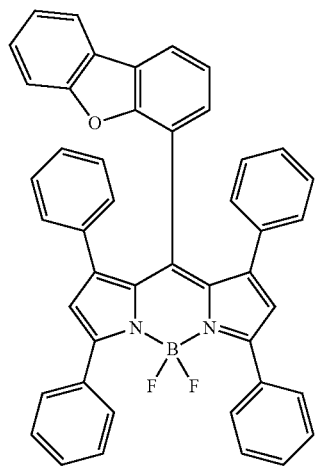
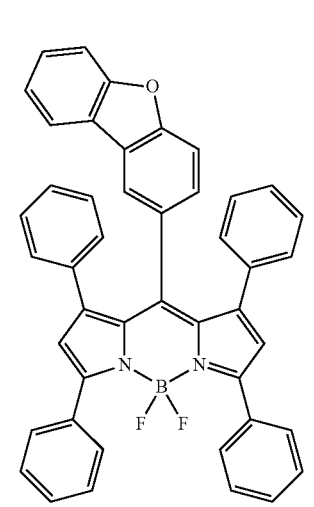
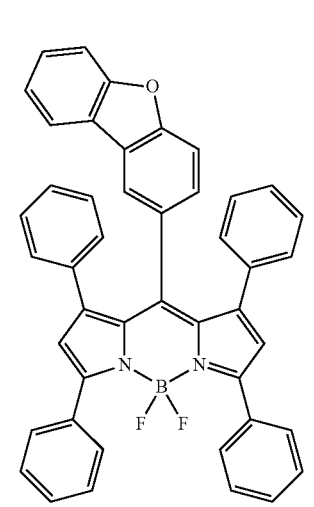

133
-continued
134
-continued
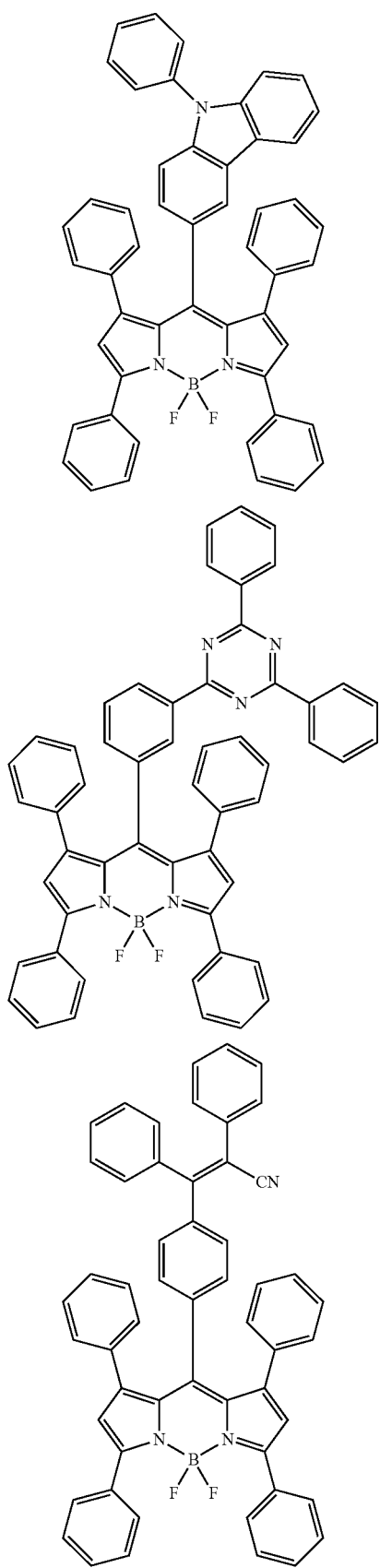
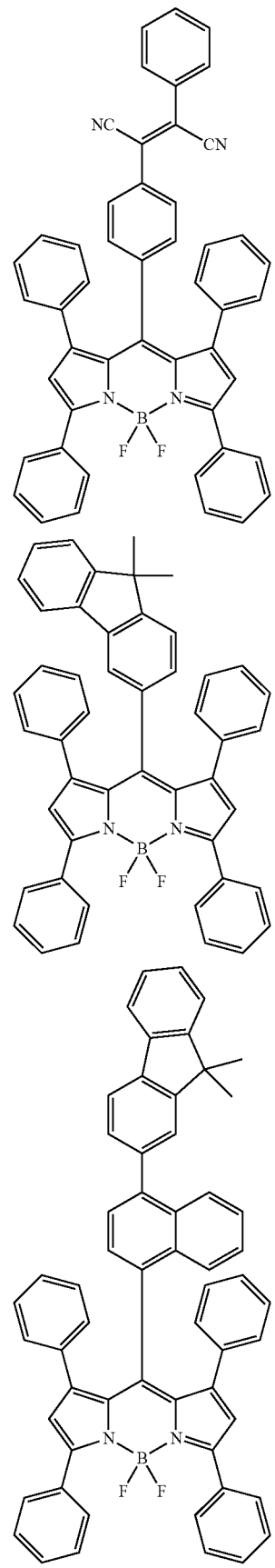

-continued
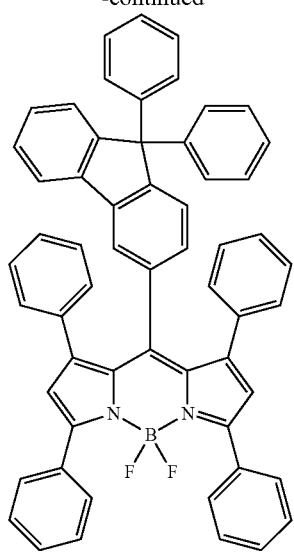
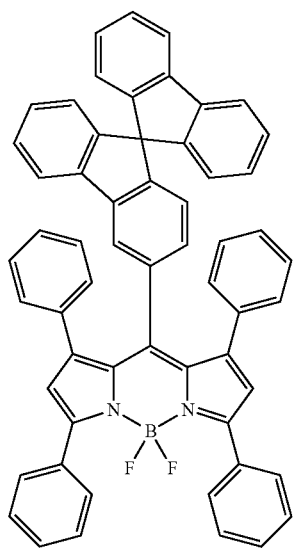
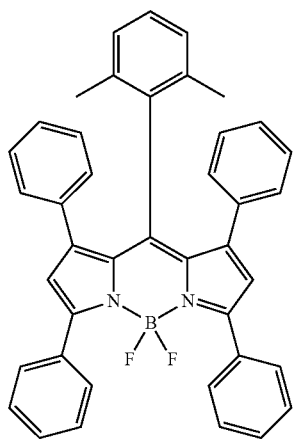
-continued
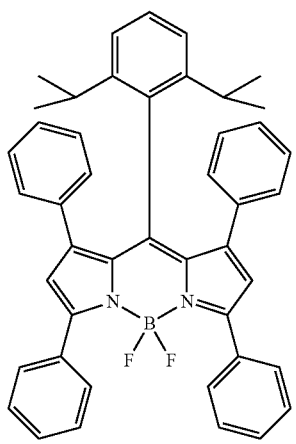
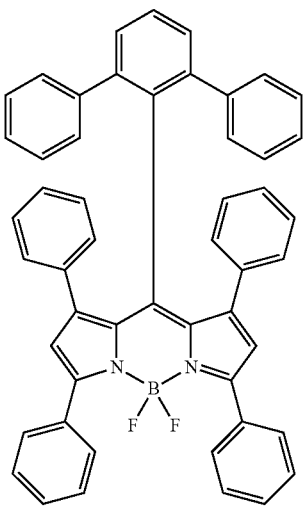
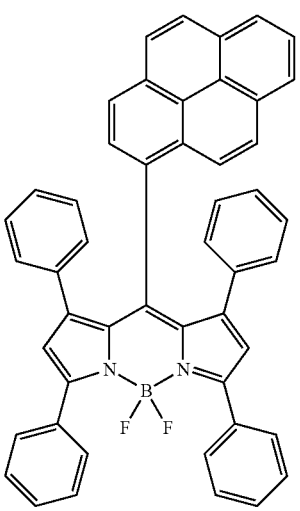

137
-continued
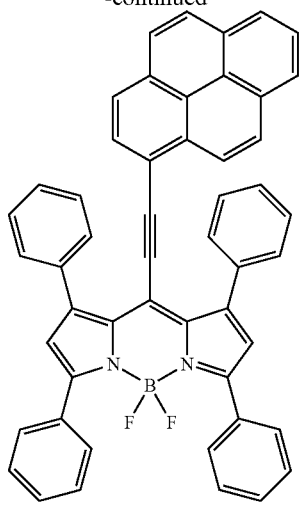
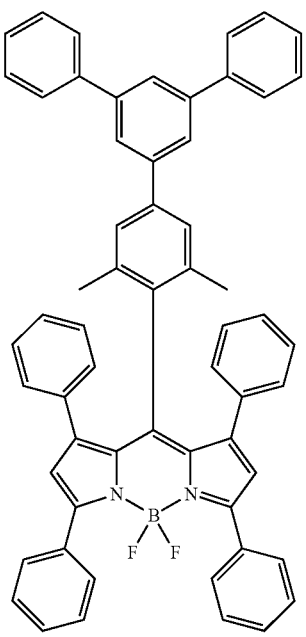
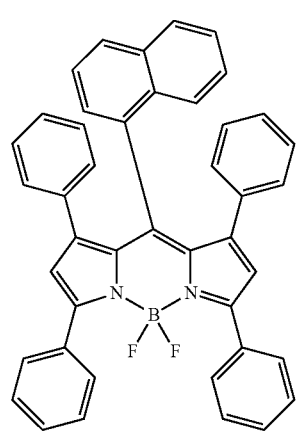
138
-continued
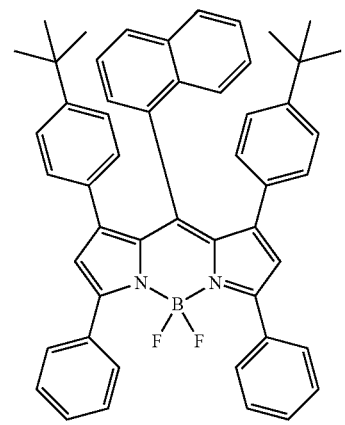
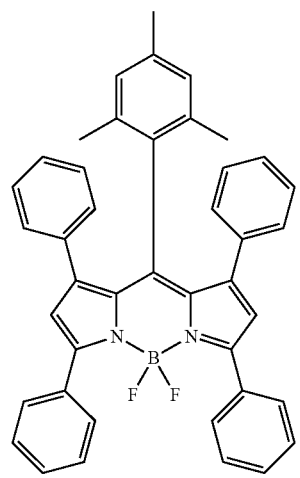

139
-continued
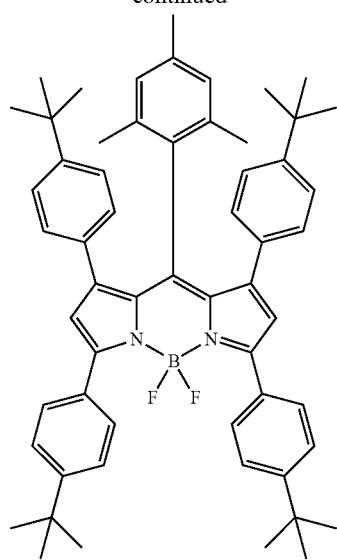
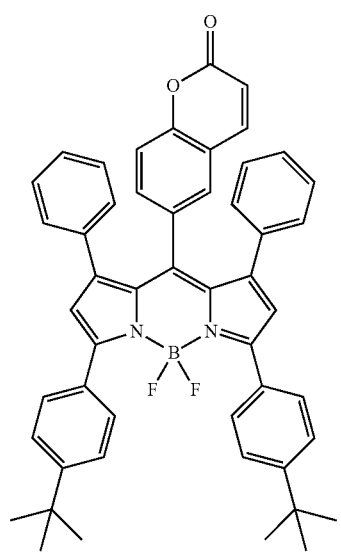
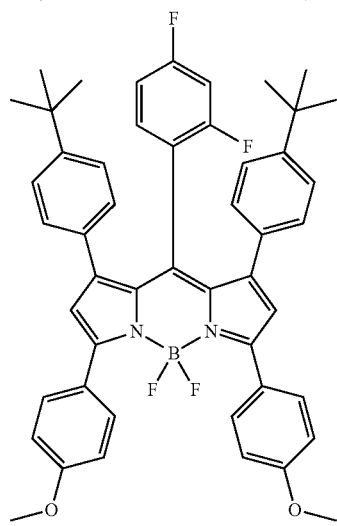
140
-continued
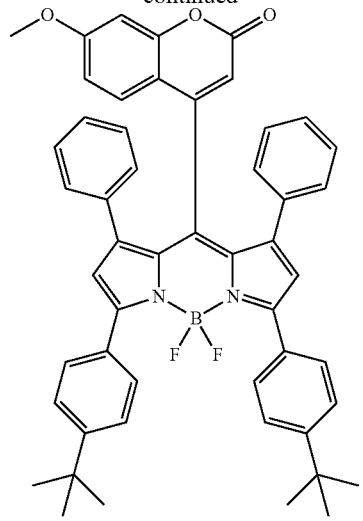
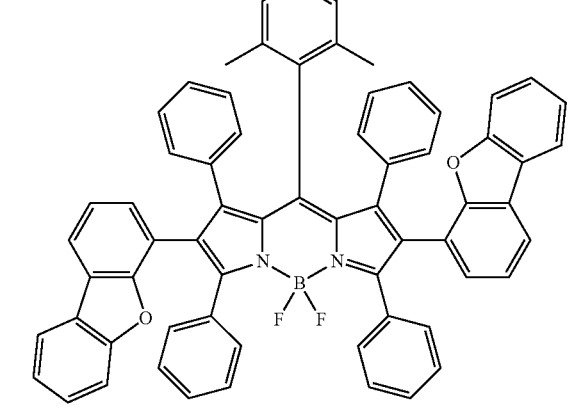
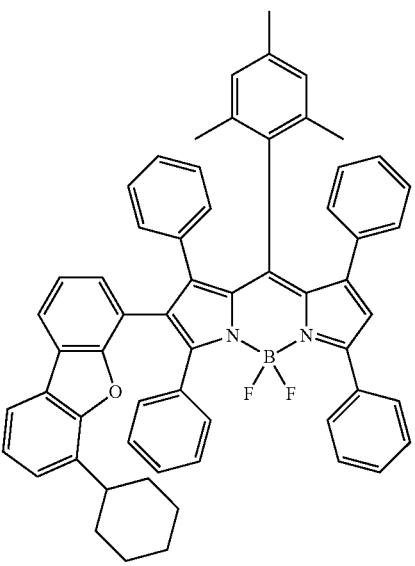

-continued
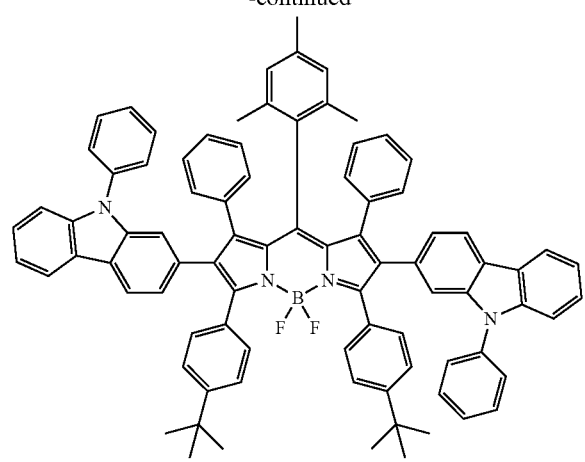
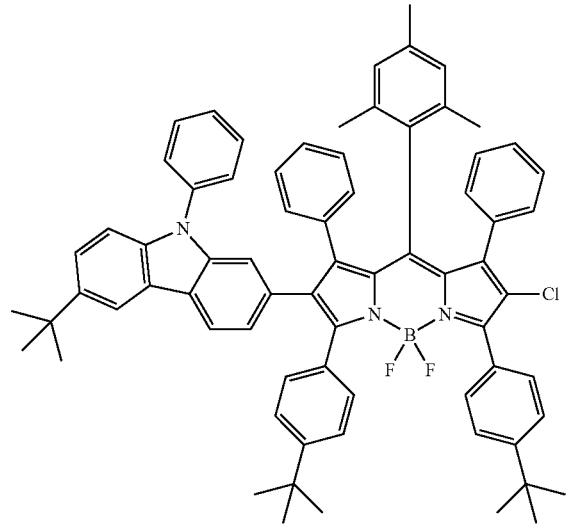
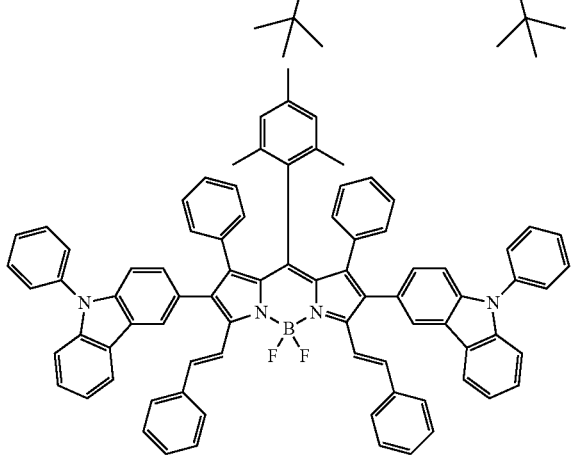
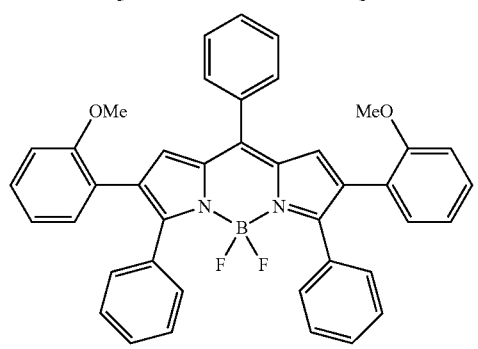
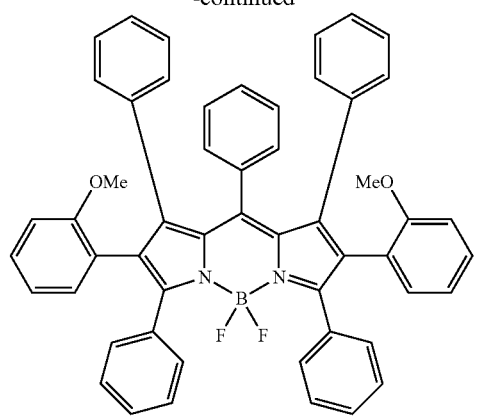
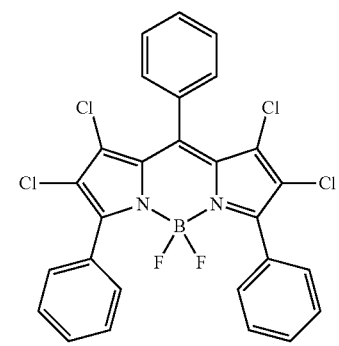
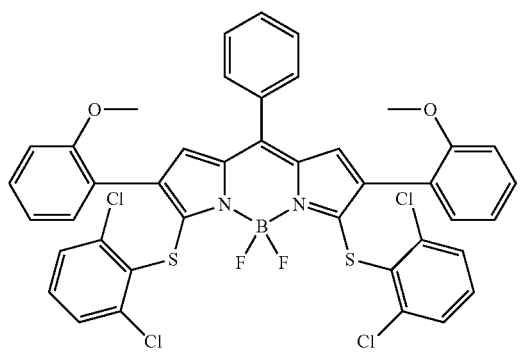
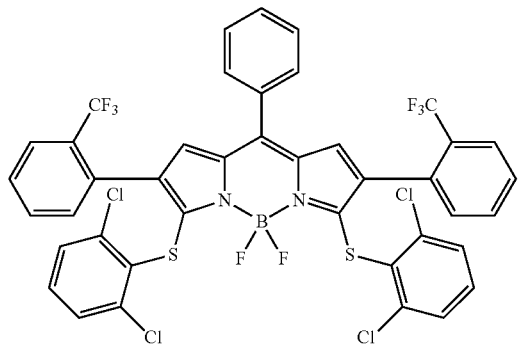

-continued
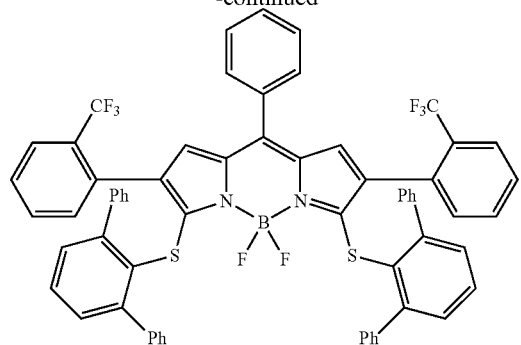
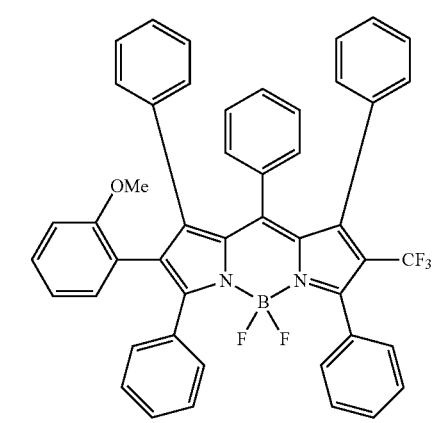
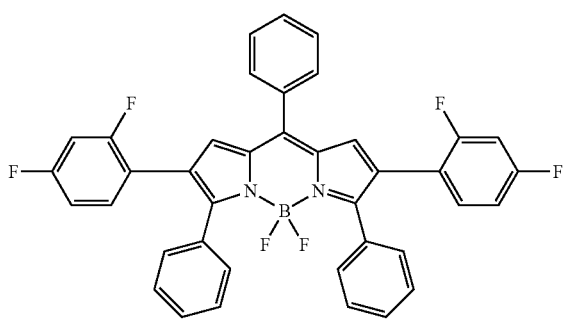
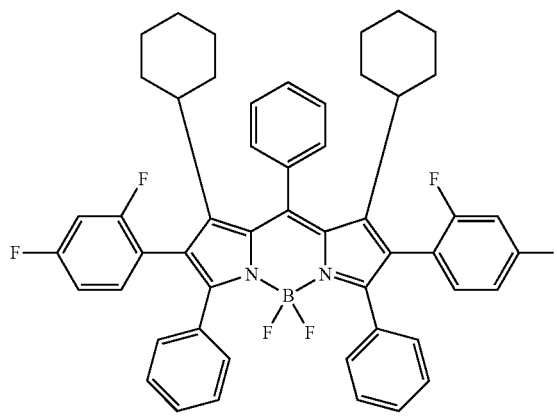
-continued
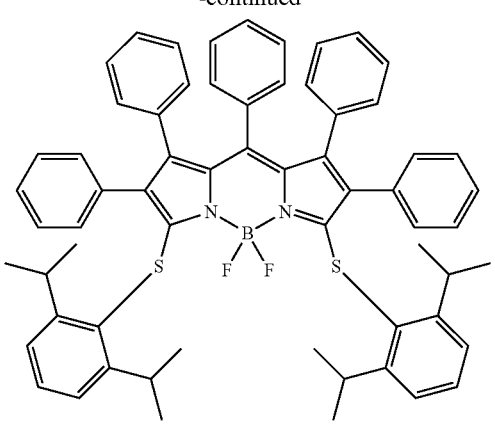
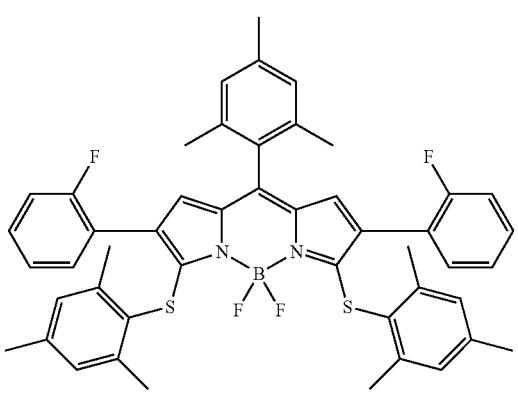
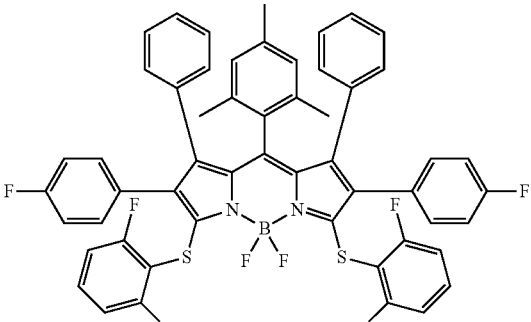
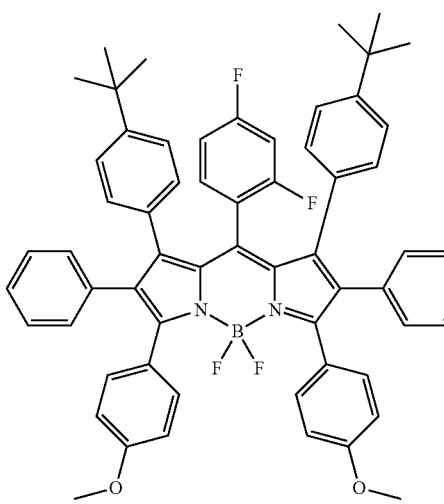

145
-continued
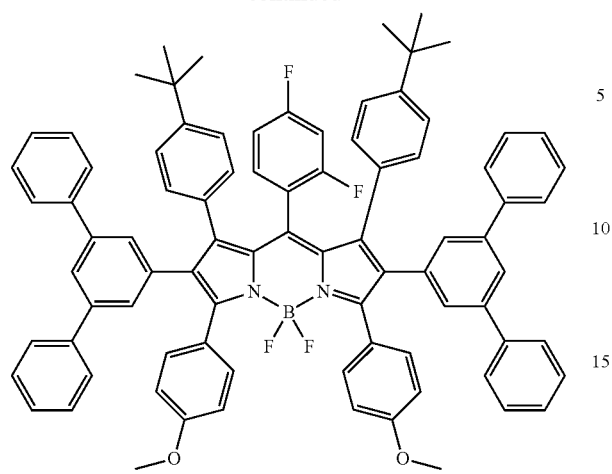
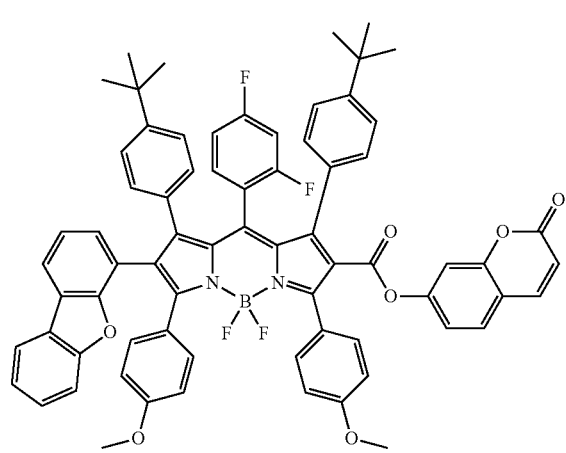
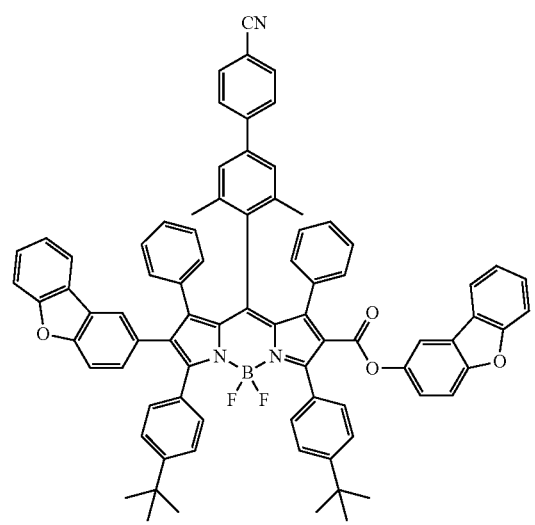
146
-continued
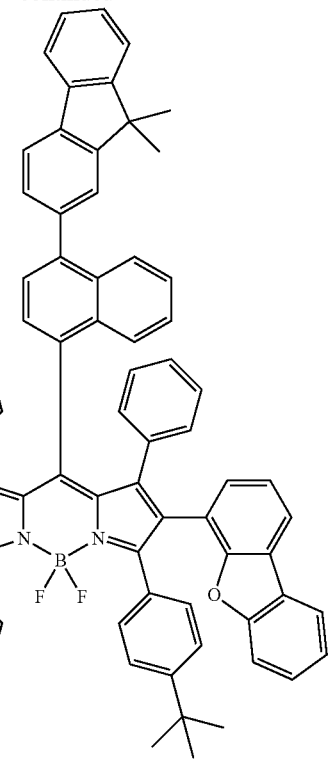
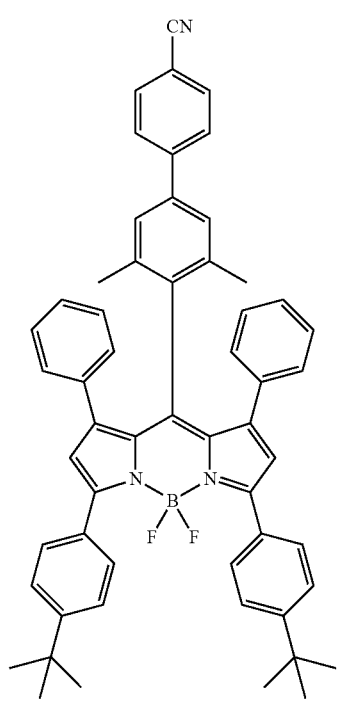

147
-continued
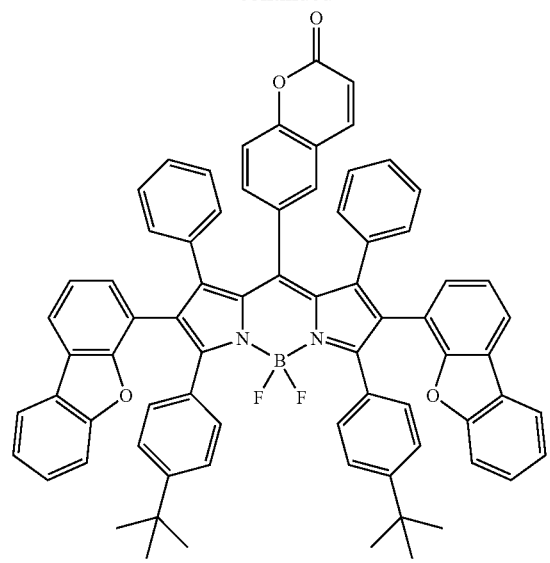
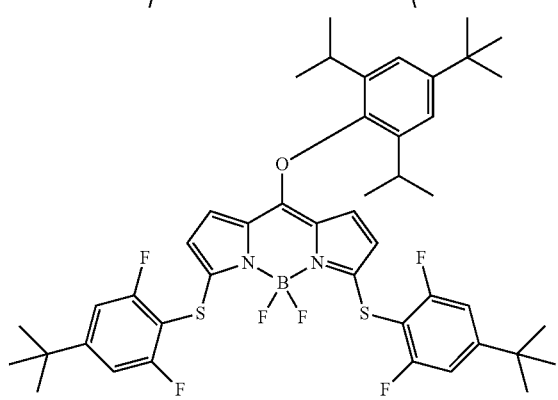
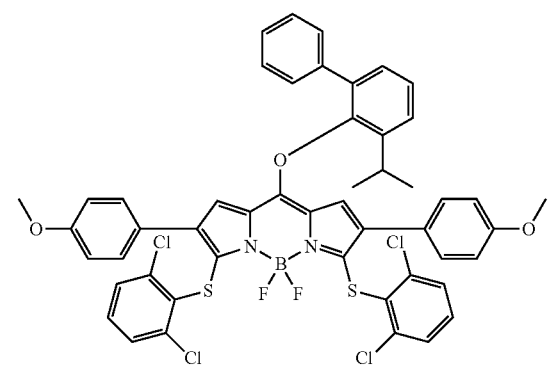
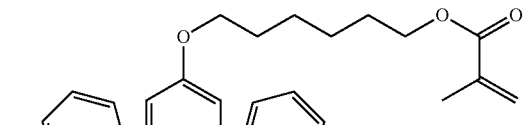
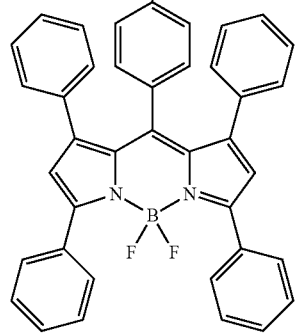
148
-continued
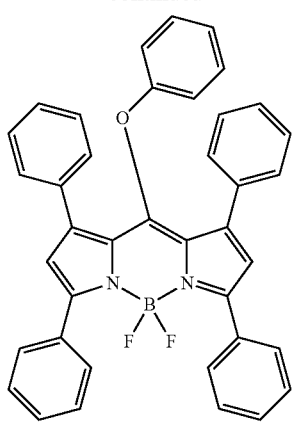
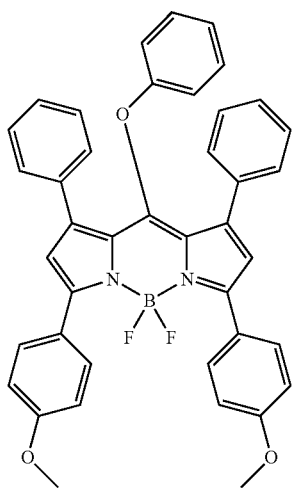
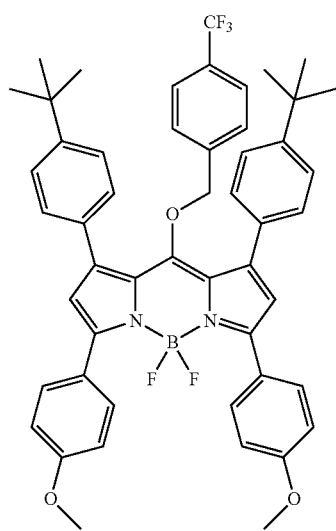

149
-continued
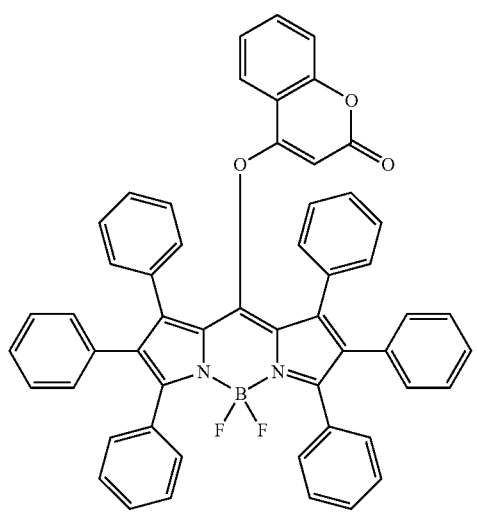
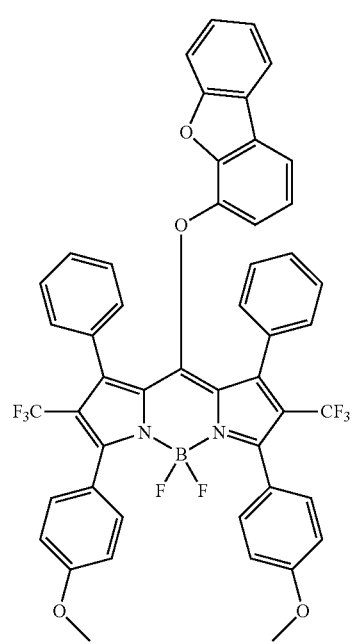
150
-continued
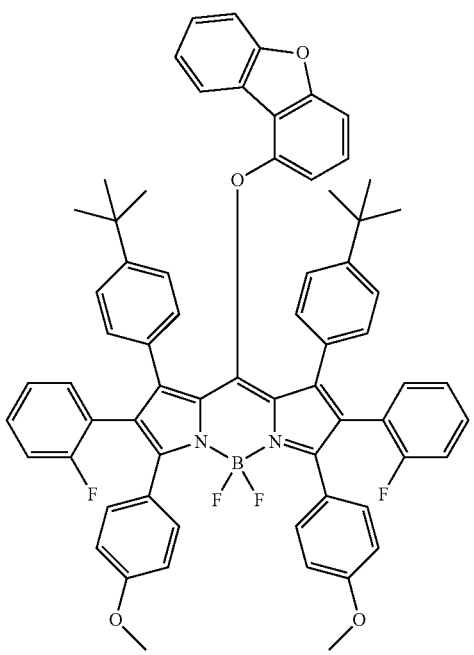
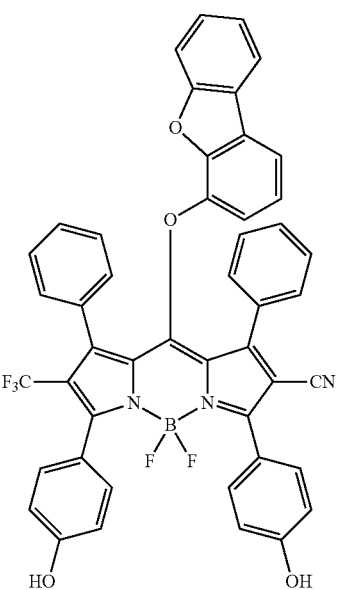
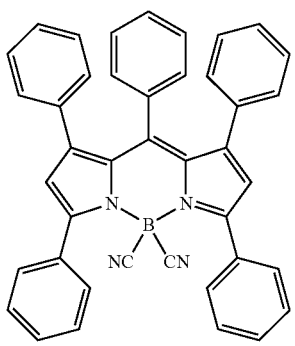

151
-continued
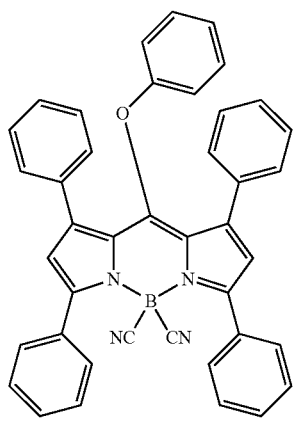
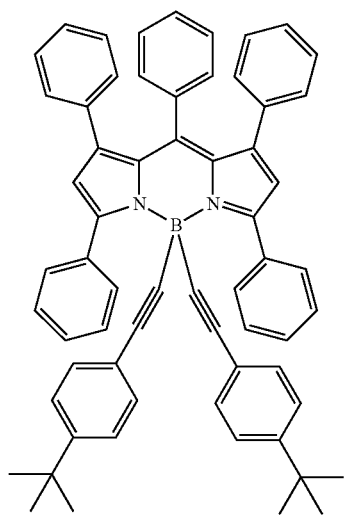
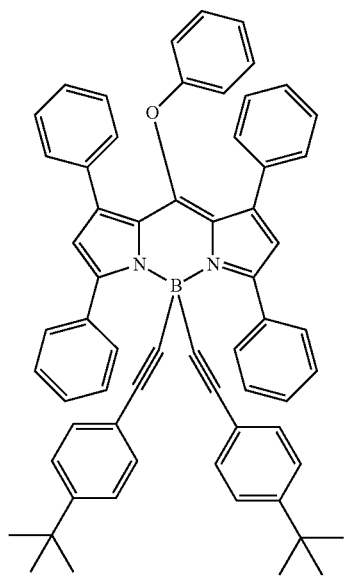
152
-continued
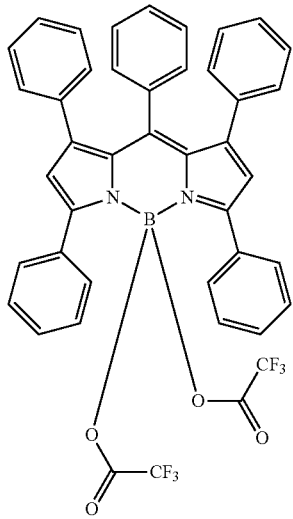
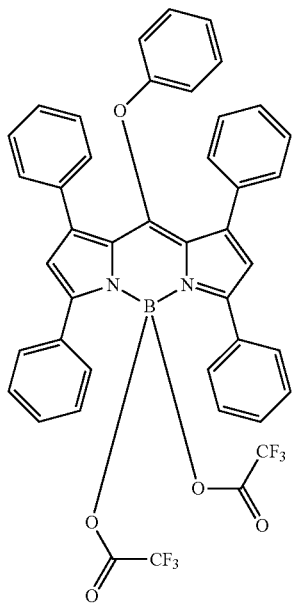
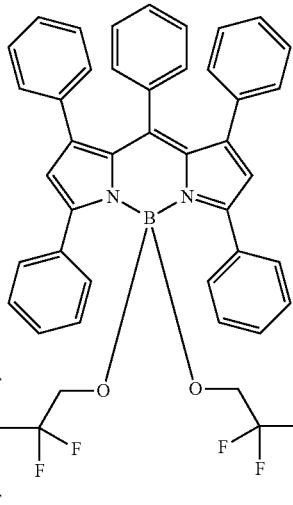

153
-continued
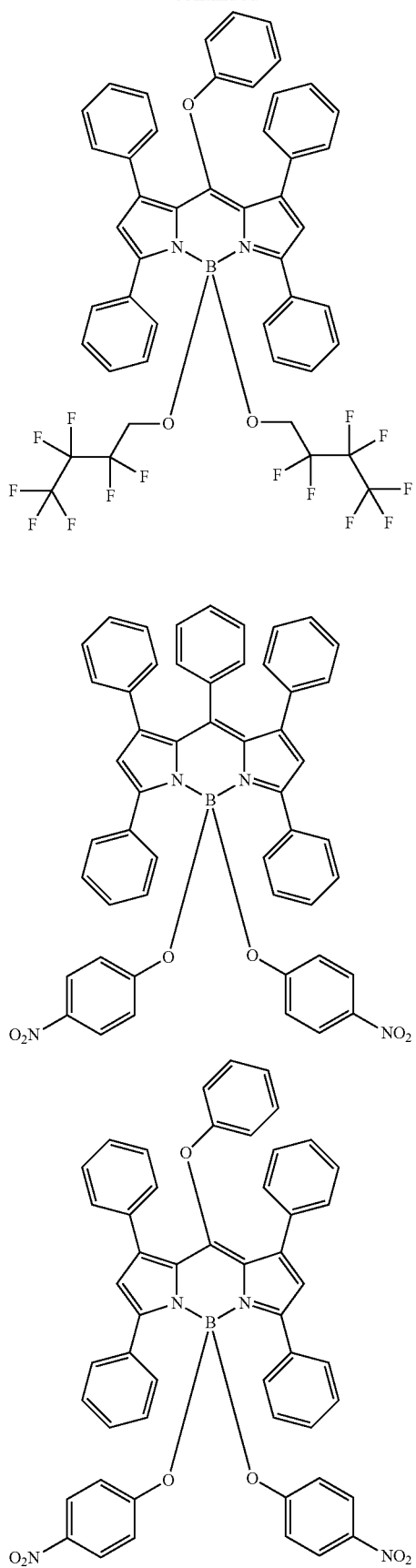
154
-continued
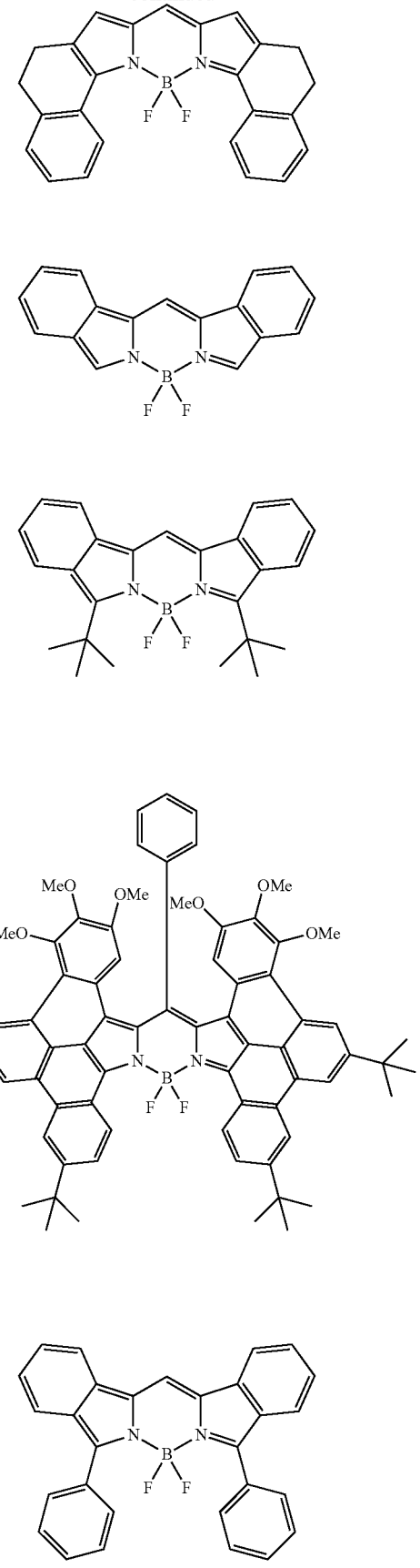

-continued

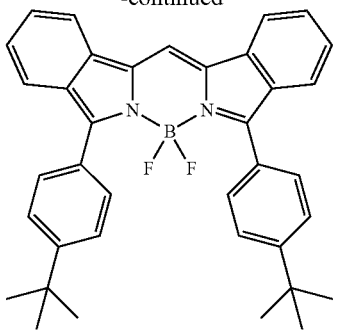

-continued

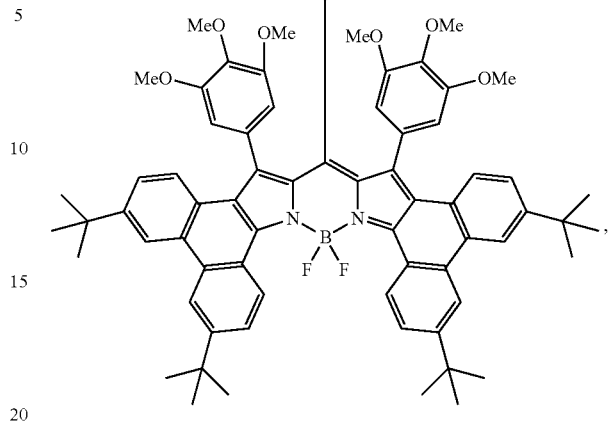

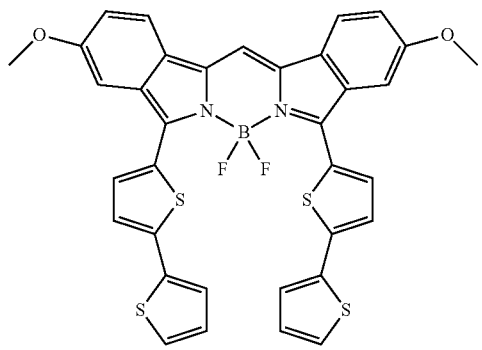

wherein
Me is a methyl group; and
Ph is a phenyl group.

7. The color conversion composition of claim 1, wherein, based on a total 100 parts by weight of the color conversion composition,
  a content of the compound selected from any one of the compounds in the Group I is from 0.1 parts by weight to 3 parts by weight; and
  a content of the compound represented by the Chemical Formula 2 is from 0.15 parts by weight to 2.5 parts by weight.

8. The color conversion composition of claim 1, further comprising a resin matrix.

9. A color conversion film comprising the color conversion composition of claim 1, or a cured material thereof.

10. A backlight unit comprising the color conversion film of claim 9.

11. The backlight unit of claim 10 comprising a light source, wherein the light source emits blue light.

12. A display apparatus comprising the backlight unit of claim 10.

* * * * *